United States Patent
Bublot et al.

(10) Patent No.: US 11,421,249 B2
(45) Date of Patent: *Aug. 23, 2022

(54) RECOMBINANT HVT VECTORS EXPRESSING MULTIPLE ANTIGENS OF AVIAN PATHOGENS AND USES THEREOF

(71) Applicant: BOEHRINGER INGELHEIM ANIMAL HEALTH USA INC., Duluth, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US); Aemro Kassa, Watkinsville, GA (US)

(73) Assignee: BOEHRINGER INGELHEIM ANIMAL HEALTH USA INC., Duluth, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/035,109

(22) Filed: Sep. 28, 2020

(65) Prior Publication Data

US 2021/0010033 A1 Jan. 14, 2021

Related U.S. Application Data

(63) Continuation of application No. 16/393,743, filed on Apr. 24, 2019, now Pat. No. 10,822,620, which is a continuation of application No. 15/840,764, filed on Dec. 13, 2017, now Pat. No. 10,323,257.

(60) Provisional application No. 62/433,842, filed on Dec. 14, 2016.

(51) Int. Cl.
| | |
|---|---|
| *C12N 15/869* | (2006.01) |
| *A61K 39/12* | (2006.01) |
| *A61K 39/155* | (2006.01) |
| *A61K 39/245* | (2006.01) |
| *A61K 39/295* | (2006.01) |
| *C07K 14/03* | (2006.01) |
| *C07K 14/08* | (2006.01) |
| *C12N 7/00* | (2006.01) |

(52) U.S. Cl.
CPC ............ *C12N 15/869* (2013.01); *A61K 39/12* (2013.01); *A61K 39/155* (2013.01); *A61K 39/245* (2013.01); *A61K 39/295* (2013.01); *C07K 14/03* (2013.01); *C07K 14/08* (2013.01); *C12N 7/00* (2013.01); *C12N 2710/16311* (2013.01); *C12N 2710/16334* (2013.01); *C12N 2710/16343* (2013.01); *C12N 2710/16363* (2013.01); *C12N 2720/10034* (2013.01); *C12N 2760/16163* (2013.01); *C12N 2760/18134* (2013.01); *C12N 2760/18163* (2013.01); *C12N 2830/20* (2013.01); *C12N 2830/50* (2013.01); *C12N 2840/203* (2013.01)

(58) Field of Classification Search
CPC ................... C12N 15/869; C12N 7/00; C12N 2710/16311; C12N 2710/16334; C12N 2710/16343; C12N 2710/16363; C12N 2720/10034; C12N 2760/16163; C12N 2760/18134; C12N 2760/18163; C12N 2830/20; C12N 2830/50; C12N 2840/203; C12N 2710/16022; C12N 2710/16034; C12N 2710/16322; C12N 2710/16634; C12N 2720/10022; C12N 2760/18122; C12N 2770/20034; C12N 15/86; A61K 39/12; A61K 39/155; A61K 39/245; A61K 39/295; A61K 2039/545; A61K 2039/552; A61K 39/17; C07K 14/03; C07K 14/08; C07K 14/005; A61P 31/04; A61P 31/12; A61P 31/14; A61P 31/20; A61P 31/22; A61P 37/04; A61P 43/00
See application file for complete search history.

(56) References Cited

U.S. PATENT DOCUMENTS

2015/0118250 A1* 4/2015 Fujisawa ............... A61K 39/245
424/159.1

FOREIGN PATENT DOCUMENTS

WO WO-2013082327 A1 * 6/2013 ............. A61P 31/12

OTHER PUBLICATIONS

De Felipe P. Genet Vaccines Ther. Sep. 13, 2004;2(1):13. (Year: 2004).*
Harmache A. J Virol. Oct. 2014;88(19):11617-23. Epub Jul. 16, 2014. (Year: 2014).*

* cited by examiner

*Primary Examiner* — Rachel B Gill
(74) *Attorney, Agent, or Firm* — Jamie Graham

(57) ABSTRACT

The present invention provides recombinant herpesvirus of turkeys (HVT) vectors that contain and express antigens of avian pathogens, compositions comprising the recombinant HVT vectors and polyvalent vaccines comprising the recombinant HVT vectors. The present invention further provides methods of vaccination against a variety of avian pathogens and method of producing the recombinant HVT vectors.

16 Claims, 34 Drawing Sheets
Specification includes a Sequence Listing.

Figure 1

| SEQ ID NO: | type | Gene Description |
|---|---|---|
| 1 | DNA | Polynucleotide encoding IBDV VP2 |
| 2 | protein | IBDV VP2 |
| 3 | DNA | Polynucleotide encoding NDV-F of NDV strain VIId, codon-optimized in pFSV40VP2 (vHVT309) and pFIRESVP2 (vHVT310) |
| 4 | DNA | Polynucleotide encoding NDV-F of NDV strain VIId, wild-type in pFP2AVP2 (vHVT311), pFwtSV40VP2 (vHVT313), pVP2IRESFwt (vHVT316) and pFwtIRESgD (vHVT322) |
| 5 | protein | NDV-F protein (vHVT309, vHVT310, vHVT311, vHVT313, vHVT316, vHVT322) |
| 6 | DNA | mCMV IE promoter for IBDV VP2 |
| 7 | DNA | SV40 Promoter for NDV F and ILTV gD |
| 8 | DNA | SV40 Poly A |
| 9 | DNA | Synthetic Poly A |
| 10 | DNA | IRES in pFIRESVP2, pVP2IRESgD and pVP2IRESFwt |
| 11 | DNA | Polynucleotide encoding P2A in pFP2AVP2 |
| 12 | DNA | Plasmid pFSV40VP2 for vHVT309 |
| 13 | DNA | Plasmid pFIRESVP2 for vHVT310 |
| 14 | DNA | Plasmid pFP2AVP2 for vHVT311 |
| 15 | DNA | Plasmid pVP2IRESgD for vHVT317 |
| 16 | DNA | Polynucleotide encoding ILTV gD, wild-type in pVP2IRESgD (vHVT317), HVT US2SVgDwtsyn (vHVT407), pHVTIG1gDCaFopt (vHVT308), pFwtIRESgD (vHVT322), and pHVTUS2SVgDwtsyn (vHVT406) |
| 17 | protein | ILTV gD |
| 18 | DNA | Plasmid pFwtSV40VP2 for vHVT313 |
| 19 | DNA | Plasmid pVP2IRESFwt for vHVT316 |
| 20 | DNA | Plasmid HVT US2SVgDwtsyn for vHVT407 |
| 21 | DNA | Polynucleotide encoding NDV-F of genotype V, codon-optimized in pHVTIG1gDCaFopt (vHVT308) |
| 22 | protein | NDV-F of genotype V (vHVT308) |
| 23 | DNA | HHV3gB promoter (reverse direction) |
| 24 | DNA | HHV3gB promoter |
| 25 | DNA | Plasmid pHVTIG1gDCaFopt for vHVT308 |
| 26 | DNA | Plasmid pFwtIRESgD for vHVT322 |
| 27 | DNA | pHVTUS2SVgDwtsyn for vHVT406 |

Genome Structure of HVT and Insertion Sites

Genomic Structure of HVT, ORFs of the *BamHI* fragment,
and Insertion/Replacement Locations
(GenBank accession number for HVT FC126 sequence: AF291866.1)

Figure 3 pFSV40VP2 plasmid map

IG1 Arm — Syn Poly a tail — VIId Codon Opt NDV-F — SV40 Promoter — SV40 Poly A — VP2 pFSV40VP2.
7505 bp

Schematic representation of primer binding sites for vHVT309 vHVT309 vHVT309 Identity PCR

Lane 1: no template
Lane 2: Vaxxitek
Lane 3: vHVT309 pFIRESVP2 plasmid map

Schematic representation of primer binding sites for vHVT310

Figure 8 vHVT310 identity PCR

| M 1 2 3 | M 1 2 3 | M 1 2 3 | M 1 2 3 |

| MB080+MB081 | MB080+NDVFVIIdopt.F | MB080+VP2.F | SV40tailR+mCMVF |

Lane 1:     no template
Lane 2:     Vaxxitek
Lane 3:     vHVT310 pFP2AVP2 plasmid map

Figure 10

Schematic representation of primer binding sites for vHVT311

NDV F VIId wildtype
NDVFVIIdwt.F
SV40 Poly A
SV40tailR          VP2.F                          mCMVF
IG1 Arm MB080      P2A      VP2        MCMV       MB081
                                                  IG1 Arm vHVT311

Figure 11 vHVT311 identity PCR

| M 1 2 3 | M 1 2 3 | M 1 2 3 | M 1 2 3 |

MB080+MB081      MB080+           MB080+      SV40tailR+
                 NDVFVIIdwt.F     VP2.F       mCMVF Lane 1:    no template
Lane 2:    Vaxxitek
Lane 3:    vHVT311 pVP2IRESgD plasmid map

Schematic representation of primer binding sites for vHVT317

Figure 14 vHVT317 identity PCR

| M | 1 | 2 | 3 | M | 1 | 2 | 3 | M | 1 | 2 | 3 | M | 1 | 2 | 3 |

MB080+
MB081 mCMVF+
SV40tailR

MB080+
ILTgDwt.F

MB080+
VP2.F

Lane 1: no template
Lane 2: Vaxxitek
Lane 3: vHVT317 pFwtSV40VP2 plasmid map

Figure 16

Schematic representation of primer binding sites for vHVT313

Fragment of vHVT313 with primers - sequence verified
7658 bp (molecule 164411 bp)

vHVT313 identity PCR

Lane 1: no template
Lane 2: Vaxxitek
Lane 3: vHVT313 pVP2IRESFwt plasmid map

Figure 19

Schematic representation of primer binding sites for vHVT316

Fragment of vHVT316 with primers
7406 bp (molecule 164411 bp)

Labels: IG1 Arm, MB080, SV40tailR, SV40 Poly A, 312P6, VIId NDV-Fwt, IRES, VP2.F, VP2, MCMV, mCMVF, MB081, IG1 Arm vHVT316 identity PCR Lane 1: no template
Lane 2: Vaxxitek
Lane 3: vHVT316

Figure 21A

Sequence alignments of NDV F polynucleotides

```
                        1                                                  50
SEQ ID NO:21    (1)     ......................TGA...........
SEQ ID NO:3     (1)     ..................GAAT.....C........TGAGCTGATCAC
SEQ ID NO:4     (1)     ....TCCAAA..TTCT....AT.....A..T.GATC.TCATCAC
                        51                                                100
SEQ ID NO:21   (51)     A.AAC.AT.CT.AT.....A.TC.AT.TCC..A.AA.CAG..T.A.
SEQ ID NO:3    (51)     ..C..ATGCT.AT.....TC.AT.ACC.A.AA...CT.AT
SEQ ID NO:4    (51)     ..GA.T.GCT.ATAT...T.TA.CT..GAAA...TCTT..
                        101                                               150
SEQ ID NO:21  (101)     ..CA........................................AAGC..
SEQ ID NO:3   (101)     ACC.C...............A..GT...........AAGC.T
SEQ ID NO:4   (101)     ..GC.TCT.CAG.T.ACGAA.T.AGTAA.AGA.AT.AGGCA.C
                        151                                               200
SEQ ID NO:21  (151)     AA.A.C.AC..........C.....TCATA..A.C.C..
SEQ ID NO:3   (151)     AA..GTACA......A.AC....ATCAT..GAAGT.C..C
SEQ ID NO:4   (151)     AAT.ATACA.TTCGTCT.A.A.AC.GTCAA.A.A..AAGT.C.CC
                        201                                               250
SEQ ID NO:21  (201)     ..........A..C.A.AA..A.CC................TCA..
SEQ ID NO:3   (201)     ..........A..C.A.AA..A.CC................TCA..C
SEQ ID NO:4   (201)     G..T......AT.AGGAA.G..TC.AA.A..C..ATAGAG..A.
                        251                                               300
SEQ ID NO:21  (251)     A.AAC.GAAC......A.CC.A.T...TCCT..C...GGC.A..C.
SEQ ID NO:3   (251)     A.AAC.GAAC......A.CC.A.T...TCCT..C...GGC.A..C.
SEQ ID NO:4   (251)     ATAA.AGAACA.GACTA.TT.GG.CA.TCTC.T.GC.AGTC.A.CC
                        301                                               350
SEQ ID NO:21  (301)     AGA.T.CA.G..AG.CC...ACA....G.GAG..AAGCA...GC.
SEQ ID NO:3   (301)     A.TC...A.G...G.C...G.AC.....GAC.AAGC...G..
SEQ ID NO:4   (301)     ..A.T.A.GG.T..T...CA.TCT.CA.AGCCAA..AGCCC.C
                        351                                               400
SEQ ID NO:21  (351)     G.G....A.CAT.AGA.C.T.C.CT...CA.AGC..
SEQ ID NO:3   (351)     ..C..C.C..GAT..A.C.A.C.T.AGT.CTA.GC..
SEQ ID NO:4   (351)     ..AC.TC..CT.T.T.CA.GT.AC.TC.T.GC.T.CAA.AC.GGCA.
                        401                                               450
SEQ ID NO:21  (401)     AGAT.....A..C.G.C..T.....TT..GC.AA.T..AG.AA..A.
SEQ ID NO:3   (401)     AGAT.....A..C.A.C.G..T.AA.TCA..CC.AA...AGAA..C.AA.
SEQ ID NO:4   (401)     AGATAA.AGCA.TC.GG.CC.AATAA.AC.AA..AGAAT..GC.AA.
                        451                                               500
SEQ ID NO:21  (451)     ATCCT.......GC..A..AG.AGCAT.C.GCA.AA.CAC.A.GTCA..
SEQ ID NO:3   (451)     ATCCT........GC..A..AG.AGCATTC.GCA.AA.CAG.A.GTCA..
SEQ ID NO:4   (451)     ATCCTCC.GC.TAAGCAGCAT.CTGCAA.CA.ATCAAATCTCCAT.A
                        501                                               550
SEQ ID NO:21  (501)     A.T.AAA.C.A.T.....AG.CT.GT.C.CT.TCC.A.GAT.AG.
SEQ ID NO:3   (501)     A.T.AC.A.AC.C.T.AG..A.CT.CC.C.CTGCC.A.GATCA.
SEQ ID NO:4   (501)     A.TCAC.A.A.T.A..A.A.CTA.A.T.A.ATT.GGAAGATGGA.
                        551                                               600
SEQ ID NO:21  (551)     A.T.C.TAA.AAA..AC.T..AA.AA.C....G..GGA.T.AT
SEQ ID NO:3   (551)     A.TT.C.T.A.A.C.T...AA.AA.C....G..GAC.TGA.T
SEQ ID NO:4   (551)     A.TT.CCAAT.A.AC.TAATAAT.CG.GC.AGAAT.GACT.TA.A
```

Figure 21B

Sequence alignment showing SEQ ID NO:21, SEQ ID NO:3, and SEQ ID NO:4 from positions 601 to 1250. Most sequence content is obscured by shading/highlighting and not legibly readable.

Figure 21C

```
                         1251                                               1300
SEQ ID NO:21     (1251)  [sequence]
SEQ ID NO:3      (1251)  [sequence]
SEQ ID NO:4      (1251)  [sequence]
                         1301                                               1350
SEQ ID NO:21     (1301)  [sequence]
SEQ ID NO:3      (1301)  [sequence]
SEQ ID NO:4      (1301)  AAGGTCATGGGAATTCA..AACTTATTAAAGAACATCAATA
                         1351                                               1400
SEQ ID NO:21     (1351)  [sequence]
SEQ ID NO:3      (1351)  [sequence]
SEQ ID NO:4      (1351)  TACATTCTCAACCATCGTCACAGGAATCTTGATAATCAACTCAAT
                         1401                                               1450
SEQ ID NO:21     (1401)  [sequence]
SEQ ID NO:3      (1401)  [sequence]
SEQ ID NO:4      (1401)  TGAAACCTCAAGAATTCAATA..T..CTTCGTATTGGAGAA
                         1451                                               1500
SEQ ID NO:21     (1451)  [sequence]
SEQ ID NO:3      (1451)  [sequence]
SEQ ID NO:4      (1451)  CAACACAACGTAAAAAGCAATTCCACAACAACACATGC
                         1501                                               1550
SEQ ID NO:21     (1501)  [sequence]
SEQ ID NO:3      (1501)  [sequence]
SEQ ID NO:4      (1501)  TCATACCTATATCGTTAACTCATTTTTACATTCCGTCAT
                         1551                                               1600
SEQ ID NO:21     (1551)  [sequence]
SEQ ID NO:3      (1551)  [sequence]
SEQ ID NO:4      (1551)  TAGTCCTGCGTTAAGTGTTAACTTAAGTACAACAACAACAATAA
                         1601                                               1650
SEQ ID NO:21     (1601)  [sequence]
SEQ ID NO:3      (1601)  [sequence]
SEQ ID NO:4      (1601)  AGAACTTGCTAGGCCTTGGAAAATACCTCGATTACATGAGGCGACT
                         1651
SEQ ID NO:21     (1651)  ACAAGAA
SEQ ID NO:3      (1651)  ACAAGAA
SEQ ID NO:4      (1651)  ACAACAAA
```

Sequence identity between SEQ ID NO:3 and SEQ ID NO:4 is 72.2%.
Sequence identity between SEQ ID NO:21 and SEQ ID NO:3 is 92.1%.
Sequence identity between SEQ ID NO:21 and SEQ ID NO:4 is 69.4%.

Figure 21D

Sequence alignments of NDV F proteins

SEQ ID NO:5 and SEQ ID NO:22 is 91.9% identical.

Figure 22

HVT US2SVgDwtsyn plasmid map

Figure 23 pHVTIG1gDCaFopt map

SV40 polyA — Intergene 1 arm — ILTgD — HHV3 gB — SV40 Promoter — NDV-F-CA02-CSmut — Syn Poly a tail — Intergene 1 arm — amp HVTIG1gDCaFopt
9331 bp

Figure 24

Schematic representation of primer binding sites for vHVT308

Fragment of vHVT308 PCR Identity
6526 bp (molecule 163534 bp)

vHVT308 Identity PCR

Lane 1: no template
Lane 2: HVT FC126
Lane 3: vHVT308 pre-MSV
Lane 4: vHVT308 pre-MSV+13 passages

Figure 26 pFwtIRESgD plasmid

Intergene 1 arm — pMCMV — NDV-F VIId wt — IRES — ILTV gD wildtype — SV40 Poly A — Intergene 1 arm — amp pFwtIRESgD
10138 bp

Figure 27

Schematic representation of primer binding sites for vHVT322

Fragment of vHVT322 with primers
6762 bp (molecule 164341 bp)

vHVT322 Identity PCR

Lane 1: no template
Lane 2: vHVT13
Lane 3: vHVT322 pre-MSV
Lane 4: vHVT322 pre-MSV+13

Figure 29 pHVTUS2SVgDwtsyn plasmid map pHVTUS2SVgDwtsyn
6934 bp

Labels: SOrf3 Arm, SV40 Promoter, ILTV-gDwt, Syn PolyA, US2 Arm

Schematic representation of primer binding sites for vHVT406 vHVT406 Identity PCR

Lane 1: no template
Lane 2: FC126
Lane 3: donor plasmid pHVTUS2SVgDwtsyn
Lane 4: vHVT406 pre-MSV
Lane 5: vHVT406 pre-MSV+13

RECOMBINANT HVT VECTORS EXPRESSING MULTIPLE ANTIGENS OF AVIAN PATHOGENS AND USES THEREOF

CROSS-REFERENCE TO RELATED APPLICATIONS

This application is a continuation of U.S. patent application Ser. No. 16/393,743, filed Apr. 24, 2019, now U.S. patent Ser. No. 10,822,620, which is a continuation of U.S. patent application Ser. No. 15/840,764, filed Dec. 13, 2017, now U.S. Pat. No. 10,323,257, which claims the benefit of U.S. Application No. 62/433,842, filed Dec. 14, 2016, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 1, 2 and 3 (HVT) (WO87/04463; WO2013/082317), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84; U.S. Pat. No. 5,980,906). Other HVT vectors of interest are those expressing either NDV (Morgan et al 1992, Avian dis. 36, 858-70; U.S. Pat. Nos. 6,866,852; 5,650,153), ILTV (Johnson et al, 2010 Avian Dis 54, 1251-1259; U.S. Pat. Nos. 6,299,882; 5,853,733, EP 1801204), or NDV and IBDV (U.S. Pat. No. 9,114,108; WO2016102647, WO2013/057235, WO2015032910, WO2013144355) protective gene(s). US2016/0158347 reported the use of the oligodeoxynucleotide TLR21 agonist to increase the immune response against the antigen that expressed by HVT vector.

One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancún, Mexico, Aug. 14-18, 2011; Slacum G, Hein R. and Lynch P., 2009, The compatibility of HVT recombinants with other Marek's disease vaccines, $58^{th}$ Western Poultry Disease Conference, Sacramento, Calif., USA, March $23^{rd}$-$25^{th}$, p 84).

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between two HVT-based vector vaccines.

SUMMARY OF THE INVENTION

The present invention showed surprising result when polyvalent compositions or vaccines comprising recombinant HVT vector were effective to protect animals against a variety of avian pathogens without interference. Surprising results were also observed when various combinations of promoters/linkers, codon-optimized gene, polyA tails and insertion sites conferred different levels of efficacy and stability to the expression of one or more heterologous genes in vivo and in vitro. The present invention provides stable HVT vectors which are able to efficiently express multiple genes and overcomes the well-known problem that HVT vectors with multiple inserts are less stable.

The present invention relates to a recombinant HVT vector comprising one, two or more heterologous polynucleotides coding for and expressing at least one antigen of an avian pathogen.

The present invention provides a composition or vaccine comprising one or more recombinant HVT vectors comprising one, two or more heterologous polynucleotides coding for and expressing at least one antigen of an avian pathogen.

The present invention relates to a method of vaccinating an animal, or inducing an immunogenic or protective response in an animal, comprising at least one administration of the composition or vector of the present invention.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 3 depicts pFSV40VP2 plasmid map.

FIG. 8 depicts PCR identity result of vHVT310.

FIG. 10 depicts schematic representation of primer binding sites for vHVT311.

FIG. 11 depicts PCR identity result of vHVT311.

FIG. 14 depicts PCR identity result of vHVT317.

FIG. 16 depicts schematic representation of primer binding sites for vHVT313.

FIG. 19 depicts schematic representation of primer binding sites for vHVT316.

Figure 21D:
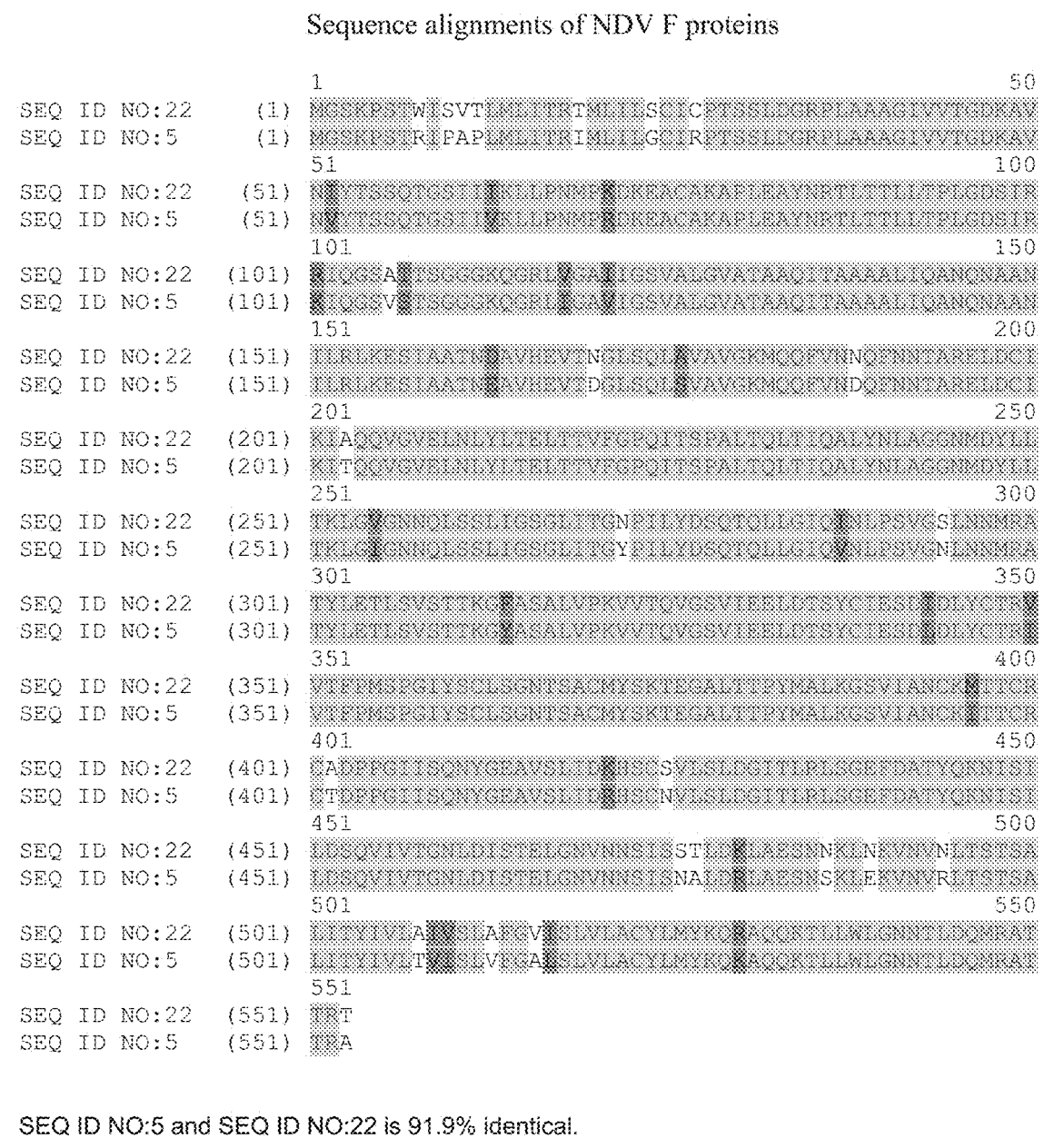

FIG. 21A-21D depict DNA and protein sequence alignments.

FIG. 22 depicts HVT US2SVgDwtsyn plasmid map.

FIG. 23 depicts pHVTIG1gDCaFopt plasmid map.

FIG. 24 depicts schematic representation of primer binding sites for vHVT308.

FIG. 26 depicts pFwtIRESgD plasmid map.

FIG. 27 depicts schematic representation of primer binding sites for vHVT322.

FIG. 29 depicts pHVTUS2SVgDwtsyn plasmid map.

DETAILED DESCRIPTION OF THE INVENTION

Figure 2:
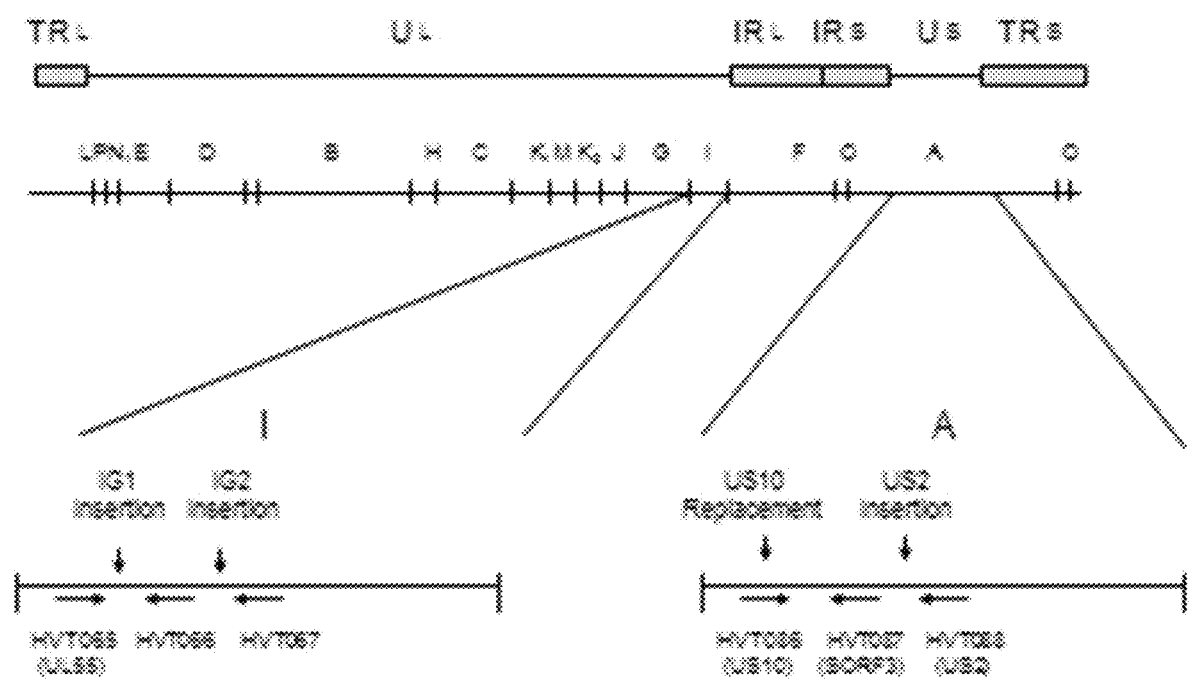
FIG. 2 depicts the genome structure of HVT and its insertion sites.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. This invention includes all modifications and equivalents of the subject matter recited in the aspects or claims presented herein to the maximum extent permitted by applicable law.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

It will also be understood that, although the terms first, second, etc. may be used herein to describe various elements, these elements should not be limited by these terms. These terms are only used to distinguish one element from another. For example, a first gesture could be termed a second gesture, and, similarly, a second gesture could be termed a first gesture, without departing from the scope of the present invention. All methods or processes described herein can be performed in any suitable order unless otherwise indicated herein or otherwise clearly contradicted by context.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The term "about" as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the invention provides a recombinant HVT viral vector comprising one, two or more heterologous polynucleotides coding for and expressing at least one antigen or polypeptide of an avian pathogen. The HVT strains used for the recombinant viral vector may be any HVT strains, including, but not limited to, the HVT strain FC126 (Igarashi T. et al., J. Gen. Virol. 70, 1789-1804, 1989).

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), Infectious Bursal Disease Virus (IBDV) VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemagglutinin (HA), influenza neuraminidase (NA), protective genes derived from *Mycoplasma gallisepticum* (MG), or *Mycoplasma synoviae* (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, avian retrovirus, avian picornavirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *Escherichia coli*.

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant HVT viral vector comprising one, two or more heterologous polynucleotides coding for and expressing the NDV-F antigen or polypeptide, the IBDV VP2 antigen or polypeptide, the ILTV gD antigen or polypeptide, or a combination thereof. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:5 or 22, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an NDV-F antigen or polypeptide having at least 70%, 75%, 80%, 85%, 90%, 95%, 96%, 97%, 98% or 99% sequence identity to a polypeptide having the sequence as set forth in SEQ ID NO:5. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:3, 4 or 21.

In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an IBDV VP2 antigen or polypeptide having at least 70%, 75%, 80%, 85%, 90%, 95%, 96%, 97%, 98% or 99% sequence identity to a polypeptide having the sequence as set forth in SEQ ID NO:2. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1.

In another aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encodes an ILTV gD antigen or polypeptide having at least 70%, 75%, 80%, 85%, 90%, 95%, 96%, 97%, 98% or 99% sequence identity to a polypeptide having the sequence as set forth in SEQ ID NO:17. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:16.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F, IBDV VP2 or ILTV gD polypeptides, the DNA sequence of these genes can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F, IBDV VP2 or ILTV gD protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F, IBDV VP2 or ILTV gD polypeptide encoded by the nucleotide sequence is functionally unchanged.

Successful expression of the heterologous polynucleotides by the recombinant/modified infectious virus requires two conditions. First, the heterologous polynucleotides must be inserted or introduced into a region of the genome of the virus in order that the modified virus remains viable. The second condition for expression of inserted heterologous polynucleotides is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

The insertion site may be any non-essential region of the HVT genome, including, but not limited to, the region between the STOP codon of ORF UL55 and the junction of UL with the adjacent repeat region (intergenic region 1, the IG1 locus, U.S. Pat. No. 5,980,906), the IG2 (intergenic region 2) locus, the IG3 (intergenic region 3) locus, the UL43 locus, the US10 locus, the US2 locus, the SORF3/US2 locus (see FIG. 2)

In general, it is advantageous to employ a strong promoter functional in eukaryotic cells. The promoters include, but are not limited to, an immediate early (IE) human cytomegalovirus (CMV) (hCMV) promoter, mouse CMV (mCMV) IE promoter, guinea pig CMV (gpCMV) IE promoter, an SV40 promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, HHV3gB promoter (Human Herpesvirus Type 3 glycoprotein B promoter), Infectious Laryngotracheitis Virus promoters such as those of glycoprotein gB, gE, gI, gD, gC genes, or other herpesvirus promoters.

One embodiment of the invention provides a recombinant HVT vector comprising a first heterologous polynucleotide coding for and expressing the IBDV VP2 antigen or polypeptide and a second polynucleotide coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:5. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2. In another aspect, the polynucleotide encoding the NDV-F polypeptide is operably linked to the SV40 promoter having the sequence as set forth in SEQ ID NO:7 and the expression of NDV-F antigen or polypeptide is regulated by the SV40 promoter. In yet another aspect, the expression of NDV-F antigen or polypeptide is regulated by the SV40 polyA signal having the sequence as set forth in SEQ ID NO:8, or the synthetic polyA signal having the sequence as set forth in SEQ ID NO:9. In another aspect, the expression of IBDV VP2 antigen or polypeptide is regulated by the mCMV-IE promoter having the sequence as set forth in SEQ ID NO:6 and the SV40 polyA signal having the sequence as set forth in SEQ ID NO:8, or the synthetic polyA signal having the sequence as set forth in SEQ ID NO:9.

Another embodiment of the invention provides a recombinant HVT vector comprising a first heterologous polynucleotide coding for and expressing the IBDV VP2 antigen or polypeptide and a second polynucleotide coding for and expressing the NDV-F antigen or polypeptide, and further comprising a sequence which regulates the expression of the second polynucleotide. The regulatory sequences or linkers may be an internal ribosome entry site (IRES), an RNA sequence derived from Encephalomyocarditis virus (EMCV), or a sequence encoding a self-cleaving porcine teschovirus-1 2A or foot and mouth disease virus (FMDV) peptide (P2A).

In one aspect of the embodiment, the recombinant HVT vector comprises a first polynucleotide encoding the IBDV VP2 antigen and a second polynucleotide encoding the NDV-F antigen, and further comprises the IRES having the sequence as set forth in SEQ ID NO:10. In another aspect of the embodiment, the recombinant HVT comprises a first polynucleotide encoding the IBDV VP2 antigen and a second polynucleotide encoding the NDV-F antigen, and further comprises the P2A encoding polynucleotide having the sequence as set forth in SEQ ID NO:11.

One embodiment of the invention provides a recombinant HVT vector comprising a first heterologous polynucleotide coding for and expressing the NDV F antigen or polypeptide and a second polynucleotide coding for and expressing the ILTV gD antigen or polypeptide, and further comprising a sequence which regulates the expression of the second polynucleotide. The regulatory sequences or linkers may be an internal ribosome entry site (IRES), an RNA sequence derived from Encephalomyocarditis virus (EMCV), or a sequence encoding a self-cleaving porcine teschovirus-1 2A or foot and mouth disease virus (FMDV) peptide (P2A). In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the NDV F antigen or polypeptide has at least 70%, 75%, 80%, 85%, 90%, 95%, 96%, 97%, 98% or 99% sequence identity to a polypeptide having the sequence as set forth in SEQ ID NO:5 or 22. In yet another aspect of the embodiment, the recombinant HVT vector comprises a first polynucleotide encoding the NDV F antigen and a second polynucleotide encoding the ILTV gD antigen, and further comprises the IRES having the sequence as set forth in SEQ ID NO:10.

Another embodiment of the invention provides a recombinant HVT vector comprising a first heterologous polynucleotide coding for and expressing the NDV F antigen or polypeptide and a second polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the NDV F antigen or polypeptide has at least 70%, 75%, 80%, 85%, 90%, 95%, 96%, 97%, 98% or 99% sequence identity to a polypeptide having the sequence as set forth in SEQ ID NO:5 or 22. In one aspect, the polynucleotide encoding the NDV F polypeptide is operably linked to the SV40 promoter and the expression of NDV F antigen or polypeptide is regulated by the SV40 promoter. In another aspect, the polynucleotide encoding the ILTV gD polypeptide is operably linked to the HHV3gB promoter and the expression of ILTV gD antigen or polypeptide is regulated by the HHV3gB promoter. In yet another aspect, the HHV3gB promoter is in the reverse direction. In yet another aspect, the expressions of the NDV F antigen and ILTV gD antigen are regulated by SV40 promoter and reverse HHV3gB promoter, and are in opposite directions.

Another embodiment of the invention provides a recombinant HVT vector comprising a first heterologous polynucleotide coding for and expressing the IBDV VP2 antigen or polypeptide and a second polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:2. In yet another aspect of the embodiment, the recombinant HVT vector comprises a first polynucleotide encoding the IBDV VP2 antigen and a second polynucleotide encoding the ILTV gD antigen, and further comprises the IRES having the sequence as set forth in SEQ ID NO:10.

Another embodiment of the invention provides a recombinant HVT vector comprising a heterologous polynucleotide coding for and expressing the ILTV gD antigen or polypeptide. In one aspect of the embodiment, the ILTV gD antigen or polypeptide has at least 70%, 75%, 80%, 85%, 90%, 95%, 96%, 97%, 98% or 99% sequence identity to a polypeptide having the sequence as set forth in SEQ ID NO:17. In another aspect of the embodiment, the polynucleotide encoding the ILTV gD polypeptide is operably linked to the SV40 promoter and the expression of ILTV gD antigen or polypeptide is regulated by the SV40 promoter.

In one embodiment, the polynucleotides encoding the IBDV VP2 antigen, and/or NDV-F antigen, and/or ILTV gD antigen may be inserted in one or more locus regions selected from the group consisting of IG1, IG2, US10, US2, SORF3-US2 and gD of HVT genome. In another embodiment, the polynucleotides encoding the IBDV VP2 antigen, and/or NDV-F antigen, and/or ILTV gD antigen are inserted in the same locus, such as IG1 of HVT genome.

In one embodiment, the present invention relates to a pharmaceutical composition or vaccine comprising one or more recombinant HVT vectors of the present invention and a pharmaceutically or veterinarily acceptable carrier, excipient, vehicle or adjuvant. The HVT vector may comprise two heterologous polynucleotides, and wherein the first polynucleotide comprises a polynucleotide encoding a polypeptide selected from the group consisting of an Infectious Bursal Disease Virus (IBDV) VP2 antigen, an Infectious Laryngotracheitis Virus (ILTV) glycoprotein D (gD) antigen and a Newcastle Disease Virus F (NDV-F) antigen, and wherein the second polynucleotide comprises a polynucleotide encoding a polypeptide selected from the group consisting of an Infectious Bursal Disease Virus (IBDV) VP2 antigen, an Infectious Laryngotracheitis Virus (ILTV) glycoprotein D (gD) antigen and a Newcastle Disease Virus F (NDV-F) antigen.

In another embodiment, the present invention provides a composition or vaccine comprising an HVT viral vector comprising: i) a first heterologous polynucleotide coding for and expressing an IBDV VP2 antigen or an NDV-F antigen; ii) a second polynucleotide coding for and expressing an NDV-F antigen or an IBDV VP2 antigen; and iii) optionally a pharmaceutically or veterinarily acceptable carrier, excipient, vehicle or adjuvant. In yet another embodiment, the present invention provides a composition or vaccine comprising an HVT viral vector comprising: i) a first heterologous polynucleotide coding for and expressing an IBDV VP2 antigen or an ILTV gD antigen; ii) a second polynucleotide coding for and expressing an ILTV gD antigen or an IBDV VP2; and iii) optionally a pharmaceutically or veterinarily acceptable carrier, excipient, vehicle or adjuvant. In yet another embodiment, the present invention provides a composition or vaccine comprising an HVT viral vector comprising: i) a first heterologous polynucleotide coding for and expressing an NDV-F antigen or an ILTV gD antigen; ii) a second polynucleotide coding for and expressing an ILTV gD antigen or an NDV-F antigen; and iii) optionally a pharmaceutically or veterinarily acceptable carrier, excipient, vehicle or adjuvant. In yet another embodiment, the present invention provides a composition or vaccine comprising an HVT viral vector comprising a heterologous polynucleotide coding for and expressing an ILTV gD antigen, and optionally a pharmaceutically or veterinarily acceptable carrier, excipient, vehicle or adjuvant. In yet another embodiment, the present invention provides a composition or vaccine comprising an HVT comprising a polynucleotide having at least 70%, 75%, 80%, 85%, 90%, 95%, 96%, 97%, 98% or 99% sequence identity to a polynucleotide having the sequence as set forth in SEQ ID NO:1, 3, 4, 12, 13, 14, 15, 16, 18, 19, 20, 21, 25, 26 or 27. In one embodiment, it is shown that insertion of two or more heterologous polynucleotides in one locus confers better protection and efficacy then insertion in multiple loci. In another embodiment, it is shown that expressing more than one heterologous polynucleotide from a single mRNA through an IRES or P2A provides better protection and efficacy against avian diseases. In yet another embodiment, the experimental data provided by the present invention disclose that constructs comprising IRES elements provided better protection than constructs comprising P2A elements.

The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek's disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate), the Lactated Ringer's Injection diluent (sodium chloride, sodium lactate, potassium chloride and calcium chloride), or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvants or vehicles or excipients, including, but not limited to, alum; CpG oligonucleotides (ODN), in particular ODN 2006, 2007, 2059, or 2135 (Pontarollo R. A. et al., Vet. Immunol. Immunopath, 2002, 84: 43-59; Wernette C. M. et al., Vet. Immunol. Immunopath, 2002, 84: 223-236; Mutwiri G. et al., Vet. Immunol. Immunopath, 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology*, 6: p. 03, p. 157); N,N-dioctadecyl-N',N'-bis(2-hydroxyethyl) propanediamine (such as AVRIDINE®) (Ibid, p. 148); carbomer, chitosan (see U.S. Pat. No. 5,980,912).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In one embodiment, the adjuvant may include TS6 TS7, TS8 and TS9 (U.S. Pat. No. 7,371,395), LR2, LR3 and LR4 (U.S. Pat. No. 7,691,368), TSAP (US20110129494), TRI-GEN™ (Newport Labs), synthetic dsRNAs (e.g. poly-IC, poly-ICLC [HILTONOL®]), and MONTANIDE™ adjuvants (W/O, W/O/W, 01W, IMS and Gel; all produced by SEPPIC).

In another embodiment, the invention provides for the administration of a therapeutically effective amount of a vaccine or composition for the delivery of recombinant HVT vectors in a target cell. Determination of the therapeutically effective amount is routine experimentation for one of ordinary skill in the art.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum, Mycoplasma synoviae, Pasteurella* sp., *Avibacterium* sp., *E. coli* or *Clostridium* sp.

Usually, one administration of the vaccine in avian is performed either at one day-of-age by the subcutaneous or intramuscular route or in ovo in 17-19 day-old embryo. A second administration can be done within 0-30 days after the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The composition or vaccine may contain a dose from about $10^2$ to about $10^{20}$, about $10^3$ to about $10^{18}$, about $10^4$ to about $10^{16}$, about $10^5$ to about $10^{12}$ VLPs (virus like particles) produced in vitro or in vivo from a viral vector, a plasmid, or baculovirus. The viral vector may be titrated based on any virus titration methods including, but not limited to, FFA (Focus Forming Assay) or FFU (Focus Forming Unit), TCID$_{50}$ (50% Tissue Culture Infective Dose), PFU (Plaque Forming Units), and FAID$_{50}$ (50% Fluorescent Antibody Infectious Dose), and the VLPs produced in vitro can be titrated by hemagglutination assay, ELISA, and electron microscopy. Other methods may also be applicable depending on the type of VLP.

The composition or vaccine may contain from about $10^{2.0}$ to about $10^{7.0}$ TCID$_{50}$ or PFU/dose, from about $10^{2.0}$ to about $10^{7.0}$ TCID$_{50}$ or PFU/dose, and from about $10^{2.0}$ to about $10^{6.5}$ TCID$_{50}$ or PFU/dose.

The dose volumes can be between about 0.01 and about 10 ml, between about 0.01 and about 5 ml.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 4th edition, Cold Spring Harbor Laboratory, Cold Spring Harbor, N.Y., 2014).

Example 1 Construction of Recombinant HVT Vectors Expressing Two Genes

Example 1.1 Construction of Recombinant vHVT309 Expressing IBDV-VP2 and NDV-F The objective of the study is to construct a recombinant HVT in which an expression cassette containing a mouse cytomegalovirus promoter (mCMV), a gene encoding an infectious bursal disease virus viral protein 2 (VP2), Simian virus 40 poly A tail (SV40 poly A), Simian virus 40 promoter (SV40 promoter), a gene encoding a Newcastle disease virus fusion protein (NDV-F) and synthetic poly A tail (syn poly A tail) is integrated in the intergenic site 1 (IG1).

The parental virus used in the construct is vHVT13 (an HVT vector expressing the IBDV VP2 gene, active ingredient of Merial's VAXXITEK® (HVT+IBD) Vaccine, also known as vHVT17 in U.S. Pat. No. 5,980,906). The vHVT13 vector contains an expression cassette composed of mCMV IE promoter (SEQ ID NO:6), IBDV VP2 gene (SEQ ID NO:1 encoding SEQ ID NO:2), and SV40 poly A tail (SEQ ID NO:8) inserted into the IG1 insertion site. A Newcastle disease virus Fusion Protein (NDV-F) corresponding to genotype VIId sequence was chemically synthesized and codon optimized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2, and SV40 promoter was used for NDV-F. The insertion locus is intergenic site 1 (IG1) in HVT (FIG. 2). Donor plasmid pFSV40VP2 (an insertion plasmid containing the VP2/SV40 poly A and flanking arm of IG1+SV40 promoter+NDV-F+synthetic poly A) was constructed as described below. Chicken embryo fibroblast cells (CEF) were used for in vitro recombination.

Donor Plasmid Construction

Synthetic DNA in pUC57 containing the IBDV VP2 gene (SEQ ID NO:1 encoding SEQ ID NO:2), SV40 poly A tail (SEQ ID NO:8), SV40 promoter (SEQ ID NO:7), NDV-F gene (SEQ ID NO:3 encoding SEQ ID NO:5), and synthetic poly A tail (SEQ ID NO:9) was synthesized by GenScript (FIG. 3). The plasmid, pFSV40VP2 was transformed using Top10 Oneshot kit (cat #C404002, Invitrogen) and a large scale culture was grown and plasmid extraction was done using Qiagens Maxi Prep kit. Transient expression of the maxi prep was verified using Fugene Transfection Reagent in Chicken Embryo Fibroblast Cells (CEF's) and chicken polyclonal sera against NDV.

Recombinant Generation

A standard homologous recombination procedure was followed by co-electroporation of secondary CEF cells using pFSV40VP2 plasmid and viral DNA isolated from vHVT13 Vaccine. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 4 days. The cells grown in the 96-well plate were then duplicated into two 96-well plates and incubated for 3 more days. One set of 96-well plates was used for IFA using chicken polyclonal sera against NDV-F to identify positive wells containing recombinants and another set of 96-well plates was used for recovering the infected cells from the positive wells.

The recombinant viral purification methods were performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock, 5-20 ul were removed and mixed with $1\times10^7$ CEFs in 10 ml DMEM+2% FBS and aliquoted onto a new 96-well plate to have single virus plaques per well. The 96-well plates were duplicated after 5 days of incubation and wells that contained plaques were tested for the presence of double recombinant and absence of vHVT13 parental virus by IFA and PCR. Again the wells that appeared to have more recombinant virus, by comparing the PCR banding results, were harvested and adjusted to 1 ml and aliquoted onto new 96-well plates. After two rounds of purification of virus infected cells, recombinant virus expressing NDV-F protein was isolated and the purity of the recombinant virus was tested by IFA and PCR to confirm the absence of parental virus.

Analysis of Recombinant by PCR

Figure 4:
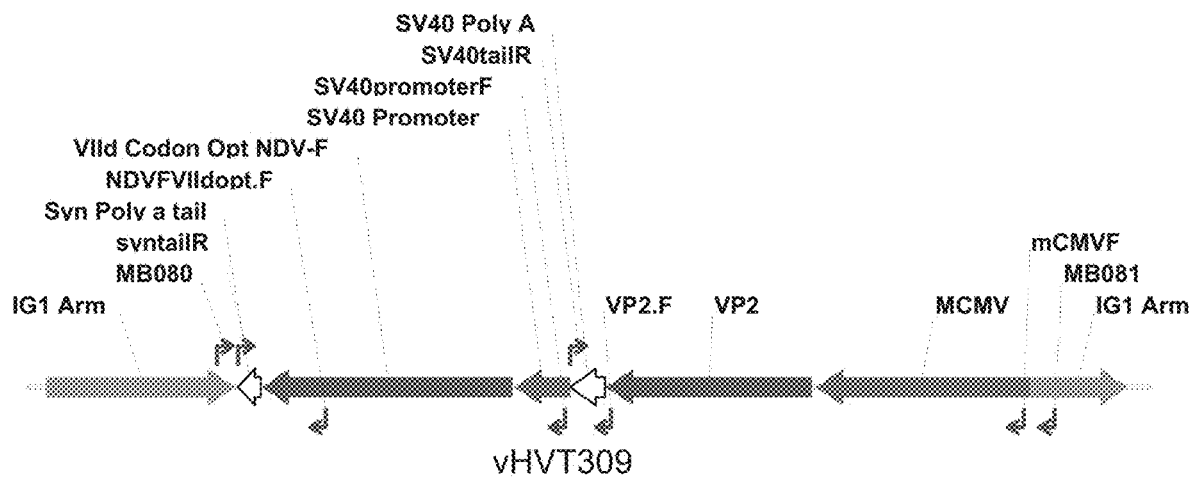
FIG. 4 depicts schematic representation of primer binding sites for vHVT309.

DNA was extracted from a stock virus by phenol/chloroform extraction, ethanol precipitation, and resuspended in 20 mM HEPES. PCR primers (Table 1) were designed to specifically identify the IBDV-VP2 and NDV-F VIId gene, the promoters, the poly As, as well as, the purity of the recombinant virus from Vaxxitek parental virus. The locations of the primer binding sites are shown in FIG. 4. PCR was performed using 200 μg of DNA template along with the specified primer pairs indicted in Table 1. PCR cycling conditions are as follows: 94° C. —2 min; 30 cycles of 94° C. —30 sec, 60° C. —45 sec, 68° C. —3 min (5 min for MB080+MB081 primer set); 68° C. —5 min (7 min for MB080+MB081 primer set).

TABLE 1

Expected PCR bands using specific primer sets

| Primer set | Vaxxitek | vHVT309 |
|---|---|---|
| MB080 + MB081 | 3350 | 5577 |
| MB010 + NDVFVIIdopt.F | — | 737 |
| MB080 + VP2.F | 405 | 2632 |
| SV40tailR + mCMVF | 3021 | 3021 |
| syntailR + SV40promoterF | — | 2184 |

Expression Analysis

For immunofluorescence testing, the recombinant material was diluted 1:100 in media. Approximately 50 µl of the diluted virus was added to 20 ml of DMEM+2% FBS with $2\times10^7$ CEFs and then aliquoted onto two 96 well plates (100 µl/well). The plates were incubated for 4 days at 37° C.+5% $CO_2$ until viral plaques were visible. The plates were fixed with 95% ice-cold acetone for three minutes, allowed to air dry for ten minutes and washed three times with water. Dual immunofluorescent staining was performed for plate #1 using chicken anti-sera against Newcastle Disease virus (NDV Pab) (lot #C0117A, Charles Rivers Laboratories) at 1:500 and HVT L78 monoclonal antibody (HVT Mab) (Lee et al. 1983, J. Immunol. 130 (2) 1003-6; Merial batch) at 1:3000 and the plate was incubated at 37° C. for 1 hour. Dual Immunofluorescent was performed for plate #2 using chicken anti-sera against Infectious Bursal Disease virus (IBDV Pab) at 1:500 (lot #G0117, Charles Rivers Laboratories) and HVT L78 monoclonal antibody (HVT Mab) (Merial) at 1:3000 and the plate was incubated at 37° C. for 1 hour. After one hour incubation, the plates were washed three times with PBS. To both plate #1 and #2 FITC labeled anti-chicken IgG (cat #F8888, Sigma) at 1:500 and TRITC labeled Alex Fluor donkey anti-mouse (cat #A10037, Invitrogen) at 1:300 was added. Again the plates were incubated at 37° C. for 1 hour. After one hour incubation the cells were rinsed three times with PBS and visualized with a fluorescent microscope using fluorescein isothiocyanate (FITC) filter and tetramethyl rhodamine iso-thiocyanate (TRITC) filter.

Results

The nucleotide and amino acid sequences of the donor plasmid pFSV40VP2 are assigned SEQ ID NO as shown in FIG. 1.

Recombinant Generation and Expression Analyses

Genomic DNA of vHVT13 virus was co-electroporated with pFSV40VP2 donor plasmid to generate recombinant using homologous recombination technique. Recombinant virus was separated from parental Vaxxitek virus by immunofluorescent positive well selection and PCR screening in multiple rounds of plaque purification. A plaque purified recombinant virus expressing the NDV-F protein, designated vHVT309, was scaled up from tissue culture flasks to $5\times850$ cm² roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of $1.5\times10^5$ pfu/ml was obtained for vHVT309.

Dual immunofluorescent staining was performed using chicken anti-sera (Pab) at 1:500 and HVT L78 monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with HVT. All examined HVT TRITC positive plaques of vHVT309 were found to express NDV-F and IBDV-VP2 proteins.

PCR Analysis of vHVT309

Figure 5:
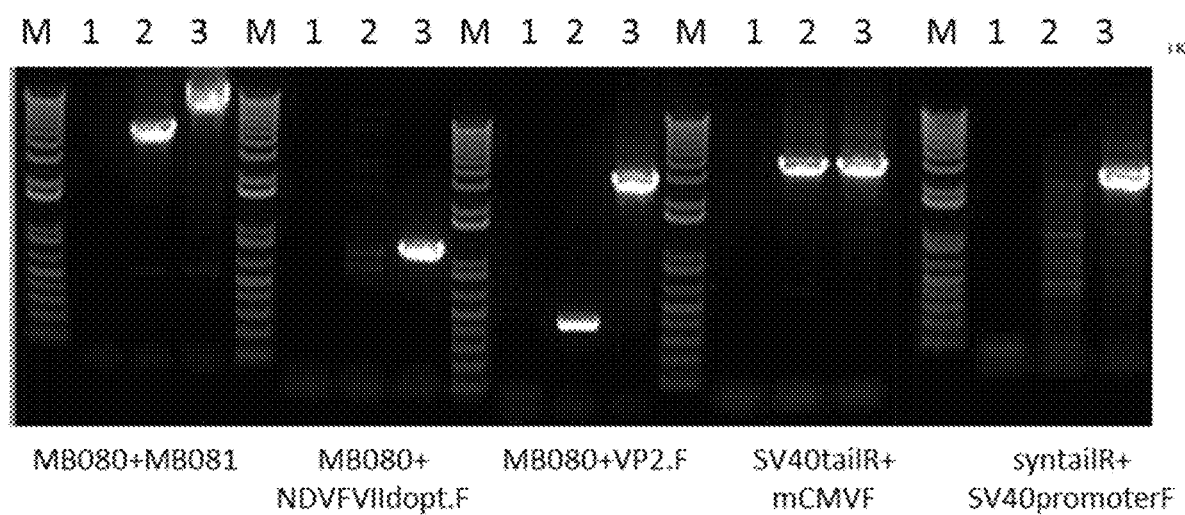
FIG. 5 depicts PCR identity result of vHVT309.

Purity of recombinant virus was verified by PCR using primer pairs that are specific to the HVT flanking arms, the promoters, the NDV-F and IBDV-VP2 genes, and the poly A tails. The PCR results demonstrate that recombinant virus vHVT309 carries the intended expression cassette and the virus stock is free from detectable amounts of parental Vaxxitek virus (Table 1 and FIG. 5).

Conclusion

Based on PCR testing and immunofluorescence analysis, vHVT309 is a recombinant virus containing an IBDV-VP2 gene under the control of mCMV promoter and a NDV-F gene under the control of an SV40 promoter. The newly generated vHVT309 is free of any detectable parental vHVT13 virus.

Example 1.2 Construction of Recombinant vHVT310 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding a Newcastle Disease virus fusion protein (NDV-F), and Simian virus 40 poly A tail (SV40 poly A) is integrated in the intergenic site 1 (IG1) (FIG. 2).

The parental virus used in the construct is vHVT13. A Newcastle disease virus Fusion Protein (NDV-F) corresponding to genotype VIId sequence was chemically synthesized and codon optimized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). IRES, an RNA sequence derived from Encephalomyocarditis virus (EMCV), that allows the initiation of translation within an mRNA immediately downstream from where the IRES is located, was inserted at the end of the VP2 gene to initiate translation of a downstream NDV-F gene. This was the first time that IRES was used in an HVT vector.

The insertion locus is intergenic site 1 (IG1) in HVT (FIG. 2). Donor plasmid pFIRESVP2 (an insertion plasmid containing the VP2 gene+IRES+NDV-F and SV40 poly A/flanking arm of IG1) was constructed as described below. Chicken embryo fibroblast cells (CEF) were used for in vitro recombination.

Figure 6:
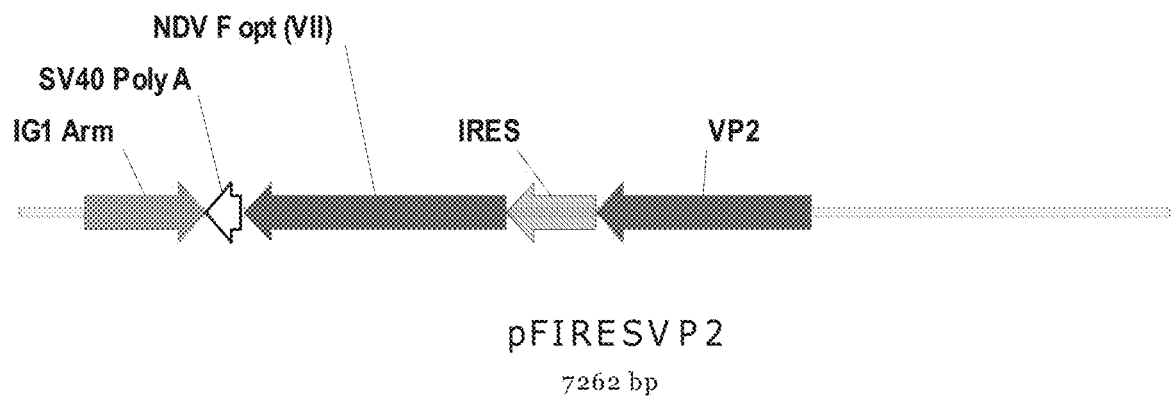
FIG. 6 depicts pFIRESVP2 plasmid map.

Donor Plasmid Construction:

Synthetic DNA in pUC57 containing the IBDV VP2 gene (SEQ ID NO:1) encoding SEQ ID NO:2), IRES (SEQ ID NO:10), NDV-F gene (SEQ ID NO:3) encoding SEQ ID NO:5), and SV40 poly A tail (SEQ ID NO:8) was synthesized by GeneScript (FIG. 6). The plasmid, pFIRESVP2 was transformed using Top10 Oneshot kit (cat #C404002, Invitrogen) and a large scale culture was grown and plasmid extraction was done using Qiagens Maxi Prep kit.

Recombinant Generation

The homologous recombination procedure as described in Example 1.1 was followed to make recombinant vHVT310.

Analysis of Recombinant by PCR

The PCR analysis procedure as described in Example 1.1 was performed to verify vHVT310.

Expression Analysis

The expression analysis described in Example 1.1 was performed to analyze the expression of vHVT310.

Results

The nucleotide and amino acid sequence of the donor plasmid pFIRESVP2 are assigned SEQ ID NO as shown in FIG. 1.

Recombinant Generation and Expression Analyses

Genomic DNA of Vaxxitek virus was co-electroporated with pFIRESVP2 donor plasmid to generate recombinant virus using homologous recombination technique. Recombinant virus was separated from parental vHVT13 virus by immunofluorescent positive well selection and PCR screening in multiple rounds of plaque purification. A plaque purified recombinant virus expressing the NDV-F protein, designated vHVT310, was scaled up from tissue culture flasks to 5×850 cm² roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of $2.0 \times 10^6$ pfu/ml was obtained for vHVT310.

Dual Immunofluorescent staining was performed using chicken anti-sera (Pab) at 1:500 and HVT L78 monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with HVT. All examined HVT TRITC positive plaques of vHVT310 were found to express NDV-F and IBDV-VP2 proteins.

PCR Analysis of vHVT310

Figure 7:
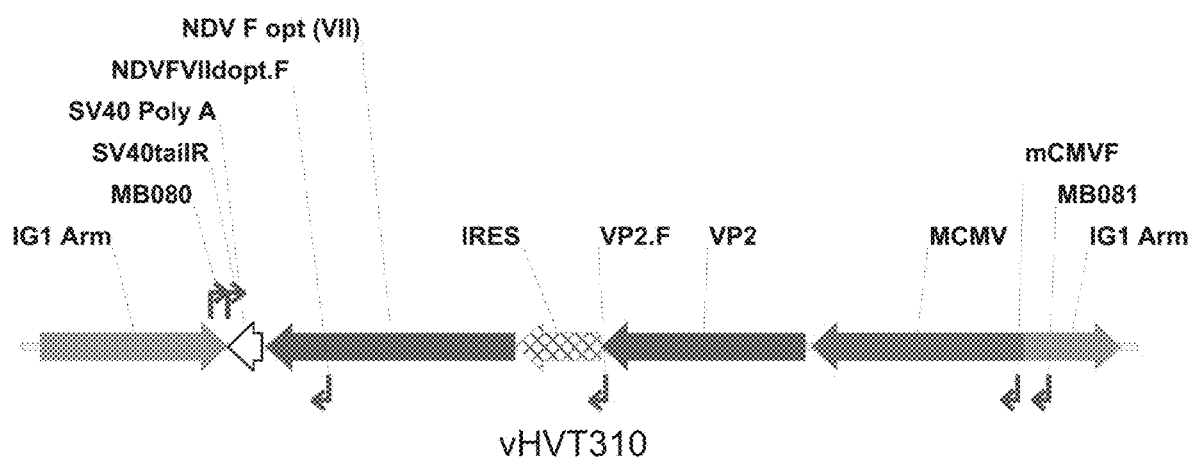
FIG. 7 depicts schematic representation of primer binding sites for vHVT310.

Purity of recombinant virus was verified by PCR using primer pairs that are specific to the HVT flanking arms, the promoter, the NDV-F and IBDV-VP2 genes, and the polyA tail. The PCR results demonstrate that recombinant virus vHVT310 carries the intended expression cassette and the virus stock is free from detectable amounts of parental Vaxxitek virus (Table 2 and FIG. 7-8).

TABLE 2

Expected PCR bands using specific primer sets

| Primer set | Vaxxitek | vHVT310 |
|---|---|---|
| MB080 + MB081 | 3350 | 5586 |
| MB080 + NDVFVlldopt.F | — | 798 |
| MB080 + VP2.F | 405 | 2641 |
| SV40tailR + mCMVF | 3021 | 5257 |

Conclusion

Based on PCR testing and immunofluorescence analysis, vHVT310 is a recombinant virus containing an IBDV-VP2 and NDV-F gene under the control of mCMV promoter, where the translation of NDV-F gene is initiated by IRES from EMCV. The newly generated recombinant vHVT310 is free of any detectable parental vHVT13 virus.

Example 1.3 Construction of Recombinant vHVT311 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), self-cleaving porcine teschovirus-1 2A peptide (P2A), a gene encoding a Newcastle Disease virus fusion protein (NDV-F), and Simian virus 40 poly A tail (SV40 poly A) is integrated in the intergenic site 1 (IG1) (FIG. 2).

The parental virus used in the construct is vHVT13 (an HVT vector expressing the IBDV VP2 gene, Merial's VAXXITEK® (HVT+IBD) Vaccine). The polynucleotide corresponding to wild-type genotype VIId Newcastle disease virus Fusion Protein (NDV-F) sequence was chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). A self-cleaving porcine teschovirus-1 2A peptide (P2A) that allows co-translational 'cleavage' of the upstream and downstream genes, VP2 and F, respectively from a single promoter mCMV, was inserted at the end of the VP2 gene. This is the first time that P2A was used in HVT vectors.

The insertion locus is intergenic site 1 (IG1) in HVT (FIG. 2). Donor plasmid pFP2AVP2 (an insertion plasmid containing the VP2+P2A+NDV-F and SV40 poly A/flanking arm of IG1) was constructed as described below. Chicken embryo fibroblast cells (CEF) were used for in vitro recombination.

Donor Plasmid Construction

Figure 9:
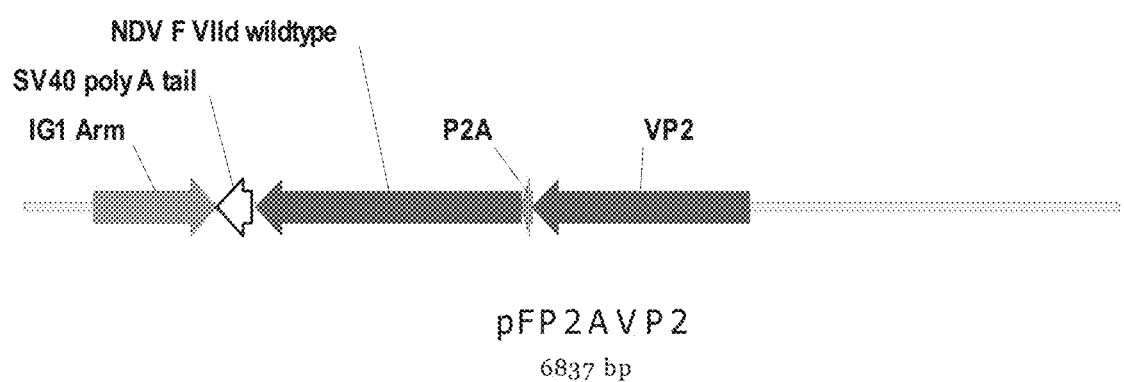
FIG. 9 depicts pFP2AVP2 plasmid map.

Synthetic DNA in pUC57 containing the IBDV VP2 gene (SEQ ID NO:1 encoding SEQ ID NO:2), P2A encoding DNA (SEQ ID NO:11), NDV-F gene (SEQ ID NO:4 encoding SEQ ID NO:5), and SV40 poly A tail (SEQ ID NO:8) was synthesized by GeneScript (FIG. 9). The plasmid, pFP2AVP2 was transformed using Top10 Oneshot kit (cat #C404002, Invitrogen) and a large scale culture was grown and plasmid extraction was done using Qiagens Maxi Prep kit.

Recombinant Generation

The homologous recombination procedure as described in Example 1.1 was followed to make recombinant vHVT311.

Analysis of Recombinant by PCR

The PCR analysis procedure as described in Example 1.1 was performed to verify vHVT311.

Expression Analysis

The expression analysis described in Example 1.1 was performed to analyze the expression of vHVT311.

Results

The nucleotide and amino acid sequences of the donor plasmid pFP2AVP2 are assigned SEQ ID NO as shown in FIG. 1.

Recombinant Generation and Expression Analyses

Genomic DNA of Vaxxitek virus was co-electroporated with pFP2AVP2 donor plasmid to generate recombinant virus using homologous recombination technique. Recombinant virus was separated from parental Vaxxitek virus by immunofluorescent positive well selection and PCR screening in multiple rounds of plaque purification. A plaque purified recombinant virus expressing the NDV-F protein, designated vHVT311, was scaled up from tissue culture flasks to 5×850 cm² roller bottles. After about 72 hrs post infection the infected CEFs were harvested. Aliquots were frozen in liquid nitrogen, each aliquot contained 10% FBS and 10% DMSO. Titrations were performed in triplicate on CEFs and a titer of $2.5 \times 10^6$ pfu/ml was obtained for vHVT311.

Dual Immunofluorescents was performed using chicken anti-sera (Pab) at 1:500 and a monoclonal antibody (Mab) at 1:3000 followed by a FITC labeled anti-chicken IgG at 1:500 and TRITC labeled Alex Fluor donkey anti-mouse at 1:300. Plate #1 compares the expression of Newcastle Disease virus with HVT and plate #2 compares the expression of Infectious Bursal Disease virus with Newcastle Disease virus. All examined HVT TRITC positive plaques of vHVT311 were found to express NDV-F and all NDV TRITC positive plaques were found to express IBDV-VP2 proteins.

PCR Analysis of vHVT311

Purity of recombinant virus was verified by PCR using primer pairs that are specific to the HVT flanking arms, the promoter, the NDV-F and IBDV-VP2 genes, and the poly A tail. The PCR results demonstrate that recombinant virus vHVT311 carries the intended expression cassette and the virus stock is free from detectable amounts of parental Vaxxitek virus (Table 3 and FIG. 10-11).

TABLE 3

Expected PCR bands using specific primer sets

| Primer set | Vaxxitek | vHVT311 |
|---|---|---|
| MB080 + MB081 | 3350 | 5101 |
| MB080 + NDVFVlldwt.F | — | 840 |
| MB080 + VP2.F | 405 | 2156 |
| SV40tailR + mCMVF | 3021 | 4772 |

Conclusion

Based on PCR testing and immunofluorescence analysis, vHVT311 is a recombinant virus containing an IBDV-VP2 and NDV-F gene under the control of mCMV promoter in which the 2A peptide-mediated cleavage result in co-expression of VP2 and F proteins. The newly generated recombinant vHVT311 is free of any detectable parental vHVT13 virus.

Example 1.4 Construction of Recombinant vHVT317 Expressing IBDV-VP2 and ILTV-gD

The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding an Infectious Laryngotracheitis glycoprotein D protein (ILTV-gD), and Simian virus 40 poly A tail (SV40 poly A) is integrated in the intergenic site 1 (IG1) (FIG. 2).

The parental virus used in the construct is vHVT13. An Infectious Laryngotracheitis virus glycoprotein D (ILTV gD) sequence which was chemically synthesized (GenScript) was used in the construct. Mouse CMV IE promoter was used for IBD-VP2 (in the parental vHVT13 virus). An RNA sequence (IRES) derived from Encephalomyocarditis virus (EMCV), that allows the initiation of translation within an mRNA immediately downstream from where the IRES is located, was inserted at the end of the VP2 gene to initiate translation of a downstream ILTV-gD gene.

The insertion locus is intergenic site 1 (IG1) in HVT (FIG. 2). Donor plasmid pVP2IRESgD (an insertion plasmid containing the VP2 gene+IRES+ILTV-gD and SV40 poly A/flanking arm of IG1) was constructed as described below. Chicken embryo fibroblast cells (CEF) were used for in vitro recombination.

Donor Plasmid Construction

Figure 12:
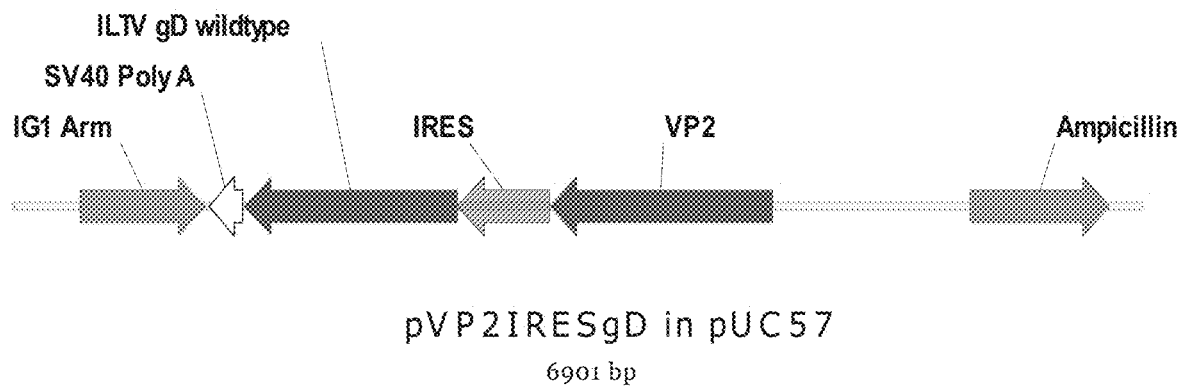
FIG. 12 depicts pVP2IRESgD plasmid map.

Synthetic DNA in pUC57 containing the IBDV VP2 gene (SEQ ID NO:1 encoding SEQ ID NO:2), IRES (SEQ ID NO:10), ILTV-gD gene (SEQ ID NO:16 encoding SEQ ID NO:17), and SV40 poly A tail (SEQ ID NO:8) was synthesized by GenScript. The plasmid, pFIRESVP2 was transformed into dcm-/dam-competent cells (New England Biolabs, cat #C2925I) then digested with HindIII/SalI. The 5 kb fragment was gel extracted. A synthetic DNA in pUC57 containing a partial IRES, ILTV-gD wildtype, and SV40 poly A tail was synthesized by GenScript. The plasmid, SaI-Fse gD-IRES was digested with HindIII/SalI. The 1.9 kb fragment was gel extracted. The two fragments were ligated and transformed using Top10 Oneshot kit (cat #C404002, Invitrogen). Colonies were screen by HindIII/SbfI for the correct pattern. The final donor plasmid was sequenced verified and designated pVP2IRESgD (see FIG. 12).

Recombinant Generation

The homologous recombination procedure as described in Example 1.1 was followed to make recombinant vHVT317.

Analysis of Recombinant by PCR

The PCR analysis procedure as described in Example 1.1 was performed to verify vHVT317.

Expression Analysis

The expression analysis described in Example 1.1 was performed to analyze the expression of vHVT317.

Results

The nucleotide and amino acid sequence of the donor plasmid pVP2IRESgD are assigned SEQ ID NO as shown in FIG. 1.

Recombinant Generation and Expression Analyses

Dual Immunofluorescents was performed using chicken anti-sera (Polyclonal antibody) at 1:500 and a monoclonal antibody (Mab) at 1:3000 followed by a FITC labeled anti-chicken IgG at 1:500 and TRITC labeled Alex Fluor donkey anti-mouse at 1:300. All examined plaques of vHVT317 were found to express IBDV-VP2 proteins compared to HVT positive plaques and all and plaques were found to express ILTV-gD proteins when compared to IBDV positive plaques.

PCR Analysis of vHVT317

Figure 13:
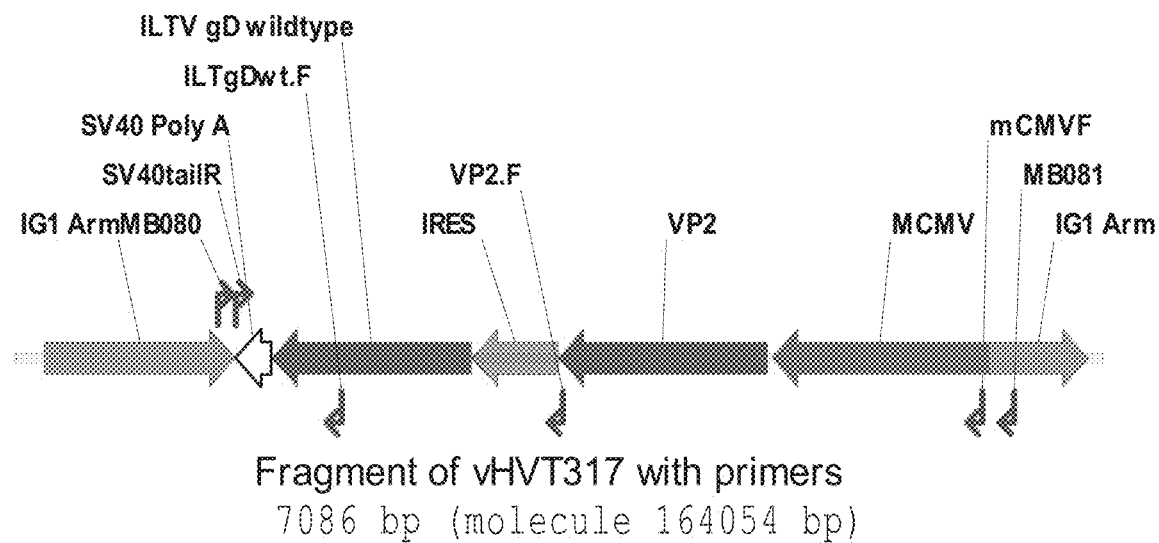
FIG. 13 depicts schematic representation of primer binding sites for vHVT317.

Purity of recombinant virus was verified by PCR using primer pairs that are specific to the HVT flanking arms, the promoter, the ILTV-gD and IBDV-VP2 genes, and the poly A tail. The PCR results demonstrate that recombinant virus vHVT317 carries the intended expression cassette and the virus stock is free from detectable amounts of parental Vaxxitek virus (Table 4 and FIG. 13-14).

TABLE 4

Expected PCR bands using specific primer sets

| Primer set | Vaxxitek | vHVT317 |
|---|---|---|
| MB080 + MB081 | 3350 | 5101 |
| MB080 + ILTgDwt.F | — | 825 |
| MB080 + VP2.F | 405 | 2272 |
| SV40tailR + mCMVF | 3021 | 4888 |

Conclusion

Based on PCR testing and immunofluorescence analysis, vHVT317 is a recombinant virus containing an IBDV-VP2 and ILTV-gD gene under the control of mCMV promoter, where the translation of ILTV-gD gene is initiated by IRES from EMCV. The newly generated recombinant vHVT317 is free of any detectable parental vHVT13 virus.

Example 1.5 Construction of Recombinant vHVT313 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), Simian virus 40 poly A tail (SV40 poly A), Simian virus 40 promoter (SV40 promoter), a gene encoding a wildtype Newcastle disease virus fusion protein (NDV-F) and synthetic poly A tail (syn poly A tail) is integrated in the intergenic site 1 (IG1) (FIG. 2).

The parental virus used in the construct is vHVT13. A Newcastle disease virus Fusion Protein (NDV-F) corresponding to genotype VIId wildtype sequence chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter for IBD-VP2 (in the parental Vaxxitek virus) and SV40 promoter for NDV-F were used.

The insertion locus is intergenic site 1 (IG1) (FIG. 2). Donor plasmid pFwtSV40VP2 (an insertion plasmid containing the VP2/SV40 poly A and flanking arm of IG1+SV40 promoter+NDV-F+synthetic poly A) was constructed as described below. Chicken embryo fibroblast cells (CEF) were used for in vitro recombination.

Donor Plasmid Construction

Synthetic DNA in pUC57 containing the IBDV VP2 gene (SEQ ID NO:1 encoding SEQ ID NO:2), SV40 poly A tail (SEQ ID NO:8), SV40 promoter (SEQ ID NO:7), NDV-F gene (SEQ ID NO:4 encoding SEQ ID NO:5), and synthetic poly A tail (SEQ ID NO:9) was synthesized by GeneScript.

Figure 15:
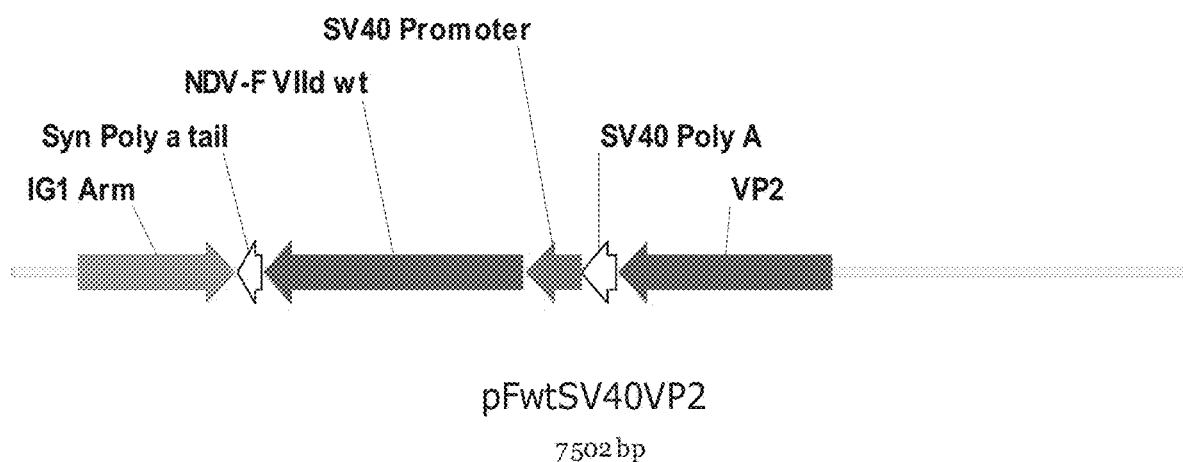
FIG. 15 depicts pFwtSV40VP2 plasmid map.

The plasmid, pFSV40VP2 was then digested with SbfI/AvrII and the 5.6 kb fragment was gel extracted. A plasmid, pHM103NDVFwtsyn was also digested with SbfI/AvrII and the 1.9 kb fragment was gel extracted. The fragments were then ligated together and transformed using Top10 Oneshot kit (cat #C404002, Invitrogen). Colonies were screened with PstI for the correct pattern. Transient expression of the maxi prep was verified using Fugene Transfection Reagent in Chicken Embryo Fibroblast Cells (CEF's) and chicken polyclonal sera against NDV. The final donor plasmid was sequenced verified and designated pFwtSV40VP2 (see FIG. 15).

Recombinant Generation

The homologous recombination procedure as described in Example 1.1 was followed to make recombinant vHVT313.

Analysis of Recombinant by PCR

The PCR analysis procedure as described in Example 1.1 was performed to verify vHVT313.

Expression Analysis

The expression analysis described in Example 1.1 was performed to analyze the expression of vHVT313.

Results

The nucleotide and amino acid sequence of the donor plasmid pFwtSV40VP2 are assigned SEQ ID NO as shown in FIG. 1.

Recombinant Generation and Expression Analyses

Dual Immunofluorescents was performed using chicken anti-sera (Pab) and an anti-HVT monoclonal antibody (Mab) followed by a FITC labeled anti-chicken IgG and TRITC labeled Alex Fluor donkey anti-mouse. All examined TRITC positive plaques of vHVT313 were found to express NDV-F and IBDV-VP2 proteins.

PCR Analysis of vHVT313

Figure 17:
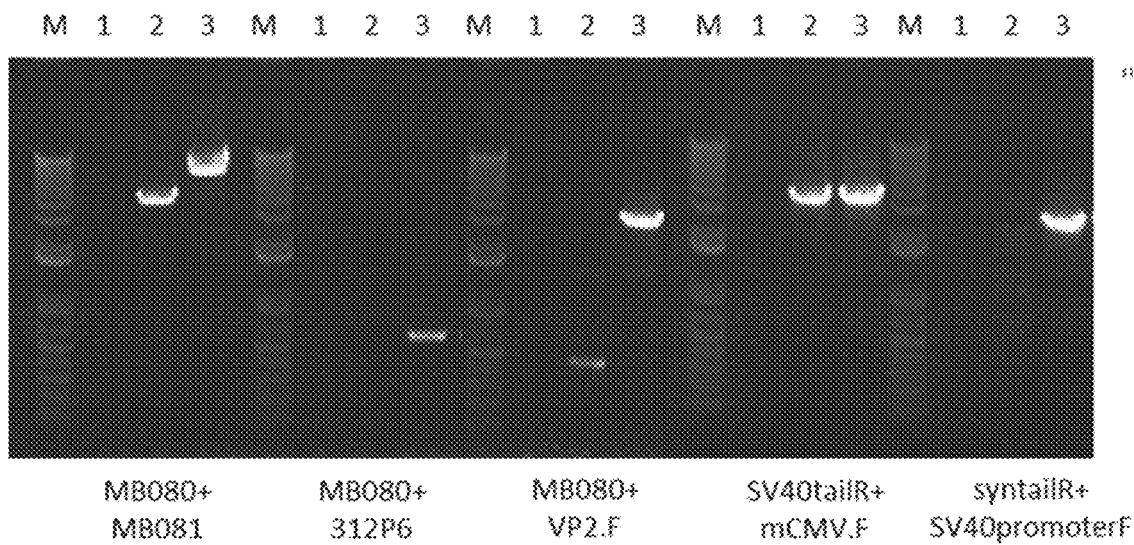
FIG. 17 depicts PCR identity result of vHVT313.

Purity of recombinant virus was verified by PCR using primer pairs that are specific to the HVT flanking arms, the promoters, the NDV-F and IBDV-VP2 genes, and the poly A tails. The PCR results demonstrate that recombinant virus vHVT313 carries the intended expression cassette and the virus stock is free from detectable amounts of parental Vaxxitek virus (Table 5 and FIG. 16-17).

TABLE 5

| Expected PCR bands using specific primer sets | | |
|---|---|---|
| Primer set | Vaxxitek | vHVT313 |
| MB080 + MB081 | 3350 | 5574 |
| MB080 + 312P6 | — | 556 |

TABLE 5-continued

| Expected PCR bands using specific primer sets | | |
|---|---|---|
| Primer set | Vaxxitek | vHVT313 |
| MB080 + VP2.F | 405 | 2629 |
| SV40tailR + mCMVF | 3021 | 3021 |
| SyntailR + SV40promoterF | — | 2181 |

Conclusion

Based on PCR testing and immunofluorescence analysis, vHVT313 is a recombinant virus containing an IBDV-VP2 gene under the control of mCMV promoter and a NDV-F wildtype gene under the control of an SV40 promoter. The newly generated vHVT313 is free of any detectable parental Vaxxitek virus.

Example 1.6 Construction of Recombinant vHVT316 Expressing IBDV-VP2 and NDV-F

The objective of the study is to construct a recombinant HVT in which an expression cassette containing a mouse cytomegalovirus promoter (mCMV), a gene encoding an infectious bursal disease virus viral protein 2 (VP2), internal ribosome entry site (IRES), a gene encoding a wildtype Newcastle Disease virus fusion protein (NDV-F), and Simian virus 40 poly A tail (SV40 poly A) is integrated in the IG1 locus (FIG. 2).

The parental virus used in the construct is vHVT13. A Newcastle disease virus Fusion Protein (NDV-F) corresponding to genotype VIId wildtype sequence chemically synthesized (GenScript). The F protein cleavage site of this synthetic gene was altered to match a lentogenic F cleavage site sequence and the resultant NDV-F gene sequence has 99% amino acid sequence identity to NDV-F sequence deposited in GenBank (AY337464). Mouse CMV IE promoter was used for IBD-VP2 (in the parental Vaxxitek virus). IRES was inserted at the end of the VP2 gene to initiate translation of a downstream NDV-F gene.

The insertion locus is IG1 (FIG. 2). Donor plasmid pVP2IRESFwt (an insertion plasmid containing the VP2 gene+IRES+NDV-F and SV40 poly A/flanking arm of IG1) was constructed as described below. Chicken embryo fibroblast cells (CEF) were used for in vitro recombination.

Donor Plasmid Construction

Figure 18:
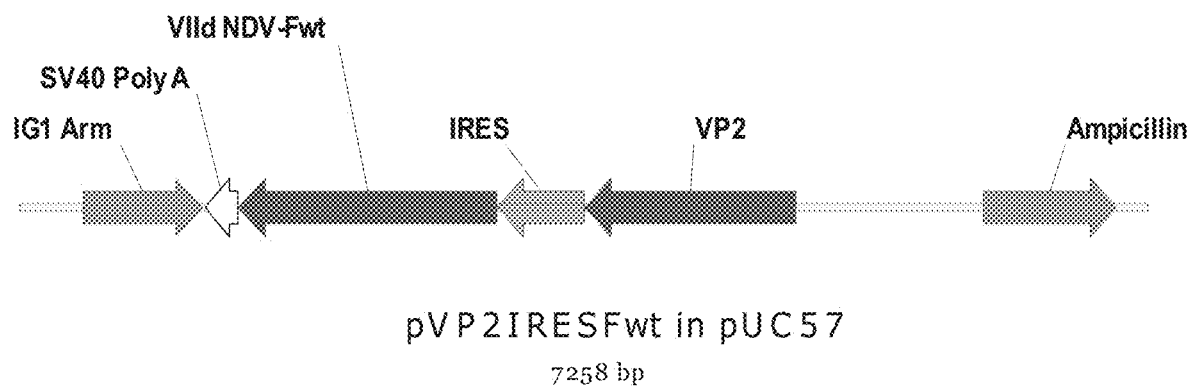
FIG. 18 depicts pVP2IRESFwt plasmid map.

Synthetic DNA in pUC57 containing the IBDV VP2 gene (SEQ ID NO:1 encoding SEQ ID NO:2), IRES(SEQ ID NO:10), NDV-F gene (SEQ ID NO:4 encoding SEQ ID NO:5), and SV40 poly A tail (SEQ ID NO:8), was synthesized by GeneScript. The plasmid, pFIRESVP2 was transformed into dcm-/dam-competent cells (New England Biolabs, cat #C2925I) then digested with HindIII/SalI. The 5 kb fragment was gel extracted. A synthetic DNA in pUC57 containing a partial IRES, NDV-F wildtype, and SV40 poly A tail was synthesized by GeneScript. The plasmid, Sal-Hind-Fwt+ was digested with HindIII/SalI. The 2.2 kb fragment was gel extracted. The two fragments were ligated and transformed using Top10 Oneshot kit (cat #C404002, Invitrogen). The final donor plasmid was sequenced verified and designated pVP2IRESFwt (see FIG. 18).

Recombinant Generation

The homologous recombination procedure as described in Example 1.1 was followed to make recombinant vHVT316.

Analysis of Recombinant by PCR

The PCR analysis procedure as described in Example 1.1 was performed to verify vHVT316.

Expression Analysis

The expression analysis described in Example 1.1 was performed to analyze the expression of vHVT316.

Results

The nucleotide and amino acid sequence of the donor plasmid pVP2IRESFwt are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT316 were found to express IBDV-VP2 proteins compared to HVT positive plaques and all and plaques were found to express IBDV-VP2 proteins when compared to NDV positive plaques.

PCR Analysis of vHVT316

Figure 20:
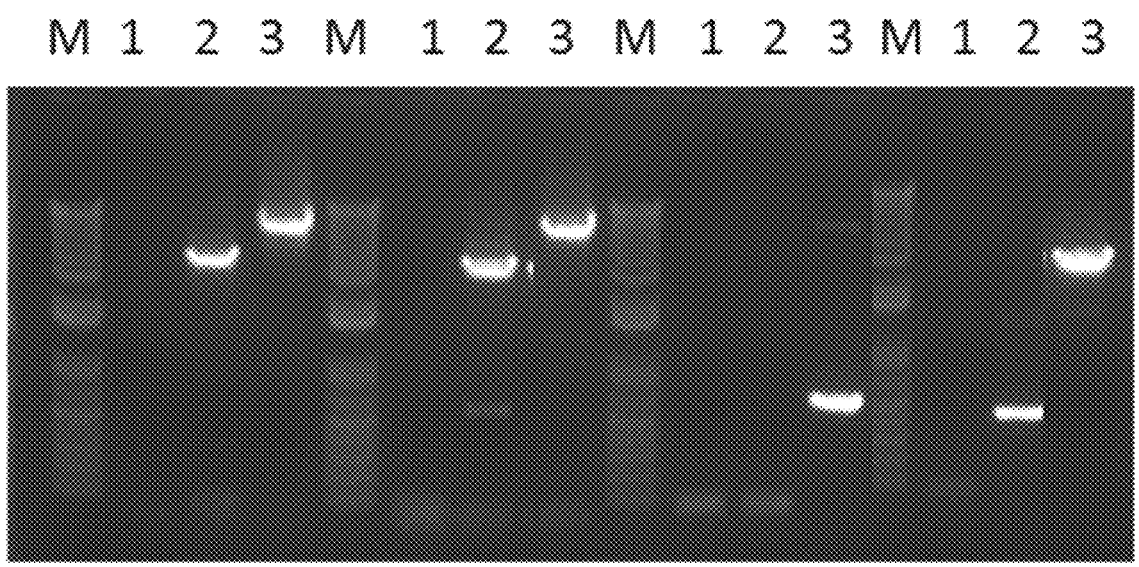
FIG. 20 depicts PCR identity result of vHVT316.

Purity of recombinant virus was verified by PCR using primer pairs that are specific to the HVT flanking arms, the promoter, the NDV-F and IBDV-VP2 genes, and the poly A tail. The PCR results demonstrate that recombinant virus vHVT316 carries the intended expression cassette and the virus stock is free from detectable amounts of parental Vaxxitek virus (Table 6 and FIG. 19-20).

TABLE 6

Expected PCR bands using specific primer sets

| Primer set | Vaxxitek | vHVT316 |
|---|---|---|
| MB080 + MB081 | 3350 | 5574 |
| MB080 + 312P6 | — | 604 |
| MB080 + VP2.F | 405 | 2629 |
| SV40tailR + mCMVF | 3021 | 5245 |

Conclusion

Based on PCR testing and immunofluorescence analysis, vHVT316 is a recombinant virus containing an IBDV-VP2 and NDV-F gene under the control of mCMV promoter, where the translation of NDV-F gene is initiated by IRES from EMCV. The newly generated recombinant vHVT316 is free of any detectable parental Vaxxitek virus.

Example 1.7 Construction of Recombinant vHVT407 Expressing IBDV-VP2 and ILTV-gD

The objective of the study is to construct a recombinant HVT in which an expression cassette containing an SV40 promoter, ILTV glycoprotein D, and synthetic poly A into the SORF3-US2 site of vHVT13.

Figure 22:
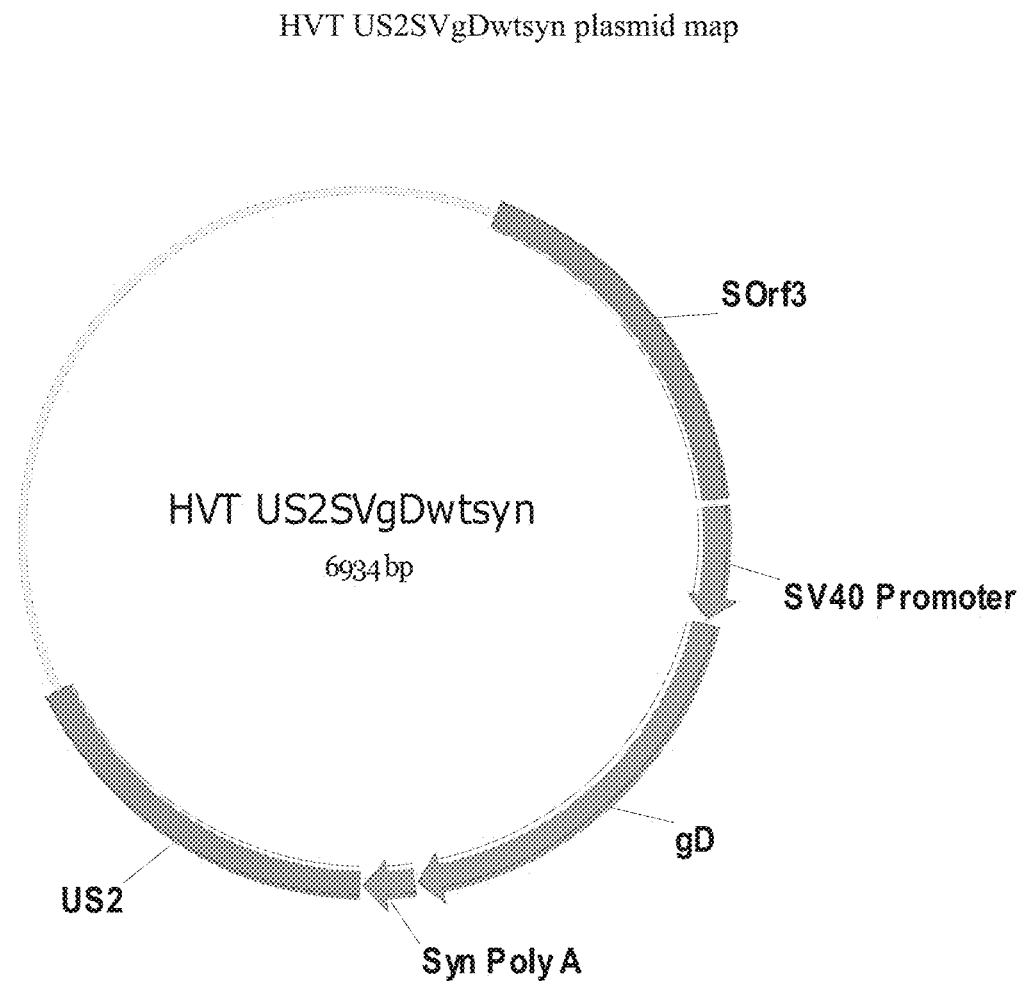

The parental virus used in the construct is vHVT13. An Infectious Laryngotracheitis virus glycoprotein D (ILTV gD) sequence which was chemically synthesized (GenScript) was used in the construct. SV40 promoter was used for ILTV gD. The insertion locus is SORF3-US2 for ILTV gD and IG1 for IBDV VP2 from vVHT13 (FIG. 2). Donor plasmid HVT US2SVgDwtsyn containing SORF3-US2 arms, SV40 promoter (SEQ ID NO:7), gene encoding ILTV wild-type gD (SEQ ID NO:16 encoding SEQ ID NO:17), and synthetic polyA (SEQ ID NO:9) was constructed (see FIG. 22). Chicken embryo fibroblast cells (CEF) were used for in vitro recombination.

Recombinant Generation

The homologous recombination procedure as described in Example 1.1 was followed to make recombinant vHVT407.

Analysis of Recombinant by PCR

The PCR analysis procedure as described in Example 1.1 was performed to verify vHVT407.

Expression Analysis

The expression analysis described in Example 1.1 was performed to analyze the expression of vHVT407.

Results

The nucleotide and amino acid sequence of the donor plasmid HVT US2SVgDwtsyn are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT407 were found to express IBDV-VP2 and ILTV gD proteins.

PCR Analysis of vHVT407

Purity of recombinant virus was verified by PCR using primer pairs that are specific to the HVT flanking arms, the promoter, the ILTV gD and IBDV-VP2 genes, and the poly A tail. The PCR results demonstrate that recombinant virus vHVT407 carries the intended expression cassette and the virus stock is free from detectable amounts of parental vHVT13 virus.

Conclusion

Based on PCR testing and immunofluorescence analysis, vHVT407 is a recombinant virus containing IBDV-VP2 and ILTV gD genes. The newly generated recombinant vHVT407 is free of any detectable parental vHVT13 virus.

Example 1.8 Construction of Recombinant vHVT308 Expressing NDV-F and ILTV-gD in Opposite Directions The objective of the study is to construct an insertion plasmid for the Intergenic region I site that will contain a Synthetic poly A tail, NDV F, SV40 promoter, HHV3gB promoter, ILTV gD, and SV40 poly A tail for homologous recombination into HVT FC126.

The parental virus used in the construct is HVT FC126. A synthetic Newcastle disease virus Fusion Protein (NDV-F) (SEQ ID NO:21 encoding SEQ ID NO:22) corresponding to genotype V sequence was chemically synthesized and codon optimized (GenScript). The F protein cleavage site of this synthetic gene was altered to match a lentogenic F cleavage site sequence. A synthetic wildtype ILTV glycoprotein D (SEQ ID NO:16 encoding SEQ ID NO:17) was chemically synthesized. Donor plasmid pHVTIG1gDCaFopt containing the HHV3gB promoter (Human Herpesvirus Type 3 glycoprotein B promoter) in the reverse orientation driving ILTV-gD+SV40 poly A tail, and SV40 promoter driving Newcastle fusion protein+synthetic poly A tail was constructed (see FIG. 23). Chicken embryo fibroblast cells (CEF) were used for in vitro recombination.

Recombinant Generation

The homologous recombination procedure as described in Example 1.1 was followed to make the recombinant vHVT308. Serial passaging was performed to pre-MSV+13.

Analysis of Recombinant by PCR

The PCR analysis procedure as described in Example 1.1 was performed to verify the recombinant vHVT308.

Expression Analysis

The expression analysis described in Example 1.1 was performed to analyze the expression of the recombinant vHVT308.

Results

The nucleotide and amino acid sequence of the donor plasmid pHVTIG1gDCaFopt are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined plaques of vHVT308 were found to express NDV-F and ILTV-gD proteins.

PCR Analysis of vHVT308

Figure 25:
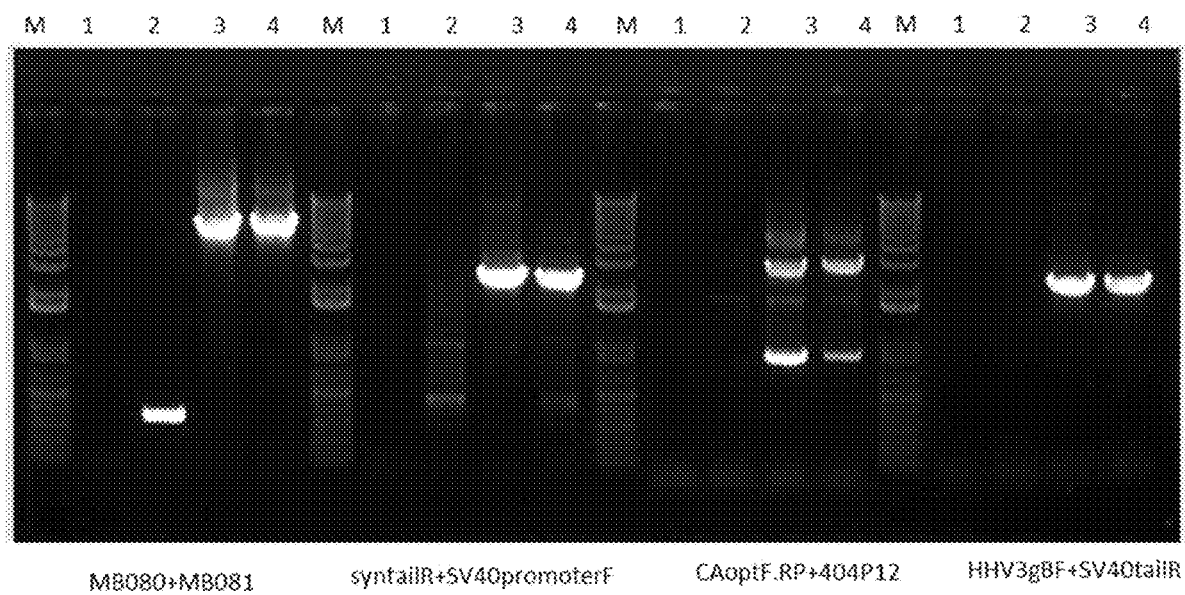
FIG. 25 depicts PCR identity result of vHVT308.

Purity of recombinant virus was verified by PCR using primer pairs that are specific to the HVT flanking arms, the promoters, the NDV-F and ILTV-gD genes, and the poly A tails. The PCR results demonstrate that recombinant virus vHVT308 carries the intended expression cassette and the virus stock is free from detectable amounts of parental HVT virus (Table 6.1 and FIGS. 24 and 25).

TABLE 6.1

Expected PCR bands using specific primer sets

| Primer set | HVTFC126 | vHVT308 |
|---|---|---|
| MB080 + MB081 | 323 bp | 4697 bp |
| syntailR + SV40promoterF | — | 2196 bp |
| CAoptF.RP + 404P12 | — | 2056 bp |
| HHV3gBF + SV40tailR | — | 2043 bp |

PCR reactions with all primer pairs resulted in the expected PCR products and banding patterns. As shown above, there is no evidence of parental HVT virus in vHVT308 and vHVT308 is stable at pre-MSV+13 passages.

Conclusion

Based on PCR testing and immunofluorescence analysis, vHVT308 is a recombinant HVT virus containing an NDV-F gene under the control of an SV40 promoter and an ILTV-gD gene under the control of an HHV3gB promoter. vHVT308 is free of any detectable parental HVT virus.

Example 1.9 Construction of Recombinant vHVT322 Expressing NDV-F and ILTV-gD

The objective of the study is to construct a recombinant HVT in which an expression cassette containing an mCMV promoter, Newcastle Disease virus fusion protein (NDV-F), internal ribosome entry site (IRES), Infectious Laryngotracheitis glycoprotein D (ILTV-gD), and Simian virus 40 poly A tail (SV40 poly A) will homologously recombine with the flanking arms in the intergenic region 1 (IG1) of vHVT13 (HVT+IBD).

The parental virus used in the construct is vHVT13. A Newcastle disease virus Fusion Protein (NDV-F) corresponding to the wildtype genotype VIId sequence (SEQ ID NO:4 encoding SEQ ID NO:5) was chemically synthesized (GenScript). The F protein cleavage site of this synthetic gene was altered to match a lentogenic F cleavage site sequence and the resultant NDV-F gene sequence has 99% nucleotide as well as amino acid sequence identity to NDV-F sequence deposited in GenBank (AY337464). A synthetic wildtype ILTV glycoprotein D (SEQ ID NO:16 encoding SEQ ID NO:17) was chemically synthesized. Donor plasmid_pFwtIRESgD contained the left flanking arm of IG1, mCMV (mouse CMV IE) promoter, NDV-F, IRES, ILTV-gD, SV40 poly A, and the right flanking arm of IG1 (see FIG. 26). Chicken embryo fibroblast cells (CEF) were used for in vitro recombination.

Recombinant Generation

The homologous recombination procedure as described in Example 1.1 was followed to make the recombinant vHVT322. Serial passaging was performed to pre-MSV+13.

Analysis of Recombinant by PCR

The PCR analysis procedure as described in Example 1.1 was performed to verify the recombinant vHVT322.

Expression Analysis

The expression analysis described in Example 1.1 was performed to analyze the expression of the recombinant vHVT322.

Results

The nucleotide and amino acid sequence of the donor plasmid pFwtIRESgD are assigned SEQ ID NO as shown in FIG. 1.

Recombinant Generation and Expression Analyses

Dual Immunofluorescent staining was performed using chicken anti-sera (Pab) and a monoclonal antibody (Mab) followed by a FITC labeled anti-chicken IgG and TRITC labeled Alex Fluor donkey anti-mouse. All examined TRITC positive plaques of vHVT322 were found to express NDV-F and ILTV-gD proteins.

PCR Analysis of vHVT322

Figure 28:
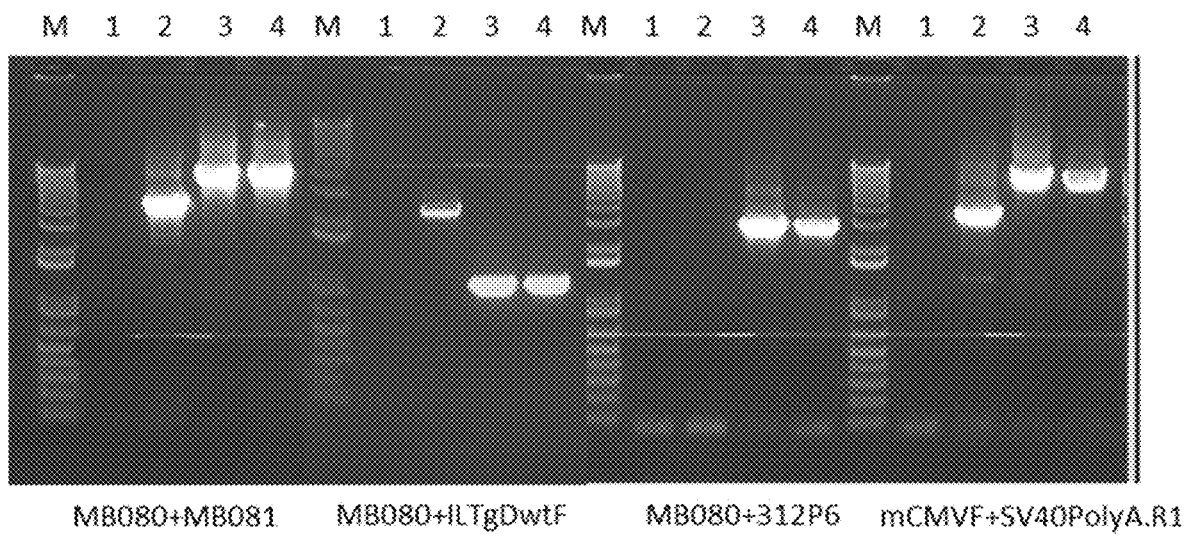
FIG. 28 depicts PCR identity result of vHVT322.

Purity of recombinant virus was verified by PCR using primer pairs that are specific to the HVT flanking arms, the promoter, the NDV-F and ILTV-gD genes, and the poly A tail. The PCR results demonstrate that recombinant virus vHVT322 carries the intended expression cassette and the virus stock is free from detectable amounts of parental vHVT13 (Table 6.2 and FIGS. 27 and 28).

TABLE 6.2

Expected PCR bands using specific primer sets

| Primer set | vHVT13 | vHVT322 |
|---|---|---|
| MB080 + MB081 | 3350 bp | 5804 bp |
| MB080 + ILTgDwtF | — | 1653 bp |
| MB080 + 312P6 | — | 2485 bp |
| mCMVF + SV40PolyA.R1 | 3021 bp | 5105 bp |

PCR reactions with all primer pairs resulted in the expected PCR products and banding patterns. As shown above, there is no evidence of parental vHVT13 virus in vHVT322.

Conclusion

Based on PCR testing and immunofluorescence analysis, vHVT322 is a recombinant HVT virus containing an NDV-F and ILTV-gD gene under the control of mCMV promoter. vHVT322 is free of any detectable parental vHVT13 virus.

Example 1.10 Construction of Recombinant vHVT406 Expressing ILT-gDwt

The objective of the study is to construct a recombinant HVT of which the SORF3-US2 site contains the SV40 promoter, Infectious Larygotracheitis gD, and synthetic poly A tail for homologous recombination into HVT FC126.

The parental virus used in the construct is HVT FC126. A synthetic Infectious Laryngotracheitis Virus (ILTV) wildtype glycoprotein D (gDwt) was chemically synthesized. Donor plasmid pHVTUS2SVgDwtsyn contained the SORF3 and US2 arms of HVT FC126, SV40 promoter, ILTV gDwt (SEQ ID NO:16 encoding SEQ ID NO:17) and synthetic poly A (see FIG. 29). Chicken embryo fibroblast cells (CEF) were used for in vitro recombination.

Recombinant Generation

The homologous recombination procedure as described in Example 1.1 was followed to make the recombinant vHVT406. Serial passaging was performed to pre-MSV+13 (x+12).

Analysis of Recombinant by PCR

The PCR analysis procedure as described in Example 1.1 was performed to verify the recombinant vHVT406.

Expression Analysis

The expression analysis described in Example 1.1 was performed to analyze the expression of the recombinant vHVT406.

Results

The nucleotide and amino acid sequence of the donor plasmid pHVTUS2SVgDwtsyn are assigned SEQ ID NO as shown in FIG. 1.

Recombinant Generation and Expression Analyses

Genomic DNA of HVT virus was co-electroporated with pHVTUS2SVgDwtsyn donor plasmid to generate recombinant HVT using homologous recombination technique. Recombinant virus was separated from parental HVT virus by immunofluorescent positive well selection and PCR screening in multiple rounds of plaque purification. A plaque purified recombinant HVT virus expressing the ILTV-gD protein was designated vHVT406.

Recombinant vHVT406 viral plaques were visualized using both the TRITC and FITC filters for the dual staining. The FITC showed the ILTV-gDwt expression and the TRITC showed the HVT expression. Because of the small wells of the 96 well plates, each well was recorded with the plaques first counted with the TRITC filter and then recounted with the FITC filter. A combined 600+ plaques were counted between the pre-MSV and pre-MSV+13 passage. All the plaques were positive for both the FITC and TRITC for both passages.

PCR Analysis of vHVT406

Figure 30:
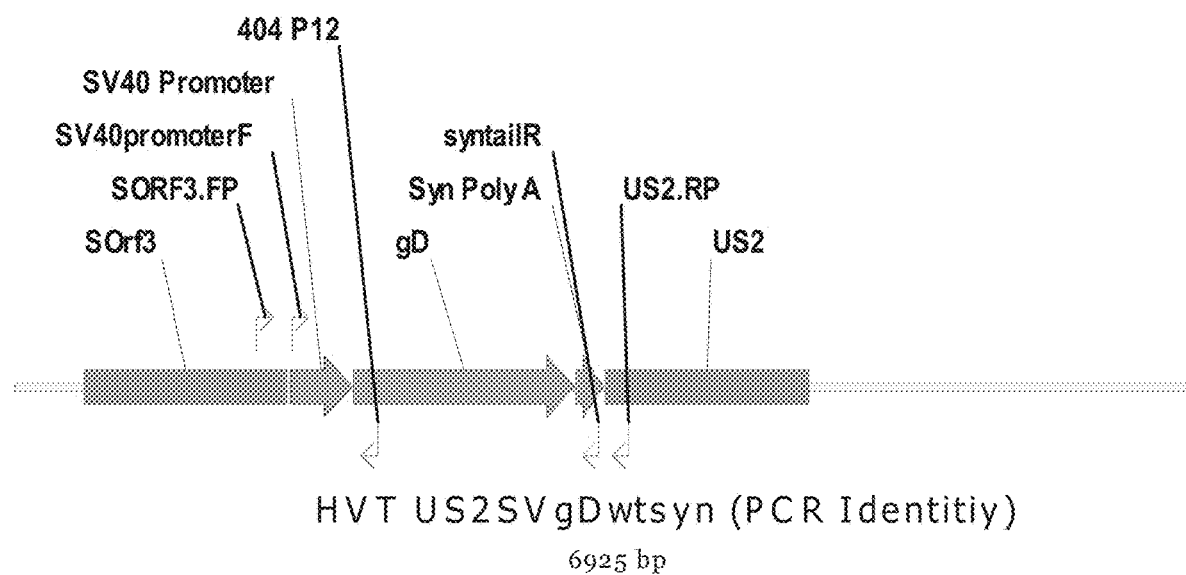
FIG. 30 depicts schematic representation of primer binding sites for vHVT406.
Figure 31:
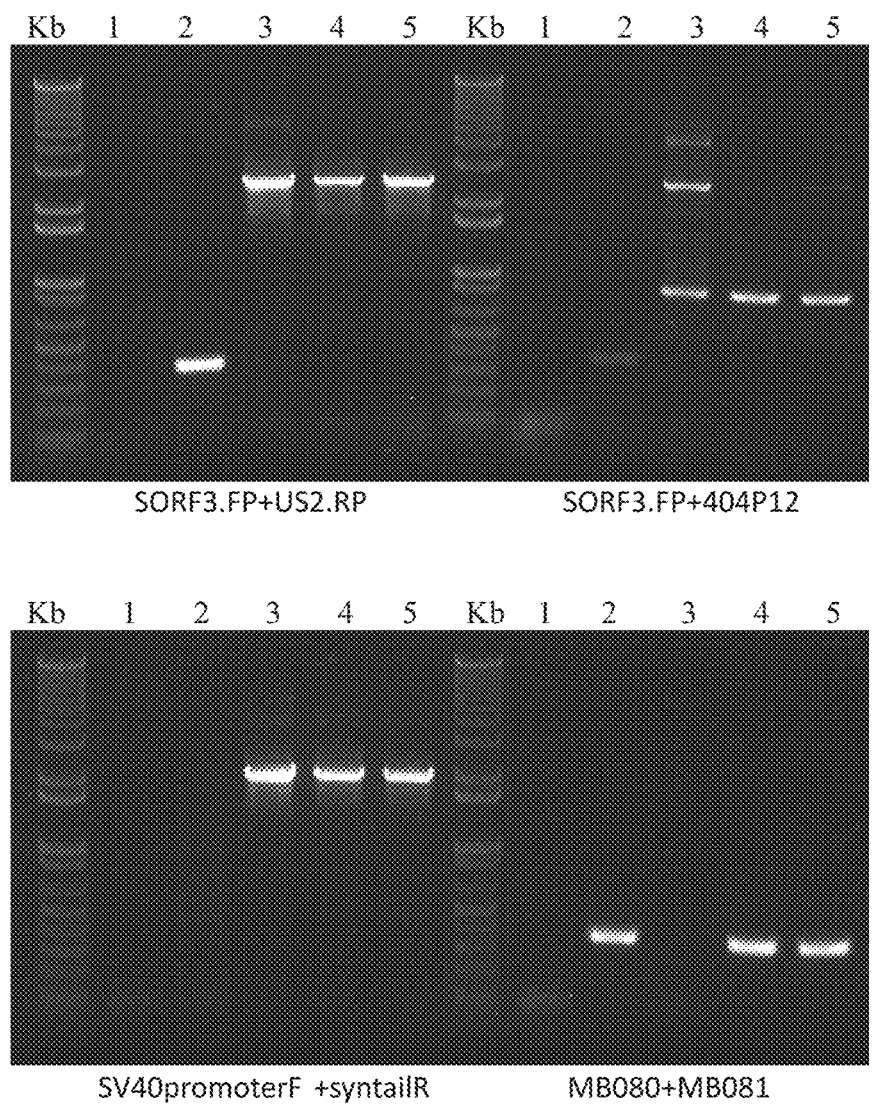
FIG. 31 depicts PCR identity result of vHVT406.

PCR analysis of vHVT406 was performed using the PCR primers listed in Table 6.3 (see FIG. 30). As shown in FIG. 31, the sizes of PCR products after gel electrophoresis correspond well with the expected sizes and the banding patterns. There is no evidence of the parental HVT FC126 virus in vHVT406.

TABLE 6.3

| Expected PCR bands using specific primer sets | | | |
|---|---|---|---|
| primer | HVTFC126 | pHVTUS2SVgDwtsyn | vHVT406 |
| S0RF3.FP + US2.RP | 0.334 | 2.218 | 2.218 |
| S0RF3.FP + 404P12 | — | 0.733 | 0.733 |
| SV40promoterF + syntailR | — | 1.829 | 1.829 |
| MB080 + MB081 | 0.323 | — | 0.323 |

| primer | SB-1 | pHVTUS2SVgDwtsyn | vHVT406 |
|---|---|---|---|
| SB1SORF4 + SB1US2R | 0.989 | — | — |

Conclusion

Based on PCR testing and immunofluorescence analysis, vHVT406 is a recombinant HVT virus containing an SV40 promoter, ILTV-gDwt gene, and synthetic poly A tail in the SOrf3-US2 site. vHVT406 is free of any detectable parental HVT virus.

Example 1.11 In Vitro Stability Study of the HVT Vectors

The HVT vectors constructed above were tested for genomic/expression stability after multiple in vitro passages in Chicken embryo fibroblast cells (CEF). The HVT vectors expressing two genes were stable after multiple passages. Contrary to the common knowledge that HVT with multiple inserts are less stable, the results demonstrated surprisingly that the HVT vectors of the present invention are stable and express two genes efficiently.

Example 2 Newcastle Disease (ND) Efficacy Induced at D28 by vHVT306, vHVT309, vHVT310 & vHVT311 in SPF Chicks The aim of the study was to assess the efficacy of four HVT recombinant constructs (vHVT306, vHVT309, vHVT310 & vHVT311) expressing the IBDV VP2 gene and NDV F gene administered to one-day-old SPF chickens against Newcastle disease challenges (Texas GB strain) performed on D28.

The characteristics of these vaccine candidates are described in Table 7 below.

TABLE 7

| Characteristics of the vectors used in the challenge study | | | | | |
|---|---|---|---|---|---|
| Name | Parental virus | gene | Promoter/ linker | Poly-A | Locus |
| vHVT306* | vHVT13** | IBDV VP2 | mCMV IE | SV40 Poly A | IG1 |
|  |  | NDV F | SV40 | Synthetic PolyA | SORF3-US2 |
| vHVT309 | vHVT13 | IBDV VP2 | mCMV IE | SV40 poly A | IG1 |
|  |  | NDV F | SV40 | Synthetic PolyA | IG1 |
| vHVT310 | vHVT13 | IBDV VP2 | mCMV IE | N/A | IG1 |
|  |  | NDV F | IRES | SV40 poly A | IG1 |
| vHVT311 | vHVT13 | IBDV VP2 | mCMV IE | N/A | IG1 |
|  |  | NDV F | P2A | SV40 poly A | IG1 | vHVT306*: the vHVT vector expressing IBDV VP2 and NDV F (see U.S. Pat. No. 9,114,108), used as a control.
vHVT13** is the active ingredient of the licensed VAXXITEK HVT-IBD vaccine based on an HVT vector expressing the IBDV VP2 gene (described as vHVT17 in U.S. Pat. No. 5,980,906 and EP 0 719 864).

Ninety five one-day-old specific pathogen free (SPF) chicks were assigned to 5 groups as shown in Table 8. All birds from groups 1 to 4 (20 birds/group) were vaccinated by the subcutaneous (SC) route with 0.2 mL of different HVT-IBD+ND constructs at the dose indicated (see Table 8). The 15 birds from group 5 were left unvaccinated. Twenty eight (D28) days post-vaccination, the birds in each group were challenged with NDV Texas GB strain by the intramuscular (IM) route ($10^{4.0}$ egg infectious dose 50% (EID50) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 8. All control birds of group 5 died after the challenge. Protection in the vaccinated groups reached at least 90%.

TABLE 8

ND efficacy induced by different HVT-IBD + ND double constructs in SPF chicks

| Group | Vaccine | Dose (PFU) | ND protection after D 28 challenge |
|---|---|---|---|
| 1 | vHVT306* | 1580 | 95% (19/20) |
| 2 | vHVT309 | 1680 | 90% (18/20) |
| 3 | vHVT310 | 2840 | 95% (19/20) |
| 4 | vHVT311 | 2980 | 90% (18/20) |
| 5 | — | — | 0% (0/15) | vHVT306*: used as a control

Example 3 IBD Efficacy Induced by vHVT309, vHVT310, vHVT311 and vHVT407 Against a Standard IBDV Challenge at D35

The aim of the study was to assess the efficacy of three HVT recombinant constructs (vHVT309, vHVT310 & vHVT311) expressing the IBDV VP2 gene and NDV F gene and one construct (vHVT407) expressing the IBDV VP2 gene and ILTV gD gene administered to one-day-old SPF chickens against standard IBDV challenge performed on D35.

One-day-old specific pathogen free (SPF) chicks were assigned to 4 groups as shown in Table 9. All birds from groups 1 to 4 (20 birds/group) were vaccinated by the subcutaneous (SC) route with 0.2 mL of different HVT-IBD+ND or HVT-IBD+ILT constructs at the dose indicated. The 20 birds from group 5 were left unvaccinated. Thirty five days after vaccination (at D35), all birds were challenged with the infectious bursal disease virus (IBDV) classical STC strain by the intraocular (IO) route ($10^{2.0}$EID50 in 0.03 mL/bird). Four days post-challenge (at D39) all birds were terminated and necropsied to examine for gross bursal lesions.

Results of protection are shown in Table 9. All vaccinated birds (except two vHVT311-vaccinated birds) were protected against IBD, whereas none of the control birds were protected.

TABLE 9

IBD efficacy induced by different HVT-IBD + ND or HVT-IBD + ILT double constructs in SPF chicks after challenge at D 35 with STC IBDV strain

| Group | Vaccine | Dose (PFU) | IBD STC protection after D 35 challenge |
|---|---|---|---|
| 1 | vHVT309 | 2180 | 100% (20/20) |
| 2 | vHVT310 | 3980 | 100% (20/20) |
| 3 | vHVT311 | 3180 | 90% (18/20) |
| 4 | vHVT407 | 1220 | 100% (20/20) |
| 5 | — | — | 0% (0/20) |

Example 4 IBD Efficacy Induced by vHVT309, vHVT310, vHVT311 and vHVT407 Against a Variant IBDV Challenge at D35

The aim of the study was to assess the efficacy of three HVT recombinant constructs (vHVT309, vHVT310 & vHVT311) expressing the IBDV VP2 gene and NDV F gene and one construct (vHVT407) expressing the IBDV VP2 gene and ILTV gD gene administered to one-day-old SPF chickens against a variant (Delaware E) IBDV challenge performed on D35.

One-day-old specific pathogen free (SPF) chicks were assigned to 6 groups as shown in Table 10. All birds from groups 1 to 4 (19-20 birds/group) were vaccinated by the subcutaneous (SC) route with 0.2 mL of different HVT-IBD+ND or HVT-IBD+ILTconstructs at the dose indicated. Birds from group 5 (19 birds) and group 6 (18 birds) were left unvaccinated. At D35, all birds from groups 1 to 5 were challenged with the infectious bursal disease virus (IBDV) variant Delaware E strain by the intraocular (IO) route ($10^{3.0}$ EID50 in 0.03 mL/bird). Birds from group 6 were left unchallenged. At D46, body weight and bursal weight of all birds were measured. The B/B wt. ratios (bursa weight/body weight ratio×100) were calculated for all groups.

Results of protection are shown in Table 10. Vaccinated birds from groups 1 and 2 had a mean B/B wt. ratio similar as that of non-vaccinated non-challenged controls (group 6) and greater than those of non-vaccinated challenged controls (group 5). Birds of group 3 were not protected and birds of group 4 were partially protected. Surprisingly, vHVT310 which contains IRES provided better protection than vHVT311 which contains P2A.

TABLE 10

IBD efficacy induced by different HVT-IBD + ND or HVT-IBD + ILT double constructs in SPF chicks after challenge at D 35 with variant E IBDV strain

| Group | Vaccine | Dose (PFU) | Number of birds | IBDV challenge at D 35 | Mean B/B wt. ratio |
|---|---|---|---|---|---|
| 1 | vHVT309 | 2180 | 20 | Yes | 0.43 |
| 2 | vHVT310 | 3980 | 20 | Yes | 0.50 |
| 3 | vHVT311 | 3180 | 20 | Yes | 0.18 |
| 4 | vHVT407 | 1220 | 19 | Yes | 0.32 |
| 5 | — | — | 19 | Yes | 0.13 |
| 6 | — | — | 18 | No | 0.45 |

Example 5 IBD Efficacy Induced by vHVT306, vHVT309 & vHVT310 Against a vvIBDV Challenge at D28 in Broilers The aim of the study was to assess the efficacy of three HVT recombinant constructs (vHVT306, vHVT309 & vHVT310) expressing the IBDV VP2 gene and NDV F gene administered to one-day-old broiler chickens against vvIBDV challenge performed on D28.

Seventy one-day-old broiler chicks (Hubbard JA957 line) were assigned to 5 groups as shown in Table 11. All birds from groups 2 to 5 (about 15 birds/group) were vaccinated by the subcutaneous (SC) route with 0.2 mL of different HVT-IBD+ND constructs at the dose indicated. Ten birds from group 1 were left unvaccinated. Twenty eight days after vaccination (at D28), all birds were challenged with the very virulent IBDV (vvIBDV) 91-168 strain by the intraocular (IO) route ($10^{4.3}$EID50 in 0.05 mL/bird). Ten days post-challenge (at D38) all birds were terminated and necropsied to examine for gross bursal lesions. Bursal and body were weighted and histopathology was performed on the bursa. Histological lesions of the bursa were scored from 0 to 5 according to the following scale: 0—No lesion, normal bursa; 1—1% to 25% of the follicles show lymphoid depletion (i.e., less than 50% of depletion in 1 affected follicle), influx of heterophils in lesions; 2—26% to 50% of the follicles show nearly complete lymphoid depletion (i.e., with more than 75% of depletion in 1 affected follicle), the affected follicles show necrosis lesions and severe influx of heterophils may be detected; 3—51% to 75% of the follicles show lymphoid depletion; affected follicles show necrosis lesions and a severe influx of heterophils is detected; 4—76% to 100% of the follicles show nearly complete lymphoid depletion; hyperplasia and cyst structures are detected; affected follicles show necrosis lesions and severe influx of heterophils is detected; and 5—100% of the follicles show nearly complete lymphoid depletion; complete loss of follicular structure; thickened and folded epithelium; fibrosis of bursal tissue. Birds were considered as protected if they did not show clinical signs post-challenge and if their histology score was ≤2.

There were some early mortalities in the first week in this batch of broilers likely due to colibacillosis. The dose of the tested vaccines was lower than expected (2000PFU). Results of protection are shown in Table 11. Partial protection was induced by vaccination which shows vHVT310 being higher than vHVT306 and vHVT309.

TABLE 11

IBD efficacy induced by different HVT-IBD + ND double constructs in broiler chicks after challenge at D 28 with vvIBDV strain

| Group | Vaccine | Dose (PFU) | Mean Bursal/body weight ratio (*1000) | Protection based on histopathology score |
|---|---|---|---|---|
| 1 | — | — | 0.75 | 0% |
| 2 | vHVT306 | 955 | 1.07 | 20% |
| 3 | vHVT309 | 741 | 0.89 | 20% |
| 4 | vHVT310 | 708 | 1.38 | 53% |
| 5 | vHVT13* | 2000 | 1.99 | 80% | vHVT13*: used as a control.

Example 6 ND Efficacy Induced by vHVT306, vHVT309 & vHVT310 Against a Velogenic NDV Challenge at D42 in Broilers The aim of the study was to assess the efficacy of three HVT recombinant constructs (vHVT306, vHVT309 & vHVT310) expressing the IBDV VP2 gene and NDV F gene administered to one-day-old broiler chickens against velogenic NDV challenge performed on D42.

One-day-old broiler chicks (Hubbard JA957 line) were assigned to 4 groups as shown in Table 12. All birds from groups 2 to 4 (16-20 birds/group) were vaccinated by the subcutaneous (SC) route with 0.2 mL of different HVT-IBD+ND constructs at the dose indicated. Twelve birds from group 1 were left unvaccinated. Forty two days after vaccination (at D42), all birds were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

There were some early mortalities in the first week in this batch of broilers likely due to colibacillosis. The dose of the tested vaccines was lower than expected (2000PFU). Results of protection are shown in Table 12. Best protections were induced by vaccination with vHVT309 & vHVT310, followed by vHVT306.

TABLE 12

ND efficacy induced by different HVT-IBD + ND double constructs in broiler chicks after challenge at D 42 with velogenic NDV strain

| Group | Vaccine | Dose (PFU) | Protection against mortality | Protection against mortality & morbidity |
|---|---|---|---|---|
| 1 | — | — | 8.3% | 0% |
| 2 | vHVT306 | 955 | 68.8% | 62.5% |
| 3 | vHVT309 | 741 | 85% | 85% |
| 4 | vHVT310 | 708 | 85% | 80% |

Example 7 ND Efficacy Induced by vHVT306, vHVT309 & vHVT310 Against a Velogenic NDV Challenge at D42 in Broilers The aim of the study was to re-assess the efficacy of three HVT recombinant constructs (vHVT306, vHVT309 & vHVT310) expressing the IBDV VP2 gene and NDV F gene administered to one-day-old broiler chickens against velogenic NDV challenge performed on D42.

One-day-old broiler chicks (Hubbard JA957 line) were assigned to 4 groups as shown in Table 13. All birds from groups 2 to 4 (16-20 birds/group) were vaccinated by the subcutaneous (SC) route with 0.2 mL of different HVT-IBD+ND constructs at 2000 PFU. Nineteen birds from group 1 were left unvaccinated. Forty two days after vaccination (at D42), all birds were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

Results of protection are shown in Table 13. Overall, the levels of protection were higher than the previous study (see example 6), but they follow the same trend: best protections were induced by vaccination with vHVT309 & vHVT310, followed by vHVT306.

The results showed that vHVT309 is more efficacious than vHVT306 against ND challenges in SPF as well as broilers (Tables 12 &13), suggesting that inserting heterologous polynucleotides in one locus have less negative impact on the overall fitness of the virus than inserting in multiple loci.

TABLE 13

ND efficacy induced by different HVT-IBD + ND double constructs in broiler chicks after challenge at D 42 with velogenic NDV strain

| Group | Vaccine | Dose (PFU) | Protection against mortality | Protection against mortality & morbidity |
|---|---|---|---|---|
| 1 | — | — | 0% | 0% |
| 2 | vHVT306 | 955 | 75% | 75% |
| 3 | vHVT309 | 741 | 94% | 89% |
| 4 | vHVT310 | 708 | 94% | 94% |

Example 8 IBD Efficacy Induced by vHVT306, vHVT309 & vHVT310 Against a Standard IBDV Challenge at D14 in SPF Chicks The aim of the study was to assess the efficacy of three HVT recombinant constructs (vHVT306, vHVT309 & vHVT310) expressing the IBDV VP2 gene and NDV F gene administered to one-day-old SPF chickens against standard IBDV challenge performed at D14.

One-day-old specific pathogen free (SPF) chicks were assigned to 4 groups as shown in Table 14. All birds from groups 1 to 3 (21-22 birds/group) were vaccinated by the subcutaneous (SC) route with 0.2 mL of different HVT-IBD+ND constructs at the dose indicated. The 22 birds from group 4 were left unvaccinated. Fourteen days after vaccination (at D14), all birds were challenged with the infectious bursal disease virus (IBDV) classical STC strain by the intraocular (IO) route ($10^{1.4}$ EID50 in 0.03 mL/bird). Four days post-challenge (at D18) all birds were terminated and necropsied to examine for gross bursal lesions.

Results of protection are shown in Table 14. Similar levels of IBD protection were induced by the 3 experimental vaccines, whereas all but one control birds was infected.

TABLE 14

IBD efficacy induced by different HVT-IBD + ND double constructs in SPF chicks after challenge at D 14 with STC IBDV strain

| Group | Vaccine | Dose (PFU) | IBD STC protection after D 14 challenge (infected/total) |
|---|---|---|---|
| 1 | vHVT306 | 2061 | 68.2% (7/22) |
| 2 | vHVT309 | 1476 | 76.2% (5/21) |
| 3 | vHVT310 | 1970 | 68.2% (7/22) |
| 4 | — | — | 4.5% (21/22) |

Example 9 IBD Efficacy Induced by vHVT306, vHVT309 & vHVT310 in SPF Chicks after Variant IBD Challenge at D14

The aim of the study was to assess the efficacy of three HVT recombinant constructs (vHVT306, vHVT309 & vHVT310) expressing the IBDV VP2 gene and NDV F gene administered to one-day-old SPF chickens against variant IBDV challenge performed at D14.

One-day-old specific pathogen free (SPF) chicks were assigned to 5 groups as shown in Table 15. All birds from groups 1 to 3 (20 birds/group) were vaccinated by the subcutaneous (SC) route with 0.2 mL of different HVT-IBD+ND constructs at the dose indicated. Birds from group 4 and group 5 (19-20 birds/group) were left unvaccinated. At D14, all birds from groups 1 to 4 were challenged with the infectious bursal disease virus (IBDV) variant Delaware E strain by the intraocular (IO) route ($10^{2.2}$EID50 in 0.03 mL/bird). Birds from group 5 were left unchallenged. At D25, body weight and bursal weight of all birds were measured. The BB wt. ratios (bursa weight/body weight ratio×100) were calculated for all groups.

Results of protection are shown in Table 15. Partial protection was induced at D14 by the 3 vaccines, protection being higher for vHVT309 and vHVT310.

Recombinant vHVT306 and vHVT309 have two independent expression cassettes (two mRNAs). The constructs expressing two genes through an IRES or P2A (for example, vHVT310, vHVT317, vHVT311, vHVT316, vHVT322) are not only in one insertion site, but also the genes are expressed from a single mRNA. Comparing all the data presented in Tables 11 to 19, it shows that one insertion site recombinants vHVT309 and vHVT310 are more efficacious than two insertion site recombinant vHVT306, indicating that HVT recombinants carrying more than one heterologous polynucleotides in one insertion locus are biologically more fit than HVT recombinants carrying heterologous polynucleotides in multiple insertion loci. Furthermore, surprisingly, expressing more than one heterologous polynucleotides from a single mRNA expressed through an IRES has less negative impact on IBD efficacy, particularly in broilers (see results on Table 11).

TABLE 15

IBD efficacy induced by different HVT-IBD + ND double constructs in SPF chicks after challenge at D 14 with variant E IBDV strain

| Group | Vaccine | Dose (PFU) | Number of birds | IBDV challenge at D 14 | Mean B/B wt. ratio |
|---|---|---|---|---|---|
| 1 | vHVT306 | 2061 | 20 | Yes | 0.18 |
| 2 | vHVT309 | 1476 | 20 | Yes | 0.33 |
| 3 | vHVT310 | 1970 | 20 | Yes | 0.27 |
| 4 | — | — | 19 | Yes | 0.13 |
| 5 | — | — | 20 | No | 0.64 |

Example 10 IBD Efficacy Induced by vHVT306, vHVT309 & vHVT310 Against a Standard IBDV Challenge at D28 in SPF Chicks The aim of the study was to assess the efficacy of three HVT recombinant constructs (vHVT306, vHVT309 & vHVT310) expressing the IBDV VP2 gene and NDV F gene administered to one-day-old SPF chickens against standard IBDV challenge performed at D28.

One-day-old specific pathogen free (SPF) chicks were assigned to 4 groups as shown in Table 16. All birds from groups 1 to 3 (20-22 birds/group) were vaccinated by the subcutaneous (SC) route with 0.2 mL of different HVT-IBD+ND constructs at the dose indicated. The 22 birds from group 4 were left unvaccinated. Twenty eight days after vaccination (at D28), all birds were challenged with the infectious bursal disease virus (IBDV) classical STC strain by the intraocular (IO) route ($10^{2.0}$EID50 in 0.03 mL/bird). Four days post-challenge (at D32) all birds were terminated and necropsied to examine for gross bursal lesions.

Results of protection are shown in Table 16. Full protection was induced by vHVT310 whereas only a few birds were not protected for the other vaccine candidates.

TABLE 16

IBD efficacy induced by different HVT-IBD + ND double constructs in SPF chicks after challenge at D 28 with STC IBDV strain

| Group | Vaccine | Dose (PFU) | IBD STC protection after D 28 challenge (infected/total |
|---|---|---|---|
| 1 | vHVT306 | 2061 | 86.4% (3/22) |
| 2 | vHVT309 | 1476 | 95.0% (1/20) |
| 3 | vHVT310 | 1970 | 100% (0/22) |
| 4 | — | — | 4.5% (21/22) |

Example 11 IBD Efficacy Induced by vHVT306, vHVT309 & vHVT310 in SPF Chicks after Variant IBD Challenge at D28

The aim of the study was to assess the efficacy of three HVT recombinant constructs (vHVT306, vHVT309 & vHVT310) expressing the IBDV VP2 gene and NDV F gene administered to one-day-old SPF chickens against variant IBDV challenge performed at D28.

One-day-old specific pathogen free (SPF) chicks were assigned to 5 groups as shown in Table 17. All birds from groups 1 to 3 (20 birds/group) were vaccinated by the subcutaneous (SC) route with 0.2 mL of different HVT-IBD+ND constructs at the dose indicated. Birds from group 4 and group 5 (18-19 birds/group) were left unvaccinated. At D28, all birds from groups 1 to 4 were challenged with the infectious bursal disease virus (IBDV) variant Delaware E strain by the intraocular (IO) route ($10^{2.2}$ EID50 in 0.03 mL/bird). Birds from group 5 were left unchallenged. At D39, body weight and bursal weight of all birds were measured. The B/B wt. ratios (bursa weight/body weight ratio×100) were calculated for all groups.

Results of protection are shown in Table 17. The B/B wt ratio for group 5 (unchallenged group) could not be obtained since this group was unexpectedly infected with the STC IBDV strain. Protection induced by vHVT310 was higher than that induced by vHVT306 and vHVT309.

TABLE 17

IBD efficacy induced by different HVT-IBD + ND double constructs in SPF chicks after challenge at D 28 with variant E IBDV strain

| Group | Vaccine | Dose (PFU) | Number of birds | IBDV challenge at D 28 | Mean B/B wt. ratio |
|---|---|---|---|---|---|
| 1 | vHVT306 | 2061 | 20 | Yes | 0.21 |
| 2 | vHVT309 | 1476 | 20 | Yes | 0.26 |
| 3 | vHVT310 | 1970 | 20 | Yes | 0.37 |
| 4 | — | — | 19 | Yes | 0.11 |
| 5 | — | — | 20 | No | ND* |

*Not done due to standard IBDV exposure in this group

Example 12 Newcastle Disease (ND) Efficacy Induced at D21 and D28 by vHVT306, vHVT309 & vHVT310 in SPF Chicks The aim of the study was to assess the efficacy of three HVT recombinant constructs (vHVT309, vHVT310 & vHVT311) expressing the IBDV VP2 gene and NDV F gene administered to one-day-old SPF chickens against Newcastle disease challenges (Texas GB strain) performed on D21 and D28.

One-day-old specific pathogen free (SPF) chicks were assigned to 4 groups as shown in Table 18. All birds from groups 1 to 3 (50 birds/group) were vaccinated by the subcutaneous (SC) route with 0.2 mL of different HVT-IBD+ND constructs at the dose indicated. The 30 birds from group 4 were left unvaccinated. Twenty one (D21) days post-vaccination, 20 birds from groups 1-3 and 15 birds from group 4 were challenged with NDV Texas GB strain by the intramuscular (IM) route ($10^{4.2}$ egg infectious dose 50% (EID50) in 0.1 mL/bird). Twenty eight (D28) days post-vaccination, 30 birds from groups 1-3 and 15 birds from group 4 were challenged with NDV Texas GB strain by the intramuscular (IM) route ($10^{4.3}$ egg infectious dose 50% (EID50) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 18. All control birds of group 4 died after the challenge. Protection induced by vHVT310 was the best followed by vHVT306 and vHVT309.

TABLE 18

ND efficacy at D 21 and D 28 induced by different HVT-IBD + ND double constructs in SPF chicks

| Group | Vaccine | Dose (PFU) | ND protection after D 21 challenge (protected/total) | ND protection after D 28 challenge (protected/total) |
|---|---|---|---|---|
| 1 | vHVT306* | 2248 | 80% (16/20) | 90% (27/30) |
| 2 | vHVT309 | 1765 | 60% (12/20) | 86.2% (25/29) |
| 3 | vHVT310 | 2106 | 85% (17/20) | 100% (29/29) |
| 4 | — | — | 0% (0/15) | 0% (0/15) | vHVT306*: used as a control

Example 13 Marek's Disease (MD) Efficacy Induced by vHVT306, vHVT309 & vHVT310 in SPF Chicks The aim of the study was to assess the efficacy of three HVT recombinant constructs (vHVT309, vHVT310 & vHVT311) expressing the IBDV VP2 gene and NDV F gene administered to one-day-old SPF chickens against Marek's disease challenges (GA strain, 2 batches & 2 dilutions).

One-day-old specific pathogen free (SPF) chicks were assigned to 4 groups as shown in Table 19. All birds from groups 1 to 3 (20 birds/group) were vaccinated by the subcutaneous (SC) route with 0.2 mL of different HVT-IBD+ND constructs at the dose indicated. The 20 birds from group 4 were left unvaccinated. Four days post-vaccination (D4), 18-20 birds from groups 1-4 were challenged with two dilutions (1:5 and 1:640) of two different batches (#1 and #2) of the vMDV GA22 strain by the SC route. Birds were observed for clinical signs attributable to Marek's disease during 46-50 days post-hatch. At D46-D50, all remaining birds were necropsied and checked for Marek's disease lesions. Birds that did not show any MD clinical signs or lesions were considered as protected.

Results of protection are shown in Table 19. Infectivity in control birds of group 4 varied between 75-90%. Overall, protection induced by vHVT310 was the best followed closely by vHVT306 and then vHVT309.

TABLE 19

MD efficacy induced by different HVT-IBD + ND double constructs in SPF chicks against 2 different lots of GA22 challenge either diluted 1:5 or 1:640

| Group | Vaccine | Dose (PFU) | MD protect. GA22 lot #1 1:5 dil. | MD protect. GA22 lot #1 1:640 dil. | MD protect. GA22 lot #2 1:5 dil. | MD protect. GA22 lot #2 1:640 dil. |
|---|---|---|---|---|---|---|
| 1 | vHVT306* | 2420 | 75% (15/20) | 85% (17/20) | 26.3% (5/19) | 70% (14/20) |
| 2 | vHVT309 | 1893 | 50% (10/20) | 72.2% (13/18) | 55% (11/20) | 70% (14/20) |
| 3 | vHVT310 | 2127 | 80% (16/20) | 84.2% (16/19) | 40% (8/20) | 90% (18/20) |
| 4 | — | — | 25% (5/20) | 10% (2/20) | 10% (2/20) | 20% (4/20) | vHVT306*: used as a control

Example 14 IBD Efficacy Induced by vHVT306 and vHVT407 Against a Classical IBDV Challenge at D21 in SPF Chicks The aim of the study was to assess the efficacy of two HVT recombinant constructs, one (vHVT306) expressing the IBDV VP2 gene and NDV F gene and the other (vHVT407) expressing the IBDV VP2 gene and ILTV gD gene administered to one-day-old SPF chickens against a classical IBDV challenge performed on D21.

Forty one-day-old SPF chicks (white Leghorn) were assigned to 3 groups as shown in Table 20. All birds from groups 2 & 3 (about 15 birds/group) were vaccinated by the subcutaneous (SC) route with 0.2 mL of vHVT306 or vHVT407 construct at the dose indicated. Ten birds from group 1 were left unvaccinated. Twenty one days after vaccination (at D21), all birds were challenged with the classical 52/70 Faragher IBDV strain by the intraocular (IO) route ($10^{2.0}$ EID50 in 0.05 mL/bird). Eleven days post-challenge (at D32) all birds were terminated and necropsied to examine for gross bursal lesions. Bursal and body were weighted to calculate the bursal on body weight ratio. Birds were considered as protected if they did not show clinical signs or bursal lesion post-challenge.

Results of protection are shown in Table 20. Complete IBD protection was induced by vaccination with vHVT306 or vHVT407.

TABLE 20

IBD efficacy induced by two HVT constructs expressing two genes in SPF chicks after challenge at D 21 with Faragher IBDV strain

| Group | Vaccine | Dose (log10 PFU) | Clinical signs #dead/ #sick/total | Mean Bursal/body weight ratio (*1000) | % with gross bursal lesion |
|---|---|---|---|---|---|
| 1 | — | — | 3/4/10 | 1.6 ± 0.7** | 100% |
| 2 | vHVT306* | 3.1 | 0/0/15 | 6.1 ± 1.1 | 0% |
| 3 | vHVT407 | 3.1 | 0/0/15 | 6.3 ± 1.1 | 0% | vHVT306*: used as a control.
**mean ± standard deviation

Example 15 ILT Efficacy Induced by vHVT407 Against an ILTV Challenge at D21 in SPF Chicks The aim of the study was to assess the efficacy of two vHVT407 recombinant construct expressing the IBDV VP2 gene and the ILTV gD gene administered to one-day-old SPF chickens against an ILTV challenge performed on D21.

Twenty four one-day-old SPF chicks (white Leghorn) were assigned to 2 groups as shown in Table 21. All birds (about 12 birds/group) were vaccinated by the subcutaneous (SC) route with 0.2 mL of vHVT13 (used as a negative control) or vHVT407 construct at the dose indicated. Twenty one days after vaccination (at D21), all birds were challenged with the ILT-96-3 ILTV strain by the intratracheal (IT) route ($10^{3.6}$ EID50 in 0.5 mL/bird). The birds were observed for clinical signs for 11 days post-challenge. On Study Days 25-29 and 32 all the birds were observed for clinical signs including breathing pattern, conjunctivitis, depression and mortality. On Study Day 32, all the remaining birds were terminated. Birds were considered as protected if they did not show ILT clinical signs such as respiratory distress associated with coughing, sneezing, rales, depression, gasping and/or bloody mucous exudates, including mortality.

Results of protection are shown in Table 21. Significant ILT protection was induced by vaccination with vHVT407 in these challenge conditions.

TABLE 21

ILT efficacy induced by vHVT407 construct in SPF chicks after challenge at D 21 with ILT-96-3 ILTV strain

| Group | Vaccine | Dose (PFU) | Clinical signs #dead/#sick/total | Clinical Protection |
|---|---|---|---|---|
| 1 | vHVT13* | 3420 | 6/2/11 | 27% |
| 2 | vHVT407 | 2880 | 2/0/12 | 83% | vHVT13*: used as a negative control.

Example 16 ILT Efficacy Induced by vHVT407, a Commercial HVT-ILT and a Commercial Chicken Embryo Origin (CEO) Vaccine Against an ILTV Challenge at D21 in Broiler Chicks The aim of the study was to assess the efficacy of vHVT407 recombinant construct expressing the IBDV VP2 gene and the ILTV gD gene administered to one-day-old broiler chickens compared to a commercial HVT-ILT vaccine (INNOVAX® ILT) against an ILTV challenge performed on D21.

Forty eight one-day-old commercial broiler chicks were assigned to 3 groups as shown in Table 22. All birds (about 12 birds/group) of groups 1-3 were vaccinated by the subcutaneous (SC) route with 0.2 mL of vHVT13 (used as a negative control), vHVT407 or INNOVAX® ILT (used as a positive control) constructs at the dose indicated. Twenty one days after vaccination (at D21), all birds were challenged with the ILT-96-3 ILTV strain by the intratracheal (IT) route ($10^{4.2}$ EID50 in 0.5 mL/bird). The birds were observed for clinical signs for 12 days post-challenge. On Study Days 25-29 and 32-33 all the birds were observed and scored for clinical signs including breathing pattern, conjunctivitis, depression and mortality. On Study Day 34, all the remaining birds were terminated. Birds were considered as protected if they did not show ILT clinical signs such as respiratory distress associated with coughing, sneezing, rales, depression, gasping and/or bloody mucous exudates, including mortality.

Results of protection are shown in Table 22. ILT protection was induced by vaccination with vHVT407, which was higher than that induced by INNOVAX ILT.

TABLE 22

ILT efficacy induced by vHVT407 and INNOVAX
ILT constructs in broiler chicks after challenge
at D 21 with ILT-96-3 ILTV strain

| Group | Vaccine | Dose | Clinical signs #dead/#sick/total | Clinical Protection |
|---|---|---|---|---|
| 1 | vHVT13* | 2200 PFU | 5/7/12 | 0% |
| 2 | vHVT407 | 1860 PFU | 1/4/11 | 55% |
| 3 | INNOVAX ILT** | 2240 PFU | 0/10/12 | 17% | vHVT13*: used as a negative control.
**INNOVAX ® ILT used as a positive control

Example 17 Newcastle Disease (ND) Efficacy Induced at D14, D21 and D32 by vHVT310 & vHVT316 in SPF Chicks The aim of the study was to compare the onset of ND immunity of two HVT recombinant constructs (vHVT310 & vHVT316) expressing the IBDV VP2 gene and NDV F gene administered to one-day-old SPF chickens against Newcastle disease challenges (Texas GB strain) performed on D14, D21 and D32.

One-day-old specific pathogen free (SPF) chicks were assigned to 3 groups as shown in Table 23. All birds from groups 1 to 2 (59-70 birds/group; see table) were vaccinated by the subcutaneous (SC) route with 0.2 mL of different HVT-IBD+ND constructs at the dose indicated. The 45 birds from group 3 were left unvaccinated. At D14, D21 and D32, 15-30 birds (see table) from groups 1-3 were challenged with NDV Texas GB strain by the intramuscular (IM) route ($10^{4.0}$EID50/bird) in 0.1 mL/bird). Birds were observed for clinical signs during 14 days after challenge. Birds that did not show any ND clinical signs (including central nervous, or respiratory signs and/or death) for up to 14 days post-challenge were considered as protected.

Results of protection are shown in Table 23. All control birds of group 3 died after the challenge. Protection levels induced by both vHVT310 and vHVT316 were similar, with a possible earlier onset of immunity induced by vHVT316.

TABLE 23

ND efficacy at D 14, D 21 and D 32 induced by different
HVT-IBD + ND double constructs in SPF chicks

| Group | Vaccine | Dose (PFU) | ND protection after D 14 challenge (protected/total) | ND protection after D 21 challenge (protected/total) | ND protection after D 32 challenge (protected/total) |
|---|---|---|---|---|---|
| 1 | vHVT310 | 2473 | 30% (6/20) | 80% (16/20) | 97% (29/30) |
| 2 | vHVT316 | 2367 | 45% (9/20) | 80% (16/20) | 100% (19/19) |
| 3 | — | — | 0% (0/15) | 0% (0/15) | 0% (0/15) |

Example 18 ILTV Efficacy Induced by HVT Vectors Expressing ILTV gD and IBDV VP2 or Expressing ILTV gD and NDV F The aim of the study is to assess the efficacy of the HVT recombinant constructs expressing ILTV gD and IBDV VP2 (such as vHVT317 and vHVT407) or expressing ILTV gD and NDV F genes (such as vHVT308 and vHVT322) administered to chickens against ILTV challenges.

Chickens are assigned to different groups. Birds are vaccinated by the subcutaneous (SC) route with 0.2 mL of different HVT constructs. The birds from one group are left unvaccinated. Birds are challenged with ILTV by the intratracheal (IT) or the infraorbital sinus route. Birds are observed for clinical signs during 11-14 days after challenge. Birds that do not show any ILTV clinical signs (including respiratory distress associated with coughing, sneezing, rales, depression, gasping and/or bloody mucous exudates and/or death) for up to 14 days post-challenge are considered as protected.

The results show that the HVT vectors provide protection against ILTV infection.

Example 19 IBD Efficacy Induced by HVT Vectors Expressing ILTV gD and IBDV VP2

The aim of the study is to assess the efficacy of the HVT recombinant constructs expressing ILTV gD and IBDV VP2 (such as vHVT317 and vHVT407) administered to chickens against IBD challenges.

Chickens are assigned to different groups. Birds are vaccinated by the subcutaneous (SC) route with 0.2 mL of different HVT constructs. The birds from one group are left unvaccinated. Birds are challenged with IBD by the intraocular (IO) route. Birds are observed for clinical signs during 4 to 10 days after challenge. Birds that do not show any IBD clinical signs (including depression and/or death) and that do not show bursal lesions and/or atrophy for up to 10 days post-challenge are considered as protected.

The results show that the HVT vectors provide protection against IBD infection.

Example 20 NDV Efficacy Induced by HVT Vectors Expressing ILTV gD and NDV F

The aim of the study is to assess the efficacy of the HVT recombinant constructs expressing ILTV gD and NDV F genes (such as vHVT308 and vHVT322) administered to chickens against NDV challenges.

Chickens are assigned to different groups. Birds are vaccinated by the subcutaneous (SC) route with 0.2 mL of different HVT constructs. The birds from one group are left unvaccinated. Birds are challenged with NDV by the intramuscular (IM) route. Birds are observed for clinical signs during 14 days after challenge. Birds that do not show any ND clinical signs (including central nervous, or respiratory signs and/or death) for up to 14 days post-challenge are considered as protected.

The results show that the HVT vectors provide protection against NDV infection.

Example 21 IBD Efficacy Induced by vHVT316 & vHVT317 Against a Standard IBDV Challenge at D28 in SPF Chicks The aim of the study was to assess the efficacy of two HVT recombinant constructs (vHVT316 & vHVT317)

expressing either the IBDV VP2 gene and NDV F gene (vHVT316) or the IBDV VP2 gene and ILTV gD gene (vHVT317) administered to one-day-old SPF chickens against standard IBDV challenge performed at D28.

One-day-old specific pathogen free (SPF) chicks were assigned to 3 groups as shown in Table 24. All birds from groups 1 & 2 (15 birds/group) were vaccinated by the subcutaneous (SC) route with 0.2 mL of vHVT316 & vHVT317 at the dose indicated. The 15 birds from group 3 were left unvaccinated. Twenty eight days after vaccination (at D28), all birds were challenged with the infectious bursal disease virus (IBDV) classical STC strain by the intraocular (IO) route ($10^{2.0}$EID50 in 0.03 mL/bird). Four days post-challenge (at D32), all birds were terminated and necropsied to examine for gross bursal lesions.

Results of protection are shown in Table 24. 100% and 80% protection were induced by vHVT316 and vHVT317, respectively; however, the dose administered of vHVT317 was nearly 3 times lower than that of vHVT316.

TABLE 24

IBD efficacy induced by HVT-IBD + ND (vHVT316)
and HVT-IBD + ILT (vHVT317) double constructs
in SPF chicks after challenge at D 28 with STC IBDV strain

| Group | Vaccine | Dose (PFU) | IBD STC protection after D 28 challenge (infected/total) |
|---|---|---|---|
| 1 | vHVT316 | 2910 | 100% (0/15) |
| 2 | vHVT317 | 1030 | 80.0% (3/15) |
| 3 | — | — | 6.7% (14/15) |

Example 22 IBD Efficacy Induced by vHVT310, vHVT316 & vHVT317 in SPF Chicks after Variant IBD Challenge at D28

The aim of the study was to assess the efficacy of three HVT recombinant constructs (vHVT310, vHVT316 & vHVT317) expressing either the IBDV VP2 gene and NDV F gene (vHVT310 & vHVT316) or the IBDV VP2 gene and ILTV gD gene (vHVT317) administered to one-day-old SPF chickens against variant IBDV challenge performed at D28.

One-day-old specific pathogen free (SPF) chicks were assigned to 5 groups as shown in Table 25. All birds from groups 1 to 3 (15 birds/group) were vaccinated by the subcutaneous (SC) route with 0.2 mL of vHVT310, vHVT316 & vHVT317 at the dose indicated. Birds from group 4 and group 5 (15 birds/group) were left unvaccinated. At D28, all birds from groups 1 to 4 were challenged with the infectious bursal disease virus (IBDV) variant Delaware E strain by the intraocular (IO) route ($10^{3.0}$EID50 in 0.03 mL/bird). Birds from group 5 were left unchallenged. At D39, body weight and bursal weight of all birds were measured. The BB wt. ratios (bursa weight/body weight ratio×100) were calculated for all groups.

Results of protection are shown in Table 25. Protection was observed in all vaccinated groups. Protection with vHVT317 was slightly higher than that induced by vHVT310 and vHVT316 despite its lower dose.

TABLE 25

IBD efficacy induced by different HVT constructs with double inserts
in SPF chicks after challenge at D 28 with variant E IBDV strain

| Group | Vaccine | Dose (PFU) | Number of birds | IBDV challenge at D 28 | Mean B/B wt. ratio |
|---|---|---|---|---|---|
| 1 | vHVT310 | 2260 | 15 | Yes | 0.34 |
| 2 | vHVT316 | 2910 | 15 | Yes | 0.33 |
| 3 | vHVT317 | 1030 | 15 | Yes | 0.40 |
| 4 | — | — | 15 | Yes | 0.12 |
| 5 | — | — | 15 | No | 0.43 |

Example 23 ILT Efficacy Induced by vHVT317 Against a ILTV Challenge at D28 in SPF Chicks The aim of the study was to assess the efficacy of the vHVT317 recombinant construct expressing the IBDV VP2 gene and the ILTV gD gene administered to one-day-old SPF chickens against an ILTV challenge performed on D28.

Thirty six one-day-old SPF chicks (white Leghorn) were assigned to 2 groups as shown in Table 26. All birds (about 18 birds/group) were either vaccinated by the subcutaneous (SC) route with 0.2 mL of vHVT317 or left unvaccinated. Twenty eight days after vaccination (at D28), all birds were challenged with the ILT-96-3 ILTV strain by the intratracheal (IT) route ($10^{3.0}$EID50 in 0.2 mL/bird). The birds were observed for clinical signs and mortality at D32, D36 & D39. Clinical signs included breathing pattern, conjunctivitis, depression and mortality. On Study Day 32, all the remaining birds were terminated. Evaluation of protection was used using 3 different criteria: (1) Any bird exhibiting any clinical signs for three consecutive days or that died after challenge is considered as ILT positive; (2) Any bird exhibiting any moderate or severe clinical signs in any category for any day or that died after challenge is considered as ILT positive; and (3) Any bird exhibiting any moderate or severe clinical signs in any category for two consecutive days or that died after challenge is considered as ILT positive.

Results of protection based on the 3 different criteria are shown in Table 26. The ILT challenge was severe since it killed (or birds were euthanized when they show very severe clinical signs for ethical reason) 86.7% of non-vaccinated birds. High levels of ILT protection were induced by vaccination with vHVT317 in these challenge conditions.

TABLE 26

ILT efficacy induced by vHVT317 construct in SPF chicks
after challenge at D 28 with ILT-96-3 ILTV strain

| Group | Vaccine | Dose (PFU) | Number of birds | % Mortality | % Protection based on criteria 1/2/3 |
|---|---|---|---|---|---|
| 1 | vHVT317 | 1030 | 15 | 0% | 100%/86.7%/100% |
| 2 | — | — | 15 | 86.7% | 6.7%/6.7%/6.7% |

Example 24 ILT Efficacy Induced by vHVT317, a Commercial HVT-ILT and a Commercial Chicken Embryo Origin (CEO) Vaccine Against an ILTV Challenge at D21 in Broiler Chicks The aim of the study was to assess the efficacy of vHVT317 recombinant construct expressing the IBDV VP2 gene and the ILTV gD gene administered to one-day-old broiler chickens compared to a commercial HVT-ILT vaccine (INNOVAX® ILT, Merck Animal Health) against an ILTV challenge performed on D28.

Fifty one one-day-old commercial broiler chicks were assigned to 3 groups as shown in Table 27. All birds (17 birds/group) were either vaccinated by the subcutaneous (SC) route with 0.2 mL of vHVT317 or INNOVAX® ILT (used as a positive control) at the dose indicated or left unvaccinated. At D26, the number of birds per group was reduced to 15 and each bird was weighed. Twenty eight days after vaccination (at D28), all birds were challenged with the 63140 ILTV strain by the infraorbital route ($10^{4.3}$ EID50 in 0.2 mL/bird). On Study Days 31 to 35, and Study Day 38, all birds were individually observed for clinical signs. On Study Day 38, all the remaining birds were individually weighed and terminated. Evaluation of protection was performed using 3 different criteria: (1) Any bird exhibiting any clinical signs for three consecutive days or that died after challenge is considered as ILT positive; (2) Any bird exhibiting any moderate or severe clinical signs in any category for any day or that died after challenge is considered as ILT positive; and (3) Any bird exhibiting any moderate or severe clinical signs in any category for two consecutive days or that died after challenge is considered as ILT positive. The body weight was also compared at D26 and D38.

Results of protection using the 3 criteria are shown in Table 27. All controls were considered non-protected for the 3 criteria. Both tested vaccines induced high and similar ILT protection. There were no significant difference between body weight at D26 (before challenge); however, after challenge, body weights of vaccinated birds were significantly (p<0.0001) higher than those of non-vaccinated birds indicating protection against weight loss.

TABLE 27

ILT efficacy induced by vHVT317 and INNOVAX ILT (positive control) constructs in broiler chicks after challenge at D28 with 63140 ILTV strain

| Group | Vaccine | Dose (PFU) | Number of birds | % Protection based on criteria 1/2/3 | Body weight at D26* | Body weight at D38* |
|---|---|---|---|---|---|---|
| 1 | vHVT317 | 3820 | 15 | 86.7%/86.7%/86.7% | 1544 ± 61 | 2931 ± 63 |
| 1 | INNOVAX | 3700 | 15 | 100%/93.3%/93.3% | 1491 ± 61 | 2839 ± 61 |
| 2 | — | — | 15 | 0%/0%/0% | 1461 ± 61 | 2433 ± 63 |

*mean ± standard deviation in g

Example 25 IBD Efficacy Induced by the in Ovo Administration of vHVT317 after Variant IBD Challenge at 28 Day-of-Age in SPF Chicks The aim of the study was to assess the efficacy of vHVT317 expressing the IBDV VP2 gene and ILTV gD gene administered in ovo to 18-19 day-old embryos from SPF chickens against variant IBDV challenge performed at 28 day-of-age (31 days post-vaccination).

18-19 day-old embryos from specific pathogen free (SPF) chickens were assigned to 3 groups as shown in Table 28. All birds from groups 1 & 2 (about 30 eggs/group) were vaccinated by the in ovo (SC) route with 0.05 mL of vHVT317 at the dose indicated. Embryonated eggs from group 3 were sham-inoculated with 0.05 mL of Marek's vaccine diluent. At hatch, 22 chicks per group were kept and, before challenge, all 3 groups were reduced to 20 birds. Thirty one days after vaccination (at 28 day-of-age), birds from all 3 groups were challenged with the infectious bursal disease virus (IBDV) variant Delaware E strain by the intraocular (IO) route (target dose of $10^{3.0}$ EID50 in 0.03 mL/bird). Birds from group 5 were sham challenged with TPB (tryptose phosphate broth, 0.03 mL/bird). Eleven days post-challenge, body weight and bursal weight of all birds were measured. The BB wt. ratios (bursa weight/body weight ratio×100) were calculated for all groups.

Results of protection are shown in Table 28. A clear bursal atrophy was observed in all non-vaccinated challenged birds. Protection was observed in vHVT317-vaccinated groups at the 2 tested doses.

TABLE 28

IBD efficacy induced by vHVT317 administered in ovo after challenge at 28 day-of-age with variant E IBDV strain in SPF chicks

| Group | Vaccine | Dose (PFU) | Number of birds | IBDV challenge | Mean B/B wt. ratio |
|---|---|---|---|---|---|
| 1 | vHVT317 | 2250 | 20 | Yes | 0.41 |
| 2 | vHVT317 | 3225 | 20 | Yes | 0.60 |
| 3 | — | — | 20 | Yes | 0.13 |
| 4 | — | — | 20 | No | 0.69 |

Example 26 ILT Efficacy Induced by vHVT317 Administered by the in Ovo Route Against a ILTV Challenge at D28 in SPF Chicks The aim of the study was to assess the efficacy of the vHVT317 recombinant construct expressing the IBDV VP2 gene and the ILTV gD gene administered by the in ovo route to 18-19 day-old embryos against an ILTV challenge performed on D28 (at 25 day-of-age) in SPF chickens.

18-19 day-old embryos from specific pathogen free (SPF) chickens were assigned to 2 groups as shown in Table 29. All birds from groups 1 (about 30 eggs/group) were vaccinated by the in ovo (SC) route with 0.05 mL of vHVT317 at the dose indicated. Embryonated eggs from group 2 were sham-inoculated with 0.05 mL of Marek's vaccine diluent. At hatch, 22 chicks per group were kept and, one day before challenge, both groups were reduced to 20 birds. Twenty five days after vaccination (at D28), birds from both groups were challenged with the 63140 ILTV strain administered in the infraorbital sinus ($10^{4.7}$EID50 in 0.2 mL/bird). The birds were observed for clinical signs and mortality on D28 to D38. On Study Day 38, all the remaining birds were terminated. Efficacy against ILT challenge was determined by the absence of typical ILT clinical signs such as: depression, respiratory distress associated with coughing, sneezing, rales, gasping with extended neck, with or without bloody and/or mucous discharge; dyspnea and mouth breathing; infra-orbital sinuses swelling, with or without drainage; and/or swollen conjunctiva with partial or complete closure of the eyes. Any mortality post-challenge, except due to trauma, or any clear condition that excludes the bird from the study, were considered positive for ILT.

Results of ILT protection are shown in Table 29. The results showed that most vHVT317 vaccinated birds were protected.

TABLE 29

ILT efficacy induced by vHVT317 administered by
the in ovo route after infraorbital sinus challenge
at D 28 with 63140 ILTV strain in SPF chicks

| Group | Vaccine | Dose (PFU) | Number of birds | % Protection (number protected/total) |
|---|---|---|---|---|
| 1 | vHVT317 | 2300 | 20 | 85% (17/20) |
| 2 | — | — | 20 | 5% (1/20) |

Example 29 ND Efficacy Induced by vHVT309 & vHVT310 Against a Velogenic NDV Challenge at D21 in SPF Chickens The aim of the study was to assess the efficacy of two HVT recombinant constructs (vHVT309 & vHVT310) expressing the IBDV VP2 gene and NDV F gene administered to one-day-old SPF chickens against velogenic NDV challenge performed on D21.

One-day-old SPF chicks (white leghorn) were assigned to 3 groups of birds as shown in Table 30. All birds from groups 2 and 3 were vaccinated by the subcutaneous (SC) route with 0.2 mL of vHVT309 (14 birds; group 2) or vHVT310 (15 birds; group 3) at a target dose of 2000 PFU. Birds from group 1 (5 birds) were left unvaccinated. Two birds of group 2 died on D5 for unknown reason. Twenty one days after vaccination (at D21), the blood of 10 birds from group 3 was collected for serology; then, all birds from all 3 groups were challenged with the velogenic NDV Herts 33 strain by the intramuscular (IM) route ($10^{5.0}$ EID50 in 0.2 mL/bird). All birds were observed for clinical signs during 14 days post-challenge. Birds were considered as protected if they did not die or show ND clinical signs.

Results of protection are summarized in Table 30. All non-vaccinated birds of group 1 died after challenge; all vaccinated birds were protected. The vHVT310 construct induced significant anti-NDV (mean of 3.7±0.3 (standard deviation) log 10 by ELISA (ID Screen Newcastle Disease Indirect kit from ID-VET) and mean of 3.9±0.7 log 2 by HI test) and anti-IBDV (mean of 3.7 log 10±0.2 log 10 by ELISA (ProFLOK IBD Plus ELISA kit from Zoetis) antibodies in all the 10 G3-bird serums sampled on D21.

TABLE 30

ND efficacy induced by different HVT-IBD + ND double constructs
in broiler chicks after challenge at D 21 with velogenic NDV strain

| Group | Vaccine | Dose (PFU) | Number of birds | Number of Dead & sick birds | Protection |
|---|---|---|---|---|---|
| 1 | — | — | 5 | 5 & 0 | 0% |
| 2 | vHVT309 | 2000 | 12 | 0 & 0 | 100% |
| 3 | vHVT310 | 2000 | 15 | 0 & 0 | 100% |

Example 28 IBD Efficacy Induced by vHVT309 and vHVT310 Against a Classical IBDV Challenge at D21 in SPF Chicks The aim of the study was to assess the efficacy of two HVT recombinant constructs (vHVT309 & vHVT310) expressing the IBDV VP2 gene and NDV F gene administered to one-day-old SPF chickens against a classical IBDV challenge performed on D21.

One-day-old SPF chicks (white Leghorn) were assigned to 3 groups as shown in Table 31. All birds from groups 2 & 3 (about 15 birds/group) were vaccinated by the subcutaneous (SC) route with 0.2 mL of vHVT309 (group 2) or vHVT310 (group 3) construct at a target dose of 2000 PFU. Ten birds from group 1 were left unvaccinated. Two unspecific early deaths were recorded in group 2. Twenty one days after vaccination (at D21), all birds were challenged with the classical 52/70 Faragher IBDV strain by the intraocular (IO) route ($10^{2.0}$ EID50 in 0.05 mL/bird). Eleven days post-challenge (at D32) all birds were terminated and necropsied to examine for gross bursal lesions. Bursal and body were weighted to calculate the bursa on body weight ratio. The bursa was then stored in formaldehyde for histology. Histological lesions of the bursa were scored according to the scale presented in Table 32. The severity of the challenge was validated if (1) at least 50% of the challenge controls died or showed characteristic signs of the disease, especially apathy/ruffled feathers during more than 2 days or prostration, and (2) 100% of the surviving challenge controls showed histology scores of the Bursa of Fabricius ≥3. The efficacy of the vaccine candidates was demonstrated if at least 90% of the chickens were protected. The chickens were considered protected if (1) they survived and did not show notable clinical signs of the disease, especially no apathy/ruffled feathers during more than 2 days or absence of prostration, and (2) they showed a histology score of the Bursa of Fabricius <3.

Results of protection are shown in Table 31. All controls were positive for IBD infection. Complete IBD protection was induced by vaccination with vHVT309 or vHVT310.

TABLE 31

IBD efficacy induced by two HVT constructs expressing two genes
in SPF chicks after challenge at D 21 with Faragher IBDV strain

| Group | Vaccine | Dose (log10 PFU) | Clinical signs #dead/ #sick/total | Mean Bursal/body weight ratio (*1000) | Protection |
|---|---|---|---|---|---|
| 1 | — | — | 4/1/10 | 1.7 ± 0.6** | 0% |
| 2 | vHVT309 | 3.3 | 0/0/14 | 5.4 ± 1.2 | 100% |
| 3 | vHVT310 | 3.3 | 0/0/15 | 5.5 ± 0.7 | 100% |

**mean ± standard deviation

TABLE 32

Scoring scale of histological lesions of the bursa of Fabricius*

Score Histology observation/lesions

0  No lesion, normal bursa
1  1% to 25% of the follicles show lymphoid depletion (i.e. less than 50% of depletion in 1 affected follicle), influx of heterophils in lesions
2  26% to 50% of the follicles show nearly complete lymphoid depletion (i.e. more than 75% of depletion in 1 affected follicle), affected follicles show necrosis and severe influx of heterophils may be detected
3  51% to 75% of the follicles show lymphoid depletion; affected follicles show necrosis lesions and a severe influx of heterophils is detected
4  76% to 100% of the follicles show nearly complete lymphoid depletion; hyperplasia and cyst structures are detected; affected follicles show necrosis and severe influx of heterophils is detected

TABLE 32-continued

Scoring scale of histological lesions of the bursa of Fabricius*

Score Histology observation/lesions 5   100% of the follicles show nearly complete lymphoid depletion; complete loss of follicular structure, thickened and folded epithelium, fibrosis of bursal tissue

*sourced from Monograph No. 04/2013: 0587 of European Pharmacopoeia "Avian Infectious Bursal Disease vaccine (live)

Example 29 Impact of in Ovo Administration of vHVT317 on Hatchability of SPF Chicks The aim of the study was to assess the safety of vHVT317 on hatchability when administered by the in ovo route.

The results are a compilation of data from several studies including those described in examples 23, 24, 25, and 26. Embryonated eggs at 18-19 days of incubation were inoculated either with vHVT317 at a target dose of 2000 or 3000 PFU or with Marek's disease vaccine diluent. The percentage of hatchability was evaluated for each group. Results are summarized in Table 33 and showed excellent levels of hatchability in vaccinated eggs.

TABLE 33

Hatchability after in ovo administration of vHVT317

| Group | Vaccine | Target Dose (PFU) | Number of vaccinated eggs | Number of eggs hatched | % hatchability |
|---|---|---|---|---|---|
| 1 | Diluent | — | 150 | 149 | 99.3% |
| 2 | vHVT317 | 2000 | 139 | 135 | 97.1% |
| 3 | vHVT317 | 3000 | 80 | 78 | 97.5% |

Example 30 ILT Efficacy Induced by vHVT406 Against ILTV Challenges

Example 30.1 ILT Efficacy Induced by vHVT406 Against an ILTV Challenge at D28

The aim of the study is to assess and compare the efficacy of vHVT406 recombinant construct expressing the ILTV gD gene and a commercial HVT-ILT vectored vaccine against ILT challenge.

Twelve (12) one-day-old SPF birds were assigned to each group. The birds in Groups 1-2 were vaccinated SQ with 0.2 ml per bird. After vaccination, all birds were placed into their respective units. On Day 28, all birds were challenged via the intratracheal (IT) route with Infectious Laryngotracheitis Virus (ILT), ILT-93-3 EP2. All birds were observed for 11 days post-challenge for clinical signs due to the challenge. On Day 32, tracheal and conjunctival swabs were collected from all remaining birds. Swabs were processed for q-PCR analysis. On Day 39, all remaining birds were terminated.

Results are shown in Table 34 below. The results showed that all vHVT406 vaccinated birds were protected. Surprisingly, the results also showed that good protection (100% protection) was achieved in vHVT406 group when lower dose (6,960 pfu/0.2 ml) was used when compared to the higher dose (10,340 pfu/0.2 ml) used for the commercial product Innovax HVT-ILT.

TABLE 34

Number of Birds Positive for ILT and Percent Positive by Group[1]

| Group | Vaccine | Dose/SQ[2] | # Birds | # Positive/Total # Birds | % Protection (% Infection) | % Found Dead | % Total Mortality |
|---|---|---|---|---|---|---|---|
| 1 | vHVT406 | 6,960 pfu/0.2 ml HVT | 11[3] | 0/11 | 100 | 0 | 0 |
| 2 | Innovax HVT-ILT[4] | 10,340 pfu/0.2 ml HVT | 12 | 0/12 | 100 | 0 | 0 |

[1]Birds were considered positive if they showed clinical signs for three consecutive days, including mortality or mortality after swabbing.
[2]Plaque forming units (pfu)-Subcutaneous administration (SQ); 0.20 ml per dose.
[3]One bird in vHVT406 group was excluded from the study due to paralysis.
[4]Commercial product of MSD Animal Health

Example 30.2 ILT Efficacy Induced by vHVT406 Against an ILTV Challenge at D21

The goal of the study is to assess and compare the efficacy of the vHVT406 and two commercial HVT-ILT vectored vaccines against ILT challenge.

Twelve (12) one-day-old SPF birds were assigned to each group. The randomization also assigned the isolation units where the birds were placed (12 birds per unit, one unit per group). Birds in Groups 1-3 were vaccinated SQ with 0.2 ml per bird. On Day 21, all birds in Groups 1-2 were challenged via the intratracheal (IT) route with Infectious Laryngotracheitis Virus (ILT), ILT-96-3 EP2. The birds were observed for 11 days post-challenge for clinical signs due to the challenge. On Day 25, tracheal and conjunctival swabs were collected on all remaining birds. Swab samples were processed for q-PCR. On Day 32, all remaining birds were terminated.

Results are shown in Table 35 below. The results showed that all but one vHVT406 vaccinated birds were protected. Surprisingly, the results also showed that good protection (91.7% protection) was achieved in vHVT406 group when lower dose (810 pfu/0.2 ml) was used when compared to the higher dose (1590 pfu/0.2 ml) used for the commercial product Innovax HVT-ILT to achieve the same protection level (91.7%). Further, vHVT406 provided better protection (91.7%) when used at a lower dose than the commercial product Vectormune HVT-ILT which only provided 75% protection.

TABLE 35

Number of Birds Positive for ILT and Percent Positive by Group[1]

| Group | Vaccine | Dose/SQ[2] | # Birds | # Positive/Total # Birds | % Protection (% Infection) | % Found Dead | % Total Mortality |
|---|---|---|---|---|---|---|---|
| 1 | vHVT406 | 810 pfu/0.2 ml | 12 | 1/12 | 91.7 | 0 | 0 |
| 2 | Innovax HVT-ILT | 1590 pfu/0.2 ml | 12 | 1/12 | 91.7 | 0 | 0 |

TABLE 35-continued

Number of Birds Positive for ILT and Percent Positive by Group[1]

| Group | Vaccine | Dose/SQ[2] | # Birds | # Positive/Total # Birds | % Protection (% Infection) | % Found Dead | % Total Mortality |
|---|---|---|---|---|---|---|---|
| 3 | Vectormune HVT-ILT[3] | 39,000 pfu/0.2 ml | 12 | 3/12 | 75 | 25 | 25 |

[1]Birds were considered positive if they showed clinical signs for three consecutive days, including mortality or mortality after swabbing.
[2]Plaque forming units (pfu)-Subcutaneous administration (SQ); 0.20 ml per dose.
[3]Commercial product of Ceva

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A recombinant herpesvirus of turkeys (HVT) vector comprising:
    a first heterologous polynucleotide encoding a first avian pathogen antigen; and
    a second heterologous polynucleotide encoding a second avian pathogen antigen,
    wherein the first avian pathogen is an Infectious Laryngotracheitis Virus (ILTV) glycoprotein D (gD) antigen having at least 80% sequence identity to SEQ ID NO: 17 or the first heterologous polynucleotide comprises a nucleotide sequence encoding an ILTV gD antigen that has at least 70% sequence identity to SEQ ID NO: 16,
    and wherein the second avian pathogen is an Infectious Bursal Disease Virus (IBDV) VP2 antigen or a Newcastle Disease Virus F (NDV-F) antigen.

2. The vector of claim 1, wherein the second avian pathogen is an IBDV VP2 antigen having at least 80% sequence identity to SEQ ID NO: 2 or a NDV-F antigen having at least 80% sequence identity to SEQ ID NOs: 5 and/or 22.

3. The vector of claim 1, wherein the second heterologous polynucleotide comprises a nucleotide sequence encoding an IBDV VP2 antigen that has at least 70% sequence identity to SEQ ID NO: 1 or a nucleotide sequence encoding a NDV-F antigen that has at least 70% sequence identity to SEQ ID NOs: 3, 4 or 21U.

4. The vector of claim 1, wherein the first heterologous polynucleotide is operably linked to a mCMV IE promoter, a SV40 promoter, a HHV3gB promoter, or a reverse HHV3gB promoter.

5. The vector of claim 1, wherein the first heterologous polynucleotide is operably linked to a mCMV IE or an SV40 promoter at the 5' end, and IRES or P2A at the 3' end.

6. The vector of claim 1, wherein the first and second heterologous polynucleotides are inserted in the IG1 locus or the SORF-US2 locus of the HVT genome.

7. An immunogenic composition comprising the recombinant HVT of claim 1.

8. The immunogenic composition of claim 7, wherein the second heterologous polynucleotide comprises a nucleotide sequence encoding an IBDV VP2 antigen that has at least 70% sequence identity to SEQ ID NO: 1 or a nucleotide sequence encoding a NDV-F antigen that has at least 70% sequence identity to SEQ ID NOs: 3, 4 or 21U.

9. The immunogenic composition of claim 7, wherein the second avian pathogen is an IBDV VP2 antigen having at least 80% sequence identity to SEQ ID NO: 2 or a NDV-F antigen having at least 80% sequence identity to SEQ ID NOs: 5 and/or 22.

10. The immunogenic composition of claim 7, further comprising a veterinarily acceptable carrier, excipient, vehicle, and/or adjuvant.

11. A vaccine comprising the recombinant HVT of claim 1.

12. The vaccine of claim 11, wherein the second heterologous polynucleotide comprises a nucleotide sequence encoding an IBDV VP2 antigen that has at least 70% sequence identity to SEQ ID NO: 1 or a nucleotide sequence encoding a NDV-F antigen that has at least 70% sequence identity to SEQ ID NOs: 3, 4 or 21U.

13. The vaccine of claim 11, wherein the second avian pathogen is an IBDV VP2 antigen having at least 80% sequence identity to SEQ ID NO: 2 or a NDV-F antigen having at least 80% sequence identity to SEQ ID NOs: 5 and/or 22.

14. The vaccine of claim 11, further comprising a veterinarily acceptable carrier, excipient, vehicle, and/or adjuvant.

15. A method for inducing a protective immune response in an animal against an avian pathogen, comprising:
    administering to the animal the vaccine according to claim 11.

16. The method of claim 15, wherein the animal is an avian.

* * * * *

SEQUENCE LISTING

```
<160> NUMBER OF SEQ ID NOS: 27

<210> SEQ ID NO 1
<211> LENGTH: 1359
<212> TYPE: DNA
<213> ORGANISM: artificial sequence
<220> FEATURE:
<223> OTHER INFORMATION: DNA encoding IBDV VP2

<400> SEQUENCE: 1
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtctttttc     180
cctggattcc ctggctcaat tgtgggtgct cactacacac tgcagagcaa tgggaactac     240
aagttcgatc agatgctcct gactgcccag aacctaccgg ccagctacaa ctactgcaga     300
ctagtgagtc ggagtctcac agtgaggtca agcacactcc ctggtggcgt ttatgcacta     360
aacggcacca taaacgccgt gaccttccaa ggaagcctga gtgaactgac agatgttagc     420
tacaatgggt tgatgtctgc aacagccaac atcaacgaca aaattgggaa tgtcctggta     480
ggggaagggg tcactgtcct cagcctaccc acatcatatg atcttgggta tgtgaggctt     540
ggtgacccca ttcccgctat agggcttgac ccaaaaatgg tagctacatg cgacagcagt     600
gacaggccca gagtctacac cataactgca gccgatgatt accaattctc atcacagtac     660
caaccaggtg gggtaacaat cacactgttc tcagccaaca ttgatgctat cacaagcctc     720
agcattgggg gagagctcgt gtttcaaaca agcgtccaag gccttgtact gggcgccacc     780
atctacctta taggctttga tgggactgcg gtaatcacca gagctgtagc cgcagataat     840
gggctgacgg ccggcaccga caatcttatg ccattcaatc ttgtcattcc aaccaatgag     900
ataacccagc caatcacatc catcaaactg gagatagtga cctccaaaag tggtggtcag     960
gcaggggatc agatgtcatg gtcggcaagt gggagcctag cagtgacgat ccatggtggc    1020
aactatccag ggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggagg                           1359

<210> SEQ ID NO 2
```

```
<211> LENGTH: 453
<212> TYPE: PRT
<213> ORGANISM: artificial sequence
<220> FEATURE:
<223> OTHER INFORMATION: IBDV VP2 protein

<400> SEQUENCE: 2

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380
```

-continued

```
Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450

<210> SEQ ID NO 3
<211> LENGTH: 1659
<212> TYPE: DNA
<213> ORGANISM: artificial sequence
<220> FEATURE:
<223> OTHER INFORMATION: NDV-Fopt VIId of pFSV40VP2 and pFIRESVP2

<400> SEQUENCE: 3
atgggcagca agcccagcac aagaatccca gcccccctga tgctgatcac ccgcatcatg      60
ctgatcctgg gctgcatcag acccacaagc tccctggatg gacgccccct ggccgctgcc     120
ggcatcgtgg tgaccggcga caaggccgtg aacgtgtaca ccagcagcca gaccggcagc     180
atcatcgtga agctgctgcc caacatgccc agagacaaag aggcctgcgc caaggccccc     240
ctggaagcct acaacagaac cctgaccacc ctgctgaccc ccctgggcga cagcatcaga     300
aagatccagg gctccgtgag cacaagcggc ggaggaaagc agggcagact gatcggcgcc     360
gtgatcggca gcgtggccct gggagtggct acagctgccc agattaccgc tgcagccgcc     420
ctgatccagg ccaaccagaa cgccgccaac atcctgagac tgaaagagag cattgccgcc     480
accaacgagg ccgtgcacga agtgaccgac ggcctgagcc agctgtccgt ggccgtgggc     540
aagatgcagc agttcgtgaa cgaccagttc aacaacaccg ccagagagct ggactgcatc     600
aagatcaccc agcaggtggg cgtggagctg aacctgtacc tgaccgagct gaccacagtg     660
ttcggccccc agatcacaag cccagccctg acacagctga ccatccaggc cctgtacaac     720
ctggctggcg gcaacatgga ctatctgctg acaaagctgg gaatcggcaa caaccagctg     780
tccagcctga tcggaagcgg cctgatcacc ggctacccca tcctgtacga cagccagaca     840
cagctgctgg gcatccaggt gaacctgccc agcgtgggca acctgaacaa catgcgcgcc     900
acctacctgg aaaccctgag cgtgtccacc accaagggct acgccagcgc cctggtgccc     960
aaggtggtga cacaggtggg cagcgtgatc gaggaactgg acaccagcta ctgcatcgag    1020
agcgacctgg acctgtactg caccagaatc gtgaccttcc caatgagccc cggcatctac    1080
agctgcctga gcggcaacac cagcgcctgc atgtacagca agaccgaagg cgcactgaca    1140
acaccctaca tggccctgaa gggaagcgtg atcgccaact gcaagatcac cacctgcaga    1200
tgcaccgacc ccccaggcat catcagccag aactacggcg aggccgtgag cctgatcgat    1260
cgccattcct gtaacgtgct gtccctggac ggcatcacac tgagactgag cggcgagttc    1320
gatgccacct accagaagaa catcagcatc ctggacagcc aggtgatcgt gaccggcaac    1380
ctggacatca gcaccgagct gggcaacgtg aataacagca tcagcaacgc cctggacaga    1440
ctggccgaga gcaacagcaa gctggaaaaa gtgaacgtgc gcctgacatc cacttccgct    1500
ctgatcacct acatcgtgct gaccgtgatc agcctggtgt tcggcgccct gagcctggtg    1560
ctggcctgct acctgatgta caagcagaag gcccagcaga aaccctgct gtggctgggc     1620
```
aacaacaccc tggaccagat gagagccacc accagagcc       1659

<210> SEQ ID NO 4
<211> LENGTH: 1659
<212> TYPE: DNA
<213> ORGANISM: artificial sequence
<220> FEATURE:
<223> OTHER INFORMATION: NDV-F wildtype VIId of pFP2AVP2

<400> SEQUENCE: 4

| | | |
|---|---|---|
| atgggctcca aaccttctac caggatccca gcacctctga tgctgatcac ccggattatg | 60 |
| ctgatattgg gctgtatccg tccgacaagc tctcttgacg gcaggcctct tgcagctgca | 120 |
| ggaattgtag taacaggaga taaggcagtc aatgtataca cttcgtctca gacagggtca | 180 |
| atcatagtca agttgctccc gaatatgccc agggataagg aggcgtgtgc aaaagcccca | 240 |
| ttagaggcat ataacagaac actgactact tgctcactc ctcttggcga ctccatccgc | 300 |
| aagatccaag gtctgtgtc cacatctgga ggaggcaagc aaggccgcct gataggtgct | 360 |
| gttattggca gtgtagctct tggggttgca acagcggcac agataacagc agctgcggcc | 420 |
| ctaatacaag ccaaccagaa tgccgccaac atcctccggc ttaaggagag cattgctgca | 480 |
| accaatgaag ctgtgcatga agtcaccgac ggattatcac aactatcagt ggcagttggg | 540 |
| aagatgcagc agtttgtcaa tgaccagttt aataatacgg cgcgagaatt ggactgtata | 600 |
| aaaatcacac aacaggttgg tgtagaactc aacctatacc taactgaatt gactacagta | 660 |
| ttcgggccac agatcacctc ccctgcatta actcagctga ccatccaggc acttatrat | 720 |
| ttagctggtg gcaatatgga ttacttatta actaagttag gtatagggaa caatcaactc | 780 |
| agctcgttaa ttggtagcgg cctgatcact ggttaccctca tactgtatga ctcacagact | 840 |
| caactcttgg gcatacaagt gaatttaccc tcagtcggga acttaaataa tatgcgtgcc | 900 |
| acctatttgg agaccttatc tgtaagtaca accaaaggat atgcctcagc acttgtcccg | 960 |
| aaagtagtga cacaagtcgg ttccgtgata gaagagcttg acacctcata ctgtatagag | 1020 |
| tccgatctgg atttatattg tactagaata gtgacattcc ccatgtcccc aggtattat | 1080 |
| tcctgtttga gcggcaacac atcagcttgc atgtattcaa agactgaagg cgcactcact | 1140 |
| acgccgtata tggcccttaa aggctcagtt attgccaatt gtaaaataac aacatgtaga | 1200 |
| tgtacagacc ctcctggtat catatcgcaa aattatggag aagctgtatc cctgatagat | 1260 |
| agacattcgt gcaatgtctt atcattagac gggataactc taaggctcag tggggaattt | 1320 |
| gatgcaactt atcaaaagaa catctcaata ctagattctc aagtcatcgt gacaggcaat | 1380 |
| cttgatatat caactgaact tggaaacgtc aacaattcaa tcagcaatgc cttggatagg | 1440 |
| ttggcagaaa gcaacagcaa gctagaaaaa gtcaatgtca gactaaccag cacatctgct | 1500 |
| ctcattacct atattgttct aactgtcatt tctctagttt tcggtgcact tagtctggtg | 1560 |
| ttagcgtgtt acctgatgta caaacagaag gcacaacaaa agaccttgct atggcttggg | 1620 |
| aataatacc tcgatcagat gagagccact acaagagca | 1659 |

<210> SEQ ID NO 5
<211> LENGTH: 553
<212> TYPE: PRT
<213> ORGANISM: artificial sequence
<220> FEATURE:
<223> OTHER INFORMATION: NDV-F VIId

<400> SEQUENCE: 5

Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Ala Gly Ile Val Val Thr Gly Asp Lys
            35                  40                  45

Ala Val Asn Val Tyr Thr Ser Ser Gln Thr Gly Ser Ile Ile Val Lys
50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
            115                 120                 125

Val Ala Thr Ala Ala Gln Ile Thr Ala Ala Ala Leu Ile Gln Ala
            130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
            195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
            245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
            275                 280                 285

Leu Pro Ser Val Gly Asn Leu Asn Asn Met Arg Ala Thr Tyr Leu Glu
            290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
            370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
            405                 410                 415

Ser Leu Ile Asp Arg His Ser Cys Asn Val Leu Ser Leu Asp Gly Ile

```
                420             425             430
Thr Leu Arg Leu Ser Gly Glu Phe Asp Ala Thr Tyr Gln Lys Asn Ile
            435             440             445

Ser Ile Leu Asp Ser Gln Val Ile Val Thr Gly Asn Leu Asp Ile Ser
        450             455             460

Thr Glu Leu Gly Asn Val Asn Asn Ser Ile Ser Asn Ala Leu Asp Arg
465             470             475             480

Leu Ala Glu Ser Asn Ser Lys Leu Glu Lys Val Asn Val Arg Leu Thr
                485             490             495

Ser Thr Ser Ala Leu Ile Thr Tyr Ile Val Leu Thr Val Ile Ser Leu
            500             505             510

Val Phe Gly Ala Leu Ser Leu Val Leu Ala Cys Tyr Leu Met Tyr Lys
        515             520             525

Gln Lys Ala Gln Gln Lys Thr Leu Leu Trp Leu Gly Asn Asn Thr Leu
            530             535             540

Asp Gln Met Arg Ala Thr Thr Arg Ala
545                 550

<210> SEQ ID NO 6
<211> LENGTH: 1391
<212> TYPE: DNA
<213> ORGANISM: artificial sequence
<220> FEATURE:
<223> OTHER INFORMATION: mCMV IE promoter

<400> SEQUENCE: 6
aactccgccc gttttatgac tagaaccaat agttttaat gccaaatgca ctgaaatccc      60
ctaatttgca aagccaaacg ccccctatgt gagtaatacg gggactttt acccaatttc     120 ccaagcggaa agcccctaa tacactcata tggcatatga atcagcacgg tcatgcactc     180
taatggcggc ccatagggac tttccacata ggggcgttc accatttccc agcataggg      240 tggtgactca atggccttta cccaagtaca ttgggtcaat gggaggtaag ccaatgggt     300 tttcccatta ctggcaagca cactgagtca atgggacttt ccactgggt tttgcccaag    360 tacattgggt caatgggagg tgagccaatg gaaaaaccc attgctgcca agtacactga     420
ctcaataggg actttccaat gggttttttcc attgttggca agcatataag gtcaatgtgg   480
gtgagtcaat agggactttc cattgtattc tgcccagtac ataaggtcaa tagggggtga    540
atcaacagga aagtcccatt ggagccaagt acactgcgtc aatagggact ttccattggg    600
ttttgcccag tacataaggt caatagggga tgagtcaatg gaaaaaccc attggagcca    660 agtacactga ctcaataggg actttccatt gggttttgcc cagtacataa ggtcaatagg    720
gggtgagtca acaggaaagt cccattggag ccaagtacat gagtcaata gggactttcc    780 aatgggtttt gcccagtaca taaggtcaat gggaggtaag ccaatgggtt tttcccatta    840
ctggcacgta tactgagtca ttagggactt ccaatgggt tttgcccagt acataaggtc     900 aatagggtg aatcaacagg aaagtcccat tggagccaag tacactgagt caataggggac  960 tttccattgg ttttgccca gtacaaaagg tcataggggg gtgagtcaat gggttttcc    1020 cattattggc acgtacataa ggtcaatagg ggtgagtcat gggttttc cagccaattt    1080 aattaaaacg ccatgtactt tcccaccatt gacgtcaatg gctattgaa actaatgcaa    1140 cgtgaccttt aaacggtact ttcccatagc tgattaatgg gaaagtaccg ttctcgagcc    1200
aatacacgtc aatgggaagt gaaagggcag ccaaaacgta acaccgcccc ggttttcccc    1260
tggaaattcc atattggcac gcattctatt ggctgagctg cgttctacgt gggtataaga   1320
```

```
ggcgcgacca gcgtcggtac cgtcgcagtc ttcggtctga ccaccgtaga acgcagagct    1380
cctcgctgca g                                                        1391

<210> SEQ ID NO 7
<211> LENGTH: 345
<212> TYPE: DNA
<213> ORGANISM: artificial sequence
<220> FEATURE:
<223> OTHER INFORMATION: SV40 Promoter for NDV F

<400> SEQUENCE: 7
gctgtggaat gtgtgtcagt tagggtgtgg aaagtcccca ggctcccag caggcagaag      60 tatgcaaagc atgcatctca attagtcagc aaccaggtgt ggaaagtccc caggctcccc    120
agcaggcaga agtatgcaaa gcatgcatct caattagtca gcaaccatag tcccgccccct    180 aactccgccc atcccgcccc taactccgcc cagttccgcc cattctccgc cccatggctg    240 actaatttt tttatttatg cagaggccga ggccgcctcg gcctctgagc tattccagaa      300
gtagtgagga ggcttttttg gaggcctagg cttttgcaaa aagct                    345

<210> SEQ ID NO 8
<211> LENGTH: 199
<212> TYPE: DNA
<213> ORGANISM: artificial sequence
<220> FEATURE:
<223> OTHER INFORMATION: SV40 Poly A

<400> SEQUENCE: 8
ggggatccag acatgataag atacattgat gagtttggac aaaccacaac tagaatgcag     60
tgaaaaaaat gctttatttg tgaaatttgt gatgctattg ctttatttgt aaccattata   120
agctgcaata aacaagttaa caacaacaat tgcattcatt ttatgtttca ggttcagggg   180
gaggtgtggg aggttttttt                                              199

<210> SEQ ID NO 9
<211> LENGTH: 154
<212> TYPE: DNA
<213> ORGANISM: artificial sequence
<220> FEATURE:
<223> OTHER INFORMATION: Synthetic Poly A

<400> SEQUENCE: 9
aataaaatat ctttattttc attacatctg tgtgttggtt ttttgtgtga atcgatagta     60
ctaacatacg ctctccatca aaacaaaacg aaacaaaaca aactagcaaa ataggctgtc   120
cccagtgcaa gtgcaggtgc cagaacattt ctct                              154

<210> SEQ ID NO 10
<211> LENGTH: 563
<212> TYPE: DNA
<213> ORGANISM: artificial sequence
<220> FEATURE:
<223> OTHER INFORMATION: IRES of pFIRESVP2

<400> SEQUENCE: 10
cccccccccc taacgttact ggccgaagcc gcttggaata aggccggtgt gcgtttgtct     60
atatgttatt ttccaccata ttgccgtctt ttggcaatgt gagggcccgg aaacctggcc   120
ctgtcttctt gacgagcatt cctagggggt ctttcccctct cgccaaagga atgcaaggtc   180
tgttgaatgt cgtgaaggaa gcagttcctc tggaagcttc ttgaagacaa acaacgtctg   240
```

```
tagcgaccct ttgcaggcag cggaacccccc cacctggcga caggtgcctc tgcggccaaa    300
agccacgtgt ataagataca cctgcaaagg cggcacaacc ccagtgccac gttgtgagtt    360
ggatagttgt ggaaagagtc aaatggctct cctcaagcgt attcaacaag gggctgaagg    420
atgcccagaa gtaccccat tgtatgggat ctgatctggg gcctcggtgc acatgcttta    480
catgtgttta gtcgaggtta aaaaacgtct aggccccccg aaccacgggg acgtggtttt    540
cctttgaaaa acacgatgat aat                                            563

<210> SEQ ID NO 11
<211> LENGTH: 66
<212> TYPE: DNA
<213> ORGANISM: artificial sequence
<220> FEATURE:
<223> OTHER INFORMATION: P2A of pFP2AVP2

<400> SEQUENCE: 11
ggctccggcg ccaccaactt ctccctgctc aagcaggccg gcgacgtgga ggagaaccct    60
ggacct                                                               66

<210> SEQ ID NO 12
<211> LENGTH: 3807
<212> TYPE: DNA
<213> ORGANISM: artificial sequence
<220> FEATURE:
<223> OTHER INFORMATION: pFSV40VP2 for vHVT309
<220> FEATURE:
<221> NAME/KEY: IBDV VP2
<222> LOCATION: (1)..(1362)
<220> FEATURE:
<221> NAME/KEY: SV40 Poly A
<222> LOCATION: (1383)..(1594)
<220> FEATURE:
<221> NAME/KEY: S

```
gggctgacgg ccggcaccga caatcttatg ccattcaatc ttgtcattcc aaccaatgag    900
ataacccagc caatcacatc catcaaactg gagatagtga cctccaaaag tggtggtcag    960 gcagggatc agatgtcatg gtcggcaagt gggagcctag cagtgacgat ccatggtggc    1020
aactatccag gggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggaggt aagcttgatc tagagcggcc    1380
gcggggatcc agacatgata agatacattg atgagtttgg acaaaccaca actagaatgc    1440
agtgaaaaaa atgctttatt tgtgaaattt gtgatgctat tgctttattt gtaaccatta    1500
taagctgcaa taaacaagtt aacaacaaca attgcattca ttttatgttt caggttcagg    1560
gggaggtgtg ggaggttttt tcggatcctc tagagtcgac gaattcgagc tcggtacagc    1620
ttggctgtgg aatgtgtgtc agttaggggtg tggaaagtcc ccaggctccc cagcaggcag    1680
aagtatgcaa agcatgcatc tcaattagtc agcaaccagg tgtggaaagt ccccaggctc    1740
cccagcaggc agaagtatgc aaagcatgca tctcaattag tcagcaacca tagtcccgcc    1800
cctaactccg cccatcccgc ccctaactcc gcccagttcc gcccattctc cgccccatgg    1860
ctgactaatt ttttttattt atgcagaggc cgaggccgcc tcggcctctg agctattcca    1920
gaagtagtga ggaggctttt ttggaggcct aggcttttgc aaaaagctgc ggccgccacc    1980
atgggcagca agcccagcac aagaatccca gccccctga tgctgatcac ccgcatcatg    2040
ctgatcctgg gctgcatcag acccacaagc tccctggatg acgcccct ggccgctgcc    2100 ggcatcgtgg tgaccggcga caaggccgtg aacgtgtaca ccagcagcca gaccggcagc    2160
atcatcgtga agctgctgcc caacatgccc agagacaaag aggcctgcgc caaggccccc    2220
ctggaagcct acaacagaac cctgaccacc ctgctgaccc cctgggcga cagcatcaga    2280 aagatccagg gctccgtgag cacaagcggc ggaggaaagc agggcagact gatcggcgcc    2340
gtgatcggca gcgtggccct gggagtggct acagctgccc agattaccgc tgcagccgcc    2400
ctgatccagg ccaaccagaa cgccgccaac atcctgagac tgaaagagag cattgccgcc    2460
accaacgagg ccgtgcacga agtgaccgac ggcctgagcc agctgtccgt ggccgtgggc    2520
aagatgcagc agttcgtgaa cgaccagttc aacaacaccg ccagagagct ggactgcatc    2580
aagatcaccc agcaggtggg cgtggagctg aacctgtacc tgaccgagct gaccacagtg    2640
ttcggccccc agatcacaag cccagcctg acacagctga ccatccaggc cctgtacaac    2700
ctggctggcg gcaacatgga ctatctgctg acaaagctgg aatcggcaa caaccagctg    2760 tccagcctga tcggaagcgg cctgatcacc ggctacccca tcctgtacga cagccagaca    2820
cagctgctgg gcatccaggt gaacctgccc agcgtgggca acctgaacaa catgcgcgcc    2880
acctacctgg aaaccctgag cgtgtccacc accaagggct acgccagcgc cctggtgccc    2940
aaggtggtga cacaggtggg cagcgtgatc gaggaactgg acaccagcta ctgcatcgag    3000
agcgacctgg acctgtactg caccagaatc gtgaccttcc caatgagccc cggcatctac    3060
agctgcctga gcggcaacac cagcgcctgc atgtacagca agaccgaagg cgcactgaca    3120
acaccctaca tggcccctgaa gggaagcgtg atcgccaact gcaagatcac cacctgcaga    3180
tgcaccgacc ccccaggcat catcagccag aactacggcg aggccgtgag cctgatcgat    3240
```

```
cgccattcct gtaacgtgct gtccctggac ggcatcacac tgagactgag cggcgagttc    3300
gatgccacct accagaagaa catcagcatc ctggacagcc aggtgatcgt gaccggcaac    3360
ctggacatca gcaccgagct gggcaacgtg aataacagca tcagcaacgc cctggacaga    3420
ctggccgaga gcaacagcaa gctggaaaaa gtgaacgtgc gcctgacatc cacttccgct    3480
ctgatcacct acatcgtgct gaccgtgatc agcctggtgt tcggcgccct gagcctggtg    3540
ctggcctgct acctgatgta caagcagaag gcccagcaga aaaccctgct gtggctgggc    3600
aacaacaccc tggaccagat gagagccacc accagagcct gatgagcggc cgcaataaaa    3660
tatctttatt ttcattacat ctgtgtgttg gttttttgtg tgaatcgata gtactaacat    3720
acgctctcca tcaaaacaaa acgaaacaaa acaaactagc aaaataggct gtccccagtg    3780
caagtgcagg tgccagaaca tttctct                                       3807
```

<210> SEQ ID NO 13
<211> LENGTH: 3809
<212> TYPE: DNA
<213> ORGANISM: artificial sequence
<220> FEATURE:
<223> OTHER INFORMATION: pFIRESVP2 for vHVT310
<220> FEATURE:
<221> NAME/KEY: IBDV VP2
<222> LOCATION: (1)..(1362)
<220> FEATURE:
<221> NAME/KEY: IRES
<222> LOCATION: (1363)..(1925)
<220> FEATURE:
<221> NAME/KEY: NDV-Fopt VIId
<222> LOCATION: (1929)..(3590)
<220> FEATURE:
<221> NAME/KEY: SV40 Poly A
<222> LOCATION: (3611)..(3809)

<400> SEQUENCE: 13

```
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtcttttc     180 cctggattcc ctggctcaat gtgtggtgct cactacacac tgcagagcaa tgggaactac     240
aagttcgatc agatgctcct gactgcccag aacctaccgg ccagctacaa ctactgcaga     300
ctagtgagtc ggagtctcac agtgaggtca agcacactcc ctggtggcgt ttatgcacta     360
aacggcacca taaacgccgt gaccttccaa ggaagcctga gtgaactgac agatgttagc     420
tacaatgggt tgatgtctgc aacagccaac atcaacgaca aaattgggaa tgtcctggta     480
ggggaagggg tcactgtcct cagcctaccc acatcatatg atcttgggta tgtgaggctt     540
ggtgacccca ttcccgctat agggcttgac ccaaaaatgg tagctacatg cgacagcagt     600
gacaggccca gagtctacac cataactgca gccgatgatt accaattctc atcacagtac     660
caaccaggtg gggtaacaat cacactgttc tcagccaaca ttgatgctat acaagccctc     720
agcattgggg gagagctcgt gtttcaaaca gcgtccaag gccttgtact gggcgccacc     780
atctaccctt aggctttga tgggactgcg gtaatcacca gagctgtagc cgcagataat     840
gggctgacgg ccggcaccga caatcttatg ccattcaatc ttgtcattcc aaccaatgag     900
ataacccagc caatcacatc catcaaactg gagatagtga cctccaaaag tggtggtcag     960
gcaggggatc agatgtcatg gtcggcaagt gggagcctag cagtgacgat ccatggtggc    1020
aactatccag gggccctccg tcccgtcaca ctagtagcct acgaaagagt ggcaacagga    1080
```

-continued

```
tccgtcgtta cggtcgctgg ggtgagtaac ttcgagctga ttccaaatcc tgaactagca      1140
aagaacctgg ttacagaata cggccgattt gacccaggag ccatgaacta cacaaaattg      1200
atactgagtg agagggaccg tcttggcatc aagaccgtct ggccaacaag ggagtacact      1260
gattttcgtg agtacttcat ggaggtggcc gacctcaact ctcccctgaa gattgcagga      1320
gcatttggct tcaaagacat aatccgggct ataaggaggt aaccccccccc cctaacgtta      1380 ctggccgaag ccgcttggaa taaggccggt gtgcgtttgt ctatatgtta ttttccacca      1440
tattgccgtc ttttggcaat gtgagggccc ggaaacctgg ccctgtcttc ttgacgagca      1500
ttcctagggg tctttcccct ctcgccaaag gaatgcaagg tctgttgaat gtcgtgaagg      1560
aagcagttcc tctggaagct tcttgaagac aaacaacgtc tgtagcgacc ctttgcaggc      1620
agcggaaccc cccacctggc gacaggtgcc tctgcggcca aaagccacgt gtataagata      1680
cacctgcaaa ggcggcacaa ccccagtgcc acgttgtgag ttggatagtt gtggaaagag      1740
tcaaatggct ctcctcaagc gtattcaaca aggggctgaa ggatgcccag aaggtacccc      1800
attgtatggg atctgatctg ggcctcggt gcacatgctt tacatgtgtt tagtcgaggt       1860
taaaaaacgt ctaggccccc cgaaccacgg ggacgtggtt ttcctttgaa aaacacgatg      1920
ataataccat gggcagcaag cccagcacaa gaatcccagc cccctgatg ctgatcaccc       1980 gcatcatgct gatcctgggc tgcatcagac ccacaagctc cctggatgga cgccccctgg      2040
ccgctgccgg catcgtggtg accggcgaca aggccgtgaa cgtgtacacc agcagccaga      2100
ccggcagcat catcgtgaag ctgctgccca acatgcccag agacaaagag gcctgcgcca      2160 aggccccccct ggaagcctac aacagaaccc tgaccaccct gctgaccccc ctgggcgaca     2220
gcatcagaaa gatccagggc tccgtgagca aagcggcgg aggaaagcag ggcagactga       2280
tcggcgccgt gatcggcagc gtggccctgg gagtggctac agctgcccag attaccgctg      2340
cagccgccct gatccaggcc aaccagaacg ccgccaacat cctgagactg aaagagagca      2400
ttgccgccac caacgaggcc gtgcacgaag tgaccgacgg cctgagccag ctgtccgtgg      2460
ccgtgggcaa gatgcagcag ttcgtgaacg accagttcaa caacaccgcc agagagctgg      2520
actgcatcaa gatcacccag caggtgggcg tggagctgaa cctgtacctg accgagctga      2580
ccacagtgtt cggcccccag atcacaagcc cagccctgac acagctgacc atccaggccc      2640
tgtacaacct ggctggcggc aacatggact atctgctgac aaagctggga atcggcaaca      2700
accagctgtc cagcctgatc ggaagcggcc tgatcaccgg ctaccccatc ctgtacgaca      2760
gccagacaca gctgctgggc atccaggtga acctgcccag cgtgggcaac ctgaacaaca      2820
tgcgcgccac ctacctggaa accctgagcg tgtccaccac caagggctac gccagcgccc      2880
tggtgcccaa ggtggtgaca caggtgggca gcgtgatcga ggaactggac accagctact      2940
gcatcgagag cgacctggac ctgtactgca ccagaatcgt gaccttccca atgagccccg      3000
gcatctacag ctgcctgagc ggcaacacca gcgcctgcat gtacagcaag accgaaggcg      3060
cactgacaac accctacatg gccctgaagg gaagcgtgat cgccaactgc aagatcacca      3120
cctgcagatg caccgacccc ccaggcatca tcagccagaa ctacggcgag gccgtgagcc      3180
tgatcgatcg ccattcctgt aacgtgctgt ccctggacgg catcacactg agactgagcg      3240
gcgagttcga tgccacctac cagaagaaca tcagcatcct ggacagccag gtgatcgtga      3300
ccggcaacct ggacatcagc accgagctgg gcaacgtgaa taacagcatc agcaacgccc      3360
tggacagact ggccgagagc aacagcaagc tggaaaaagt gaacgtgcgc ctgacatcca      3420
cttccgctct gatcacctac atcgtgctga ccgtgatcag cctggtgttc ggcgccctga      3480
```

| gcctggtgct ggcctgctac ctgatgtaca agcagaaggc ccagcagaaa accctgctgt | 3540 |
| ggctgggcaa caacccctg accagatga gagccaccac cagagcctga gcttgatcta | 3600 |
| gagcggccgc ggggatccag acatgataag atacattgat gagtttggac aaaccacaac | 3660 |
| tagaatgcag tgaaaaaaat gctttatttg tgaaatttgt gatgctattg ctttatttgt | 3720 |
| aaccattata agctgcaata aacaagttaa caacaacaat tgcattcatt ttatgtttca | 3780 |
| ggttcagggg gaggtgtggg aggtttttt | 3809 |

<210> SEQ ID NO 14
<211> LENGTH: 3309
<212> TYPE: DNA
<213> ORGANISM: artificial sequence
<220> FEATURE:
<223> OTHER INFORMATION: pFP2AVP2 for vHVT311
<220> FEATURE:
<221> NAME/KEY: IBDV VP2
<222> LOCATION: (1)..(1359)
<220> FEATURE:
<221> NAME/KEY: P2A
<222> LOCATION: (1360)..(1425)
<220> FEATURE:
<221> NAME/KEY: NDV-F wildtype VIId
<222> LOCATION: (1426)..(3087)
<220> FEATURE:
<221> NAME/KEY: SV40 Poly A
<222> LOCATION: (3111)..(3309)

<400> SEQUENCE: 14

```
atgacaaacc tgcaagatca aacccaacag attgttccgt tcatacggag ccttctgatg     60
ccaacaaccg gaccggcgtc cattccggac gacaccctgg agaagcacac tctcaggtca    120
gagacctcga cctacaattt gactgtgggg gacacagggt cagggctaat tgtctttttc    180
cctggattcc ctggctcaat tgtgggtgct cactacacac tgcagagcaa tgggaactac    240
aagttcgatc agatgctcct gactgcccag aacctaccgg ccagctacaa ctactgcaga    300
ctagtgagtc ggagtctcac agtgaggtca agcacactcc ctggtggcgt ttatgcacta    360
aacggcacca taaacgccgt gaccttccaa ggaagcctga gtgaactgac agatgttagc    420
tacaatgggt tgatgtctgc aacagccaac atcaacgaca aaattgggaa tgtcctggta    480
ggggaagggg tcactgtcct cagcctaccc acatcatatg atcttgggta tgtgaggctt    540
ggtgacccca ttcccgctat agggcttgac ccaaaaatgg tagctacatg cgacagcagt    600
gacaggccca gagtctacac cataactgca gccgatgatt accaattctc atcacagtac    660
caaccaggtg ggggtaacat cacactgttc tcagccaaca ttgatgctat cacaagcctc    720
agcattgggg gagagctcgt gtttcaaaca agcgtccaag gccttgtact gggcgccacc    780
atctacctta taggctttga tgggactgcg gtaatcacca gagctgtagc cgcagataat    840
gggctgacgg ccggcaccga caatcttatg ccattcaatc ttgtcattcc aaccaatgag    900
ataacccagc caatcacatc catcaaactg gagatagtga cctccaaaag tggtggtcag    960
gcaggggatc agatgtcatg gtcggcaagt gggagcctag cagtgacgat ccatggtggc   1020
aactatccag ggccctccg tcccgtcaca ctagtagcct acgaaagagt ggcaacagga   1080
tccgtcgtta cggtcgctgg ggtgagtaac ttcgagctga ttccaaatcc tgaactagca   1140
aagaacctgg ttacagaata cggccgattt gacccaggag ccatgaacta cacaaaattg   1200
atactgagtg agagggaccg tcttggcatc aagaccgtct ggccaacaag ggagtacact   1260
gattttcgtg agtacttcat ggaggtggcc gacctcaact ctcccctgaa gattgcagga   1320
```

```
gcatttggct tcaaagacat aatccgggct ataaggaggg gctccggcgc caccaacttc   1380
tccctgctca agcaggccgg cgacgtggag gagaaccctg gacctatggg ctccaaacct   1440
tctaccagga tcccagcacc tctgatgctg atcacccgga ttatgctgat attgggctgt   1500
atccgtccga caagctctct tgacggcagg cctcttgcag ctgcaggaat tgtagtaaca   1560
ggagataagg cagtcaatgt atacacttcg tctcagacag ggtcaatcat agtcaagttg   1620
ctcccgaata tgcccaggga taaggaggcg tgtgcaaaag ccccattaga ggcatataac   1680
agaacactga ctactttgct cactcctctt ggcgactcca tccgcaagat ccagggtct   1740
gtgtccacat ctggaggagg caagcaaggc cgcctgatag gtgctgttat tggcagtgta   1800
gctcttgggg ttgcaacagc ggcacagata acagcagctg cggccctaat acaagccaac   1860
cagaatgccg ccaacatcct ccggcttaag gagagcattg ctgcaaccaa tgaagctgtg   1920
catgaagtca ccgacggatt atcacaacta tcagtggcag ttgggaagat gcagcagttt   1980
gtcaatgacc agtttaataa tacggcgcga gaattggact gtataaaaat cacacaacag   2040
gttggtgtag aactcaacct ataccta act gaattgacta cagtattcgg gccacagatc   2100
acctccctg cattaactca gctgaccatc caggcacttt ataatttagc tggtggcaat   2160
atggattact tattaactaa gttaggtata gggaacaatc aactcagctc gttaattggt   2220
agcggcctga tcactggtta ccctatactg tatgactcac agactcaact cttgggcata   2280
caagtgaatt taccctcagt cgggaactta ataatatgc gtgccaccta tttggagacc   2340
ttatctgtaa gtacaaccaa aggatatgcc tcagcacttg tcccgaaagt agtgacacaa   2400
gtcggttccg tgatagaaga gcttgacacc tcatactgta tagagtccga tctggattta   2460
tattgtacta gaatagtgac attccccatg tccccaggta tttattcctg tttgagcggc   2520
aacacatcag cttgcatgta ttcaaagact gaaggcgcac tcactacgcc gtatatggcc   2580
cttaaaggct cagttattgc caattgtaaa ataacaacat gtagatgtac agaccctcct   2640
ggtatcatat cgcaaaatta tggagaagct gtatccctga tagatagaca ttcgtgcaat   2700
gtcttatcat tagacgggat aactctaagg ctcagtgggg aatttgatgc aacttatcaa   2760
aagaacatct caatactaga ttctcaagtc atcgtgacag gcaatcttga tatatcaact   2820
gaacttggaa acgtcaacaa ttcaatcagc aatgccttgg ataggttggc agaaagcaac   2880
agcaagctag aaaaagtcaa tgtcagacta accagcacat ctgctctcat tacctatatt   2940
gttctaactg tcatttctct agttttcggt gcacttagtc tggtgttagc gtgttacctg   3000
atgtacaaac agaaggcaca acaaaagacc ttgctatggc ttgggaataa taccctcgat   3060
cagatgagag ccactacaag agcatgataa gcttgatcta gagcggccgc ggggatccag   3120
acatgataag atacattgat gagtttggac aaaccacaac tagaatgcag tgaaaaaaat   3180
gctttatttg tgaaatttgt gatgctattg ctttatttgt aaccattata agctgcaata   3240
aacaagttaa caacaacaat tgcattcatt ttatgtttca ggttcagggg gaggtgtggg   3300
aggttttttt                                                         3309
```

<210> SEQ ID NO 15
<211> LENGTH: 3440
<212> TYPE: DNA
<213> ORGANISM: artificial sequence
<220> FEATURE:
<223> OTHER INFORMATION: pVP2IRESgD for vHVT317
<220> FEATURE:
<221> NAME/KEY: IBDV VP2
<222> LOCATION: (1)..(1362)
<220> FEATURE:

```
<221> NAME/KEY: IRES
<222> LOCATION: (1363)..(1925)
<220> FEATURE:
<221> NAME/KEY: ILTV-gD
<222> LOCATION: (1929)..(3233)
<220> FEATURE:
<221> NAME/KEY: SV40 Poly A
<222> LOCATION: (3242)..(3440)

<400> SEQUENCE: 15
```
atgacaaacc tgcaagatca aacccaacag attgttccgt tcatacggag ccttctgatg 60
ccaacaaccg gaccggcgtc cattccggac gacaccctgg agaagcacac tctcaggtca 120
gagacctcga cctacaattt gactgtgggg gacacagggt cagggctaat tgtctttttc 180
cctggattcc ctggctcaat tgtgggtgct cactacacac tgcagagcaa tgggaactac 240
aagttcgatc agatgctcct gactgcccag aacctaccgg ccagctacaa ctactgcaga 300
ctagtgagtc ggagtctcac agtgaggtca agcacactcc ctggtggcgt ttatgcacta 360
aacggcacca taaacgccgt gaccttccaa ggaagcctga gtgaactgac agatgttagc 420
tacaatgggt tgatgtctgc aacagccaac atcaacgaca aaattgggaa tgtcctggta 480
ggggaagggg tcactgtcct cagcctaccc acatcatatg atcttgggta tgtgaggctt 540
ggtgacccca ttcccgctat agggcttgac ccaaaaatgg tagctacatg cgacagcagt 600
gacaggccca gagtctacac cataactgca gccgatgatt accaattctc atcacagtac 660
caaccaggtg ggtaacaat cacactgttc tcagccaaca ttgatgctat cacaagcctc 720
agcattgggg gagagctcgt gtttcaaaca agcgtccaag gccttgtact gggcgccacc 780
atctacctta taggctttga tgggactgcg gtaatcacca gagctgtagc cgcagataat 840
gggctgacgg ccggcaccga caatcttatg ccattcaatc ttgtcattcc aaccaatgag 900
ataacccagc caatcacatc catcaaactg gagatagtga cctccaaaag tggtggtcag 960
gcaggggatc agatgtcatg gtcggcaagt gggagcctag cagtgacgat ccatggtggc 1020
aactatccag ggccctccg tcccgtcaca ctagtagcct acgaaagagt ggcaacagga 1080
tccgtcgtta cggtcgctgg ggtgagtaac ttcgagctga ttccaaatcc tgaactagca 1140
aagaacctgg ttacagaata cggccgattt gacccaggag ccatgaacta cacaaaattg 1200
atactgagtg agagggaccg tcttggcatc aagaccgtct ggccaacaag ggagtacact 1260
gattttcgtg agtacttcat ggaggtggcc gacctcaact ctcccctgaa gattgcagga 1320
gcatttggct tcaaagacat aatccgggct ataaggaggt aacccccccc cctaacgtta 1380
ctggccgaag ccgcttggaa taaggccggt gtgcgtttgt ctatatgtta ttttccacca 1440
tattgccgtc ttttggcaat gtgagggccc ggaaacctgg ccctgtcttc ttgacgagca 1500
ttcctagggg tctttcccct ctcgccaaag gaatgcaagg tctgttgaat gtcgtgaagg 1560
aagcagttcc tctggaagct tcttgaagac aaacaacgtc tgtagcgacc ctttgcaggc 1620
agcggaaccc cccacctggc gacaggtgcc tctgcggcca aaagccacgt gtataagata 1680
cacctgcaaa ggcggcacaa ccccagtgcc acgttgtgag ttggatagtt gtggaaagag 1740
tcaaatggct ctcctcaagc gtattcaaca aggggctgaa ggatgcccag aaggtacccc 1800
attgtatggg atctgatctg gggcctcggt gcacatgctt tacatgtgtt tagtcgaggt 1860
taaaaaacgt ctaggccccc cgaaccacgg ggacgtggtt ttcctttgaa aaacacgatg 1920
ataataccat gcaccgtcct catctcagac ggcactcgcg ttactacgcg aaaggagagg 1980
tgcttaacaa acacatggat tgcggtggaa aacggtgctg ctcaggcgca gctgtattca 2040

-continued

```
ctcttttctg gacttgtgtc aggattatgc gggagcatat ctgctttgta cgcaacgcta   2100
tggaccgcca tttatttttg aggaatgctt tttggactat cgtactgctt tcttccttcg   2160
ctagccagag caccgccgcc gtcacgtacg actacatttt aggccgtcgc gcgctcgacg   2220
cgctaaccat accggcggtt ggcccgtata acagatacct cactagggta tcaagaggct   2280
gcgacgttgt cgagctcaac ccgatttcta acgtggacga catgatatcg gcggccaaag   2340
aaaaagagaa ggggggccct ttcgaggcct ccgtcgtctg gttctacgtg attaagggcg   2400
acgacggcga ggacaagtac tgtccaatct atagaaaaga gtacagggaa tgtggcgacg   2460
tacaactgct atctgaatgc gccgttcaat ctgcacagat gtgggcagtg gactatgttc   2520
ctagcaccct tgtatcgcga aatggcgcgg gactgactat attctccccc actgctgcgc   2580
tctctggcca atacttgctg accctgaaaa tcgggagatt tgcgcaaaca gctctcgtaa   2640
ctctagaagt taacgatcgc tgtttaaaga tcgggtcgca gcttaacttt ttaccgtcga   2700
aatgctggac aacagaacag tatcagactg gatttcaagg cgaacacctt tatccgatcg   2760
cagacaccaa tacacgacac gcggacgacg tatatcgggg atacgaagat attctgcagc   2820
gctggaataa tttgctgagg aaaaagaatc ctagcgcgcc agaccctcgt ccagatagcg   2880
tcccgcaaga aattcccgct gtaaccaaga aagcggaagg gcgcaccccg gacgcagaaa   2940
gcagcgaaaa gaaggcccct ccagaagact cggaggacga catgcaggca gaggcttctg   3000
gagaaaatcc tgccgccctc cccgaagacg acgaagtccc cgaggacacc gagcacgatg   3060
atccaaactc ggatcctgac tattacaatg acatgcccgc cgtgatcccg gtggaggaga   3120
ctactaaaag ttctaatgcc gtctccatgc ccatattcgc ggcgttcgta gcctgcgcgg   3180
tcgcgctcgt ggggctactg gtttggagca tcgtaaaatg cgcgcgtagc taagcggccg   3240
cggggatcca gacatgataa gatacattga tgagtttgga caaaccacaa ctagaatgca   3300
gtgaaaaaaa tgctttattt gtgaaatttg tgatgctatt gctttatttg taaccattat   3360
aagctgcaat aaacaagtta acaacaacaa ttgcattcat tttatgtttc aggttcaggg   3420
ggaggtgtgg gaggtttttt                                               3440
```

```
<210> SEQ ID NO 16
<211> LENGTH: 1302
<212> TYPE: DNA
<213> ORGANISM: artificial sequence
<220> FEATURE:
<223> OTHER INFORMATION: Polynucleotide encoding ILTV gD

<400> SEQUENCE: 16
atgcaccgtc ctcatctcag acggcactcg cgttactacg cgaaaggaga ggtgcttaac     60
aaacacatgg attgcggtgg aaaacggtgc tgctcaggcg cagctgtatt cactcttttc    120
tggacttgtg tcaggattat gcgggagcat atctgctttg tacgcaacgc tatggaccgc    180
catttatttt tgaggaatgc tttttggact atcgtactgc tttcttcctt cgctagccag    240
agcaccgccg ccgtcacgta cgactacatt ttaggccgtc gcgcgctcga cgcgctaacc    300
ataccggcgg ttggcccgta taacagatac ctcactaggg tatcaagagg ctgcgacgtt    360
gtcgagctca acccgatttc taacgtggac gacatgatat cggcggccaa agaaaaagag    420
aaggggggcc ctttcgaggc ctccgtcgtc tggttctacg tgattaaggg cgacgacggc    480
gaggacaagt actgtccaat ctatagaaaa gagtacaggg aatgtggcga cgtacaactg    540
ctatctgaat gcgccgttca atctgcacag atgtgggcag tggactatgt tcctagcacc    600
cttgtatcgc gaaatggcgc gggactgact atattctccc ccactgctgc gctctctggc    660
```

```
caatacttgc tgaccctgaa aatcgggaga tttgcgcaaa cagctctcgt aactctagaa    720
gttaacgatc gctgtttaaa gatcgggtcg cagcttaact ttttaccgtc gaaatgctgg    780
acaacagaac agtatcagac tggatttcaa ggcgaacacc tttatccgat cgcagacacc    840
aatacacgac acgcggacga cgtatatcgg ggatacgaag atattctgca gcgctggaat    900
aatttgctga ggaaaaagaa tcctagcgcg ccagaccctc gtccagatag cgtcccgcaa    960
gaaattcccg ctgtaaccaa gaaagcggaa gggcgcaccc cggacgcaga aagcagcgaa   1020
aagaaggccc ctccagaaga ctcggaggac gacatgcagg cagaggcttc tggagaaaat   1080
cctgccgccc tccccgaaga cgacgaagtc cccgaggaca ccgagcacga tgatccaaac   1140
tcggatcctg actattacaa tgacatgccc gccgtgatcc cggtggagga gactactaaa   1200
agttctaatg ccgtctccat gcccatattc gcggcgttcg tagcctgcgc ggtcgcgctc   1260
gtggggctac tggtttggag catcgtaaaa tgcgcgcgta gc                      1302
```

<210> SEQ ID NO 17
<211> LENGTH: 434
<212> TYPE: PRT
<213> ORGANISM: artificial sequence
<220> FEATURE:
<223> OTHER INFORMATION: ILTV gD protein

<400> SEQUENCE: 17

```
Met His Arg Pro His Leu Arg Arg His Ser Arg Tyr Tyr Ala Lys Gly
1               5                   10                  15

Glu Val Leu Asn Lys His Met Asp Cys Gly Gly Lys Arg Cys Cys Ser
            20                  25                  30

Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
    50                  55                  60

Arg Asn Ala Phe Trp Thr Ile Val Leu Leu Ser Ser Phe Ala Ser Gln
65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
```

```
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser
```

<210> SEQ ID NO 18
<211> LENGTH: 3804
<212> TYPE: DNA
<213> ORGANISM: artificial sequence
<220> FEATURE:
<223> OTHER INFORMATION: pFwtSV40VP2 for vHFT313
<220> FEATURE:
<221> NAME/KEY: VP2
<222> LOCATION: (1)..(1362)
<220> FEATURE:
<221> NAME/KEY: SV40 Poly A
<222> LOCATION: (1383)..(1594)
<220> FEATURE:
<221> NAME/KEY: SV40 Promoter
<222> LOCATION: (1624)..(1968)
<220> FEATURE:
<221> NAME/KEY: NDV-Fwt VIId
<222> LOCATION: (1981)..(3642)
<220> FEATURE:
<221> NAME/KEY: Synthetic Poly A
<222> LOCATION: (3651)..(3804)

<400> SEQUENCE: 18

```
atgacaaacc tgcaagatca aacccaacag attgttccgt tcatacggag ccttctgatg     60
ccaacaaccg gaccggcgtc cattccggac gacaccctgg agaagcacac tctcaggtca    120
gagacctcga cctacaattt gactgtgggg gacacagggt cagggctaat tgtctttttc    180
cctggattcc ctggctcaat tgtgggtgct cactacacac tgcagagcaa tgggaactac    240
aagttcgatc agatgctcct gactgcccag aacctaccgg ccagctacaa ctactgcaga    300
ctagtgagtc ggagtctcac agtgaggtca agcacactcc ctggtggcgt ttatgcacta    360
aacggcacca taaacgccgt gaccttccaa ggaagcctga gtgaactgac agatgttagc    420
tacaatgggt tgatgtctgc aacagccaac atcaacgaca aaattgggaa tgtcctggta    480
ggggaagggg tcactgtcct cagcctaccc acatcatatg atcttgggta tgtgaggctt    540
```

```
ggtgacccca ttcccgctat agggcttgac ccaaaaatgg tagctacatg cgacagcagt    600
gacaggccca gagtctacac cataactgca gccgatgatt accaattctc atcacagtac    660
caaccaggtg gggtaacaat cacactgttc tcagccaaca ttgatgctat cacaagcctc    720
agcattgggg gagagctcgt gtttcaaaca agcgtccaag gccttgtact gggcgccacc    780
atctacctta taggctttga tgggactgcg gtaatcacca gagctgtagc cgcagataat    840
gggctgacgg ccggcaccga caatcttatg ccattcaatc ttgtcattcc aaccaatgag    900
ataacccagc caatcacatc catcaaactg gagatagtga cctccaaaag tggtggtcag    960
gcaggggatc agatgtcatg gtcggcaagt gggagcctag cagtgacgat ccatggtggc   1020
aactatccag gggccctccg tcccgtcaca ctagtagcct acgaaagagt ggcaacagga   1080
tccgtcgtta cggtcgctgg ggtgagtaac ttcgagctga ttccaaatcc tgaactagca   1140
aagaacctgg ttacagaata cggccgattt gacccaggag ccatgaacta cacaaaattg   1200
atactgagtg agagggaccg tcttggcatc aagaccgtct ggccaacaag ggagtacact   1260
gattttcgtg agtacttcat ggaggtggcc gacctcaact ctcccctgaa gattgcagga   1320
gcatttggct tcaaagacat aatccgggct ataaggagg aagcttgatc tagagcggcc   1380
gcggggatcc agacatgata agatacattg atgagtttgg acaaaccaca actagaatgc   1440
agtgaaaaaa atgctttatt tgtgaaattt gtgatgctat tgcttttattt gtaaccatta   1500 taagctgcaa taaacaagtt aacaacaaca attgcattca ttttatgttt caggttcagg   1560
gggaggtgtg ggaggttttt tcggatcctc tagagtcgac gaattcgagc tcggtacagc   1620
ttggctgtgg aatgtgtgtc agttagggtg tggaaagtcc ccaggctccc cagcaggcag   1680
aagtatgcaa agcatgcatc tcaattagtc agcaaccagg tgtggaaagt ccccaggctc   1740
cccagcaggc agaagtatgc aaagcatgca tctcaattag tcagcaacca tagtcccgcc   1800
cctaactccg cccatcccgc ccctaactcc gcccagttcc gcccattctc cgccccatgg   1860
ctgactaatt ttttttattt atgcagaggc cgaggccgcc tcggcctctg agctattcca   1920
gaagtagtga ggaggctttt ttggaggcct aggcttttgc aaaaagctgc ggccgccacc   1980
atgggctcca aaccttctac caggatccca gcacctctga tgctgatcac ccggattatg   2040
ctgatattgg gctgtatccg tccgacaagc tctcttgacg gcaggcctct tgcagctgca   2100
ggaattgtag taacaggaga taaggcagtc aatgtataca cttcgtctca gacagggtca   2160
atcatagtca agttgctccc gaatatgccc agggataagg aggcgtgtgc aaaagcccca   2220
ttagaggcat ataacagaac actgactact ttgctcactc ctcttggcga ctccatccgc   2280
aagatccaag ggtctgtgtc cacatctgga ggaggcaagc aaggccgcct gataggtgct   2340
gttattggca gtgtagctct tggggttgca acagcggcac agataacagc agctgcggcc   2400
ctaatacaag ccaaccagaa tgccgccaac atcctccggc ttaaggagag cattgctgca   2460
accaatgaag ctgtgcatga agtcaccgac ggattatcac aactatcagt ggcagttggg   2520
aagatgcagc agtttgtcaa tgaccagttt aataatacgg cgcgagaatt ggactgtata   2580
aaaatcacac aacaggttgg tgtagaactc aacctatacc taactgaatt gactacagta   2640
ttcgggccac agatcacctc ccctgcatta actcagctga ccatccaggc actttataat   2700
ttagctggtg gcaatatgga ttacttatta actaagttag gtataggaa caatcaactc   2760 agctcgttaa ttggtagcgg cctgatcact ggttaccctata actctatga ctcacagact   2820 caactcttgg gcatacaagt gaatttaccc tcagtcggga acttaaataa tatgcgtgcc   2880
```
acctatttgg agaccttatc tgtaagtaca accaaaggat atgcctcagc acttgtcccg 2940
aaagtagtga cacaagtcgg ttccgtgata gaagagcttg acacctcata ctgtatagag 3000
tccgatctgg atttatattg tactagaata gtgacattcc ccatgtcccc aggtatttat 3060
tcctgtttga gcggcaacac atcagcttgc atgtattcaa agactgaagg cgcactcact 3120
acgccgtata tggcccttaa aggctcagtt attgccaatt gtaaaataac aacatgtaga 3180
tgtacagacc ctcctggtat catatcgcaa aattatggag aagctgtatc cctgatagat 3240
agacattcgt gcaatgtctt atcattagac gggataactc taaggctcag tggggaattt 3300
gatgcaactt atcaaaagaa catctcaata ctagattctc aagtcatcgt gacaggcaat 3360
cttgatatat caactgaact tggaaacgtc aacaattcaa tcagcaatgc cttggatagg 3420
ttggcagaaa gcaacagcaa gctagaaaaa gtcaatgtca gactaaccag cacatctgct 3480
ctcattacct atattgttct aactgtcatt tctctagttt tcggtgcact tagtctggtg 3540
ttagcgtgtt acctgatgta caaacagaag gcacaacaaa agaccttgct atggcttggg 3600
aataataccc tcgatcagat gagagccact acaagagcat gagcggccgc aataaaatat 3660
ctttattttc attacatctg tgtgttggtt ttttgtgtga atcgatagta ctaacatacg 3720
ctctccatca aaacaaaacg aaacaaaaca aactagcaaa ataggctgtc cccagtgcaa 3780
gtgcaggtgc cagaacattt ctct 3804

<210> SEQ ID NO 19
<211> LENGTH: 3797
<212> TYPE: DNA
<213> ORGANISM: artificial sequence
<220> FEATURE:
<223> OTHER INFORMATION: pVP2IRESFwt for vHVT316
<220> FEATURE:
<221> NAME/KEY: VP2
<222> LOCATION: (1)..(1362)
<220> FEATURE:
<221> NAME/KEY: IRES
<222> LOCATION: (1363)..(1925)
<220> FEATURE:
<221> NAME/KEY: NDV-Fwt VIId
<222> LOCATION: (1929)..(3590)
<220> FEATURE:
<221> NAME/KEY: SV40 Poly A
<222> LOCATION: (3599)..(3797)

<400> SEQUENCE: 19
atgacaaacc tgcaagatca aacccaacag attgttccgt tcatacggag ccttctgatg 60
ccaacaaccg gaccggcgtc cattccggac gacaccctgg agaagcacac tctcaggtca 120
gagacctcga cctacaattt gactgtgggg gacacagggt cagggctaat tgtctttttc 180
cctggattcc ctggctcaat tgtgggtgct cactacacac tgcagagcaa tgggaactac 240
aagttcgatc agatgctcct gactgcccag aacctaccgg ccagctacaa ctactgcaga 300
ctagtgagtc ggagtctcac agtgaggtca agcacactcc ctggtggcgt ttatgcacta 360
aacggcacca taaacgccgt gaccttccaa ggaagcctga gtgaactgac agatgttagc 420
tacaatgggt tgatgtctgc aacagccaac atcaacgaca aaattgggaa tgtcctggta 480
ggggaagggg tcactgtcct cagcctaccc acatcatatg atcttgggta tgtgaggctt 540
ggtgacccca ttcccgctat agggcttgac ccaaaaatgg tagctacatg cgacagcagt 600
gacaggccca gagtctacac cataactgca gccgatgatt accaattctc atcacagtac 660
caaccaggtg gggtaacaat cacactgttc tcagccaaca ttgatgctat cacaagcctc 720
agcattgggg gagagctcgt gtttcaaaca agcgtccaag gccttgtact gggcgccacc 780

```
atctacctta taggctttga tgggactgcg gtaatcacca gagctgtagc cgcagataat    840
gggctgacgg ccggcaccga caatcttatg ccattcaatc ttgtcattcc aaccaatgag    900
ataacccagc caatcacatc catcaaactg gagatagtga cctccaaaag tggtggtcag    960
gcagggatc agatgtcatg gtcggcaagt gggagcctag cagtgacgat ccatggtggc    1020
aactatccag gggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggagg aacccccccc cctaacgtta    1380
ctggccgaag ccgcttggaa taaggccggt gtgcgtttgt ctatatgtta ttttccacca    1440
tattgccgtc ttttggcaat gtgagggccc ggaaacctgg ccctgtcttc ttgacgagca    1500
ttcctagggg tcttcccct ctcgccaaag gaatgcaagg tctgttgaat gtcgtgaagg    1560
aagcagttcc tctggaagct tcttgaagac aaacaacgtc tgtagcgacc ctttgcaggc    1620
agcggaaccc cccacctggc gacaggtgcc tctgcggcca aaagccacgt gtataagata    1680
cacctgcaaa gcggcacaa ccccagtgcc acgttgtgag ttggatagtt gtggaaagag    1740
tcaaatggct ctcctcaagc gtattcaaca aggggctgaa ggatgcccag aaggtacccc    1800
attgtatggg atctgatctg gggcctcggt gcacatgctt tacatgtgtt tagtcgaggt    1860
taaaaaacgt ctaggccccc cgaaccacgg ggacgtggtt ttcctttgaa aaacacgatg    1920
ataataccat gggctccaaa ccttctacca ggatcccagc acctctgatg ctgatcaccc    1980
ggattatgct gatattgggc tgtatccgtc cgacaagctc tcttgacggc aggcctcttg    2040
cagctgcagg aattgtagta acaggagata aggcagtcaa tgtatacact tcgtctcaga    2100
cagggtcaat catagtcaag ttgctcccga atatgcccag ggataaggag gcgtgtgcaa    2160
aagcccatt agaggcatat aacagaacac tgactacttt gctcactcct cttggcgact    2220
ccatccgcaa gatccaaggg tctgtgtcca catctggagg aggcaagcaa ggccgcctga    2280
taggtgctgt tattggcagt gtagctcttg gggttgcaac agcggcacag ataacagcag    2340
ctgcggccct aatacaagcc aaccagaatg ccgccaacat cctccggctt aaggagagca    2400
ttgctgcaac caatgaagct gtgcatgaag tcaccgacgg attatcacaa ctatcagtgg    2460
cagttgggaa gatgcagcag tttgtcaatg accagtttaa taatacggcg cgagaattgg    2520
actgtataaa aatcacacaa caggttggtg tagaactcaa cctataccta actgaattga    2580
ctacagtatt cggccacag atcacctccc ctgcattaac tcagctgacc atccaggcac    2640
tttataattt agctggtggc aatatggatt acttattaac taagttaggt atagggaaca    2700
atcaactcag ctcgttaatt ggtagcgcc tgatcactgg ttaccctata ctgtatgact    2760
cacagactca actcttgggc atacaagtga atttaccctc agtcgggaac ttaaataata    2820
tgcgtgccac ctatttggag accttatctg taagtacaac caaaggatat gcctcagcac    2880
ttgtcccgaa agtagtgaca caagtcggtt ccgtgataga agagcttgac acctcatact    2940
gtatagagtc cgatctggat ttatattgta ctagaatagt gacattcccc atgtccccag    3000
gtatttattc ctgtttgagc ggcaacacat cagcttgcat gtattcaaag actgaaggcg    3060
cactcactac gccgtatatg gcccttaaag gctcagttat tgccaattgt aaaataacaa    3120
```

| catgtagatg tacagaccct cctggtatca tatcgcaaaa ttatggagaa gctgtatccc | 3180 |
| tgatagatag acattcgtgc aatgtcttat cattagacgg gataactcta aggctcagtg | 3240 |
| gggaatttga tgcaacttat caaaagaaca tctcaatact agattctcaa gtcatcgtga | 3300 |
| caggcaatct tgatatatca actgaacttg gaaacgtcaa caattcaatc agcaatgcct | 3360 |
| tggataggtt ggcagaaagc aacagcaagc tagaaaaagt caatgtcaga ctaaccagca | 3420 |
| catctgctct cattacctat attgttctaa ctgtcatttc tctagttttc ggtgcactta | 3480 |
| gtctggtgtt agcgtgttac ctgatgtaca acagaaggc acaacaaaag accttgctat | 3540 |
| ggcttgggaa taatacccctc gatcagatga gagccactac aagagcatga ggcgcgccgg | 3600 |
| ggatccagac atgataagat acattgatga gtttggacaa accacaacta gaatgcagtg | 3660 |
| aaaaaaatgc tttatttgtg aaatttgtga tgctattgct ttatttgtaa ccattataag | 3720 |
| ctgcaataaa caagttaaca acaacaattg cattcatttt atgtttcagg ttcaggggga | 3780 |
| ggtgtgggag gtttttt | 3797 |

<210> SEQ ID NO 20
<211> LENGTH: 1834
<212> TYPE: DNA
<213> ORGANISM: artificial sequence
<220> FEATURE:
<223> OTHER INFORMATION: HVT US2SVgDwtsyn for vHVT407
<220> FEATURE:
<221> NAME/KEY: SV40 Promoter
<222> LOCATION: (1)..(345)
<220> FEATURE:
<221> NAME/KEY: ILTV gDwt
<222> LOCATION: (362)..(1666)
<220> FEATURE:
<221> NAME/KEY: synthetic poly A
<222> LOCATION: (1681)..(1834)

<400> SEQUENCE: 20

| gctgtggaat gtgtgtcagt tagggtgtgg aaagtcccca ggctccccag caggcagaag | 60 |
| tatgcaaagc atgcatctca attagtcagc aaccaggtgt ggaaagtccc caggctcccc | 120 |
| agcaggcaga agtatgcaaa gcatgcatct caattagtca gcaaccatag tcccgcccct | 180 |
| aactccgccc atcccgcccc taactccgcc cagttccgcc cattctccgc cccatggctg | 240 |
| actaattttt tttatttatg cagaggccga ggccgcctcg gcctctgagc tattccagaa | 300 |
| gtagtgagga ggcttttttg gaggcctagg cttttgcaaa aagctgcggc cggccgccac | 360 |
| catgcaccgt cctcatctca gacggcactc gcgttactac gcgaaggag aggtgcttaa | 420 |
| caaacacatg gattgcggtg gaaaacggtg ctgctcaggc gcagctgtat tcactctttt | 480 |
| ctggacttgt gtcaggatta tgcgggagca tatctgcttt gtacgcaacg ctatggaccg | 540 |
| ccatttattt ttgaggaatg ctttttggac tatcgtactg cttttcttcct tcgctagcca | 600 |
| gagcaccgcc gccgtcacgt acgactacat tttaggccgt cgcgcgctcg acgcgctaac | 660 |
| cataccggcg gttggcccgt ataacagata cctcactagg gtatcaagag gctgcgacgt | 720 |
| tgtcgagctc aacccgattt ctaacgtgga cgacatgata tcggcggcca agaaaaaga | 780 |
| gaaggggggc cctttcgagg cctccgtcgt ctggttctac gtgattaagg gcgacgacgg | 840 |
| cgaggacaag tactgtccaa tctatagaaa agagtacagg gaatgtggcg acgtacaact | 900 |
| gctatctgaa tgcgccgttc aatctgcaca gatgtgggca gtggactatg ttcctagcac | 960 |
| ccttgtatcg cgaaatggcg cgggactgac tatattctcc cccactgctg cgctctctgg | 1020 |
| ccaatacttg ctgaccctga aaatcgggag atttgcgcaa acagctctcg taactctaga | 1080 |

```
agttaacgat cgctgtttaa agatcgggtc gcagcttaac tttttaccgt cgaaatgctg    1140
gacaacagaa cagtatcaga ctggatttca aggcgaacac ctttatccga tcgcagacac    1200
caatacacga cacgcggacg acgtatatcg gggatacgaa gatattctgc agcgctggaa    1260
taatttgctg aggaaaaaga atcctagcgc gccagaccct cgtccagata gcgtcccgca    1320
agaaattccc gctgtaacca agaaagcgga agggcgcacc ccggacgcag aaagcagcga    1380
aaagaaggcc cctccagaag actcggagga cgacatgcag gcagaggctt ctggagaaaa    1440
tcctgccgcc ctccccgaag acgacgaagt ccccgaggac accgagcacg atgatccaaa    1500
ctcggatcct gactattaca atgacatgcc cgccgtgatc ccggtggagg agactactaa    1560
aagttctaat gccgtctcca tgcccatatt cgcggcgttc gtagcctgcg cggtcgcgct    1620
cgtggggcta ctggtttgga gcatcgtaaa atgcgcgcgt agctaatcga gcctagaggc    1680
aataaaatat ctttattttc attacatctg tgtgttggtt ttttgtgtga atcgatagta    1740
ctaacatacg ctctccatca aaacaaaacg aaacaaaaca aactagcaaa ataggctgtc    1800
cccagtgcaa gtgcaggtgc cagaacattt ctct                               1834
```

<210> SEQ ID NO 21
<211> LENGTH: 1659
<212> TYPE: DNA
<213> ORGANISM: artificial sequence
<220> FEATURE:
<223> OTHER INFORMATION: Polynucleotide encoding NDV-F of genotype V, codon-optimized in pHVTIG1gDCaFopt (vHVT308)

<400> SEQUENCE: 21

```
atgggcagca agcccagcac ctggatcagc gtgaccctga tgctgatcac cagaaccatg    60
ctgatcctga gctgcatctg ccccacaagc agcctggacg gcagacccct ggccgctgcc    120
ggcatcgtgg tgaccggcga caaggccgtg aacatctaca ccagcagcca gaccggcagc    180
atcatcatca gctgctgcc caacatgccc aaggacaaag aggcctgcgc caaggccccc    240
ctggaagcct acaacagaac cctgaccacc ctgctgaccc cctgggcga cagcatcaga    300 agaatccagg gcagcgccac cacaagcggc ggaggaaagc agggcagact ggtgggcgct    360
atcatcggga gcgtggccct gggcgtggcc acagctgccc agattaccgc tgcagccgcc    420
ctgattcagg ccaatcagaa cgccgccaac atcctgagac tgaaagagag cattgccgcc    480
accaacgacg ccgtgcacga agtgacaaac ggactgtccc agctggctgt cgctgtcggc    540
aagatgcagc agttcgtgaa caaccagttc aacaacaccg ccagagagct ggactgcatc    600
aagatcgccc agcaggtggg cgtggagctg aacctgtacc tgaccgagct gaccacagtg    660
ttcggccccc agatcacaag ccccgctctg acccagctga caatccaggc cctgtacaac    720
ctggctggcg gcaacatgga ctatctgctg actaagctgg gagtgggcaa caaccagctg    780
tccagcctga tcgggtccgg gctgatcaca ggcaaccca tcctgtacga cagccagaca    840
cagctgctgg gcatccagat caacctgcca tccgtgggaa gctgaacaa catgagagcc    900 acctacctgg aaaccctgag cgtgtccacc accaagggct cgccagcgc cctggtgccc    960 aaggtggtga cacaggtggg cagcgtgatc gaggaactgg acaccagcta ctgcatcgag    1020
agcgacatcg acctgtactg caccagagtg gtgaccttcc caatgagccc cggcatctac    1080
agctgcctga gcggcaacac cagcgcctgc atgtacagca agaccgaagg agcactgaca    1140
acaccctaca tggccctgaa gggaagcgtg atcgccaact gcaagatgac cacctgcaga    1200
tgcgccgacc cccaggcat catcagccag aactacggcg aggccgtgag cctgatcgac    1260
```

```
aaacattcct gtagcgtgct gtccctggat ggcatcacac tgagactgag cggcgagttc    1320
gacgccacct accagaagaa catcagcatc ctggacagcc aggtgatcgt gaccggcaac    1380
ctggacatca gcaccgagct gggcaacgtg aacaacagca tcagcagcac cctggacaag    1440
ctggccgagt ccaacaacaa gctgaacaaa gtgaacgtga acctgaccag cacaagcgcc    1500
ctgatcacct acatcgtgct ggccatcgtg tccctggcct tcggcgtgat cagcctggtg    1560
ctggcctgct acctgatgta caagcagaga gcccagcaga aaaccctgct gtggctgggc    1620
aataacaccc tggaccagat gagggccacc accagaacc                           1659
```

<210> SEQ ID NO 22
<211> LENGTH: 553
<212> TYPE: PRT
<213> ORGANISM: artificial sequence
<220> FEATURE:
<223> OTHER INFORMATION: NDV-F of genotype V (vHVT308)

<400> SEQUENCE: 22

```
Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Gly
            100                 105                 110

Lys Gln Gly Arg Leu Val Gly Ala Ile Ile Gly Ser Val Ala Leu Gly
        115                 120                 125

Val Ala Thr Ala Ala Gln Ile Thr Ala Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Asp Ala Val His Glu Val Thr Asn Gly Leu Ser Gln Leu Ala
                165                 170                 175

Val Ala Val Gly Lys Met Gln Gln Phe Val Asn Asn Gln Phe Asn Asn
            180                 185                 190

Thr Ala Arg Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Ile Asn
        275                 280                 285

Leu Pro Ser Val Gly Ser Leu Asn Asn Met Arg Ala Thr Tyr Leu Glu
```

```
                290                 295                 300
Thr Leu Ser Val Ser Thr Thr Lys Gly Phe Ala Ser Ala Leu Val Pro
305                 310                 315                 320

Lys Val Val Thr Gln Val Gly Ser Val Ile Glu Leu Asp Thr Ser
            325                 330                 335

Tyr Cys Ile Glu Ser Asp Ile Asp Leu Tyr Cys Thr Arg Val Val Thr
                340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
                420                 425                 430

Thr Leu Arg Leu Ser Gly Glu Phe Asp Ala Thr Tyr Gln Lys Asn Ile
            435                 440                 445

Ser Ile Leu Asp Ser Gln Val Ile Val Thr Gly Asn Leu Asp Ile Ser
450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
            485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
            515                 520                 525

Gln Arg Ala Gln Gln Lys Thr Leu Leu Trp Leu Gly Asn Asn Thr Leu
            530                 535                 540

Asp Gln Met Arg Ala Thr Thr Arg Thr
545                 550
```

<210> SEQ ID NO 23
<211> LENGTH: 476
<212> TYPE: DNA
<213> ORGANISM: artificial sequence
<220> FEATURE:
<223> OTHER INFORMATION: HHV3gB promoter (reverse direction)

<400> SEQUENCE: 23
cccgggttat atcttctgat tgtgtgggct ctacttgtaa actctcaaaa aacgagcttg      60
gagagaccga cacaaccgcc gtaacaaaca agaaaatat gcataaaaag cataaccaca     120
cccccgtaac ggatgttatg aaaacgccgg gtccgttgaa tccggagcca gccgctgcat    180
tagggtgtat agaagagaaa aaacgtctga atcgtagatt acgacggtat tctggtcgat    240
ccctgttct ccactttgaa taatagccac aaggggacat gtttcttcgt acgttaaata    300
aatgccgtct aagggtccgt gggaactgcc tataccttta ggttgagacg tgcacccgcg    360
tggatcctta cctagacggt caacgcgaca taaccgcacc tccccacaat ggaaaacaga    420
ggtgaatagt gtggttgcaa acacaagctc cctaatatat ttccaggcaa gtctct        476

<210> SEQ ID NO 24
<211> LENGTH: 476

```
<212> TYPE: DNA
<213> ORGANISM: artificial sequence
<220> FEATURE:
<223> OTHER INFORMATION: HHV3gB promoter
<400> SEQUENCE: 24
agagacttgc ctggaaatat attagggagc ttgtgtttgc aaccacacta ttcacctctg 60
ttttccattg tggggaggtg cggttatgtc gcgttgaccg tctaggtaag gatccacgcg 120
ggtgcacgtc tcaacctaaa ggtataggca gttcccacgg acccttagac ggcatttatt 180
```

```
taacgtacga agaaacatgt ccccttgtgg ctattattca aagtggagaa acagggatcg 240
accagaatac cgtcgtaatc tacgattcag acgtttttc tcttctatac accctaatgc 300
agcggctggc tccggattca acggacccgg cgttttcata acatccgtta cgggggtgtg 360
gttatgcttt ttatgcatat tttctttgtt tgttacggcg gttgtgtcgg tctctccaag 420
ctcgtttttt gagagtttac aagtagagcc cacacaatca gaagatataa cccggg 476

<210> SEQ ID NO 25
<211> LENGTH: 4347
<212> TYPE: DNA
<213> ORGANISM: artificial sequence
<220> FEATURE:
<223> OTHER INFORMATION: Plasmid pHVTIG1gDCaFopt for vHVT308
<220> FEATURE:
<221> NAME/KEY: SV40 Poly A in reverse direction
<222> LOCATION: (1)..(199)
<220> FEATURE:
<221> NAME/KEY: ILTgD  in reverse direction
<222> LOCATION: (318)..(1622)
<220> FEATURE:
<221> NAME/KEY: HHV3gB promoter  in reverse direction
<222> LOCATION: (1635)..(2110)
<220> FEATURE:
<221> NAME/KEY: SV40 promoter
<222> LOCATION: (2129)..(2496)
<220> FEATURE:
<221> NAME/KEY: NDV-F-CA02
<222> LOCATION: (2515)..(4179)
<220> FEATURE:
<221> NAME/KEY: Syn Poly A
<222> LOCATION: (4194)..(4347)

<400> SEQUENCE: 25
aaaaaacctc ccacacctcc ccctgaacct gaaacataaa atgaatgcaa ttgttgttgt 60
taacttgttt attgcagctt ataatggtta caaataaagc aatagcatca caaatttcac 120
aaataaagca tttttttcac tgcattctag ttgtggtttg tccaaactca tcaatgtatc 180
ttatcatgtc tggatccccg cggcctatgc gcttttcgaa cgtcccaatg aataggcatt 240
ggtatgctat tccatgtgat ttatattatg agcgtgaggc gtggcatgta ggaagaaacc 300
acctattcta ggctcgatta gctacgcgcg cattttacga tgctccaaac cagtagcccc 360
acgagcgcga ccgcgcaggc tacgaacgcc gcgaatatgg gcatggagac ggcattagaa 420
cttttagtag tctcctccac cgggatcacg gcgggcatgt cattgtaata gtcaggatcc 480
gagtttggat catcgtgctc ggtgtcctcg gggacttcgt cgtcttcggg gagggcggca 540
ggattttctc cagaagcctc tgcctgcatg tcgtcctccg agtcttctgg aggggccttc 600
ttttcgctgc tttctgcgtc cggggtgcgc ccttccgctt tcttggttac agcgggaatt 660
tcttgcggga cgctatctgg acgagggtct ggcgcgctag gattcttttt cctcagcaaa 720
ttattccagc gctgcagaat atcttcgtat ccccgatata cgtcgtccgc gtgtcgtgta 780
ttggtgtctg cgatcggata aaggtgttcg ccttgaaatc cagtctgata ctgttctgtt 840

```
gtccagcatt tcgacggtaa aaagttaagc tgcgacccga tctttaaaca gcgatcgtta    900
acttctagag ttacgagagc tgtttgcgca aatctcccga ttttcagggt cagcaagtat    960
tggccagaga gcgcagcagt gggggagaat atagtcagtc ccgcgccatt tcgcgataca   1020
agggtgctag aacatagtc cactgcccac atctgtgcag attgaacggc gcattcagat   1080
agcagttgta cgtcgccaca ttccctgtac tcttttctat agattggaca gtacttgtcc   1140
tcgccgtcgt cgcccttaat cacgtagaac cagacgacgg aggcctcgaa agggcccccc   1200
ttctcttttt ctttggccgc cgatatcatg tcgtccacgt tagaaatcgg gttgagctcg   1260
acaacgtcgc agcctcttga taccctagtg aggtatctgt tatacgggcc aaccgccggt   1320
atggttagcg cgtcgagcgc gcgacggcct aaaatgtagt cgtacgtgac ggcggcggtg   1380
ctctggctag cgaaggaaga aagcagtacg atagtccaaa aagcattcct caaaaataaa   1440
tggcggtcca tagcgttgcg tacaaagcag atatgctccc gcataatcct gacacaagtc   1500
cagaaaagag tgaatacagc tgcgcctgag cagcaccgtt ttccaccgca atccatgtgt   1560
ttgttaagca cctctccttt cgcgtagtaa cgcgagtgcc gtctgagatg aggacggtgc   1620
atggtggcgg ccgcccccggg ttatatcttc tgattgtgtg ggctctactt gtaaactctc   1680
aaaaaacgag cttggagaga ccgacacaac cgccgtaaca aacaaagaaa atatgcataa   1740
aaagcataac cacaccccccg taacggatgt tatgaaaacg ccgggtccgt tgaatccgga   1800
gccagccgct gcattagggt gtatagaaga gaaaaaacgt ctgaatcgta gattacgacg   1860
gtattctggt cgatccctgt ttctccactt tgaataatag ccacaagggg acatgtttct   1920
tcgtacgtta aataaatgcc gtctaagggt ccgtgggaac tgcctatacc tttaggttga   1980
gacgtgcacc cgcgtggatc cttacctaga cggtcaacgc gacataaccg cacctcccca   2040
caatggaaaa cagaggtgaa tagtgtggtt gcaaacacaa gctccctaat atatttccag   2100
gcaagtctct gaattaattc cctcgaccca attcgagctc ggtacagctt ggctgtggaa   2160
tgtgtgtcag ttagggtgtg gaaagtcccc aggctcccca gcaggcagaa gtatgcaaag   2220
catgcatctc aattagtcag caaccaggtg tggaaagtcc ccaggctccc cagcaggcag   2280
aagtatgcaa agcatgcatc tcaattagtc agcaaccata gtcccgcccc taactccgcc   2340
catcccgccc ctaactccgc ccagttccgc ccattctccg cccatggctg actaatttt   2400 ttttattttat gcagaggccg aggccgcctc ggcctctgag ctattccaga agtagtgagg   2460 aggcttttttt ggaggcctag gcttttgcaa aaagctcccg ggcggccgc caccatgggc   2520 agcaagccca gcacctggat cagcgtgacc ctgatgctga tcaccagaac catgctgatc   2580
ctgagctgca tctgccccac aagcagcctg gacggcagac ccctggccgc tgccggcatc   2640
gtggtgaccg cgacaaggc cgtgaacatc tacaccagca gccagaccgg cagcatcatc   2700
atcaagctgc tgccccaacat gcccaaggac aaagaggcct gcgccaaggc cccctggaa   2760 gcctacaaca gaaccctgac caccctgctg accccctgg gcgacagcat cagaagaatc   2820
cagggcagcg ccaccacaag cggcggagga agcagggca gactggtggg cgctatcatc   2880
gggagcgtgg ccctgggcgt ggccacagct gcccagatta ccgctgcagc cgccctgatt   2940
caggccaatc agaacgccgc caacatcctg agactgaaag agagcattgc cgccaccaac   3000
gacgccgtgc acgaagtgac aaacggactg tcccagctgg ctgtcgctgt cggcaagatg   3060
cagcagttcg tgaacaacca gttcaacaac accgccagag agctggactg catcaagatc   3120
gcccagcagg tgggcgtgga gctgaacctg tacctgaccg agctgaccac agtgttcggc   3180
ccccagatca caagcccccg tctgacccag ctgacaatcc aggccctgta caacctggct   3240
```

-continued

```
ggcggcaaca tggactatct gctgactaag ctgggagtgg gcaacaacca gctgtccagc    3300
ctgatcgggt ccgggctgat cacaggcaac cccatcctgt acgacagcca gacacagctg    3360
ctgggcatcc agatcaacct gccatccgtg gaagcctga acaacatgag agccacctac    3420
ctggaaaccc tgagcgtgtc caccaccaag ggcttcgcca cgccctggt gcccaaggtg    3480 gtgacacagg tgggcagcgt gatcgaggaa ctggacacca gctactgcat cgagagcgac    3540
atcgacctgt actgcaccag agtggtgacc ttcccaatga gccccggcat ctacagctgc    3600
ctgagcggca acaccagcgc ctgcatgtac agcaagaccg aaggagcact gacaacaccc    3660
tacatggccc tgaagggaag cgtgatcgcc aactgcaaga tgaccacctg cagatgcgcc    3720 gacccccag gcatcatcag ccagaactac ggcgaggccg tgagcctgat cgacaaacat    3780
tcctgtagcg tgctgtccct ggatggcatc acactgagac tgagcggcga gttcgacgcc    3840
acctaccaga gaacatcag catcctggac agccaggtga tcgtgaccgg caacctggac    3900
atcagcaccg agctgggcaa cgtgaacaac agcatcagca gcaccctgga caagctggcc    3960
gagtccaaca acaagctgaa caaagtgaac gtgaacctga ccagcacaag cgccctgatc    4020
acctacatcg tgctggccat cgtgtccctg gccttcggcg tgatcagcct ggtgctggcc    4080
tgctacctga tgtacaagca gagagcccag cagaaaaccc tgctgtggct gggcaataac    4140
accctggacc agatgagggc caccaccaga acctgatgag cggccgcgat atcaataaaa    4200
tatctttatt ttcattacat ctgtgtgttg gttttttgtg tgaatcgata gtactaacat    4260
acgctctcca tcaaaacaaa acgaaacaaa acaaactagc aaaataggct gtccccagtg    4320
caagtgcagg tgccagaaca tttctct                                         4347
```

<210> SEQ ID NO 26
<211> LENGTH: 5149
<212> TYPE: DNA
<213> ORGANISM: artificial sequence
<220> FEATURE:
<223> OTHER INFORMATION: Plasmid pFwtIRESgD for vHVT322
<220> FEATURE:
<221> NAME/KEY: mCMV promoter
<222> LOCATION: (1)..(1391)
<220> FEATURE:
<221> NAME/KEY: NDV-Fwt VIId
<222> LOCATION: (1400)..(3061)
<220> FEATURE:
<221> NAME/KEY: IRES
<222> LOCATION: (3072)..(3634)
<220> FEATURE:
<221> NAME/KEY: ILTgD
<222> LOCATION: (3638)..(4942)
<220> FEATURE:
<221> NAME/KEY: SV40 Poly A
<222> LOCATION: (4951)..(5149)

<400> SEQUENCE: 26
aactccgccc gttttatgac tagaaccaat agtttttaat gccaaatgca ctgaaatccc 60
ctaatttgca aagccaaacg ccccctatgt gagtaatacg ggactttttt acccaatttc 120
ccacgcggaa agccccctaa tacactcata tggcatatga atcagcacgg tcatgcactc 180
taatggcggc ccatagggac tttccacata gggggcgttc accatttccc agcatagggg 240
tggtgactca atggccttta cccaagtaca ttgggtcaat gggaggtaag ccaatgggtt 300
tttcccatta ctggcaagca cactgagtca aatgggactt tccactgggt tttgcccaag 360
tacattgggt caatgggagg tgagccaatg ggaaaaaccc attgctgcca agtacactga 420
ctcaataggg actttccaat gggtttttcc attgttggca agcatataag gtcaatgtgg 480

```
gtgagtcaat agggactttc cattgtattc tgcccagtac ataaggtcaa taggggtga      540
atcaacagga aagtcccatt ggagccaagt acactgcgtc aatagggact ttccattggg     600
ttttgcccag tacataaggt caatagggga tgagtcaatg ggaaaaaccc attggagcca     660
agtacactga ctcaataggg acttttccatt gggttttgcc cagtacataa ggtcaatagg   720
gggtgagtca acaggaaagt tccattggag ccaagtacat tgagtcaata gggactttcc    780
aatgggtttt gcccagtaca taaggtcaat gggaggtaag ccaatgggtt tttcccatta    840
ctggcacgta tactgagtca ttagggactt tccaatgggt tttgcccagt acataaggtc    900
aatagggtg aatcaacagg aaagtcccat tggagccaag tacactgagt caataggac      960
tttccattgg gttttgccca gtacaaaagg tcataggggg tgagtcaat gggttttcc      1020
cattattggc acgtacataa ggtcaatagg ggtgagtcat tgggttttc cagccaattt     1080
aattaaaacg ccatgtactt tcccaccatt gacgtcaatg gctattgaa actaatgcaa     1140
cgtgaccttt aaacggtact ttcccatagc tgattaatgg gaaagtaccg ttctcgagcc    1200
aatacacgtc aatgggaagt gaaagggcag ccaaaacgta acaccgcccc ggttttcccc    1260
tggaaattcc atattggcac gcattctatt ggctgagctg cgttctacgt gggtataaga    1320
ggcgcgacca gcgtcggtac cgtcgcagtc ttcggtctga ccaccgtaga acgcagagct    1380
cctcgctgca ggcggccgca tgggctccaa accttctacc aggatcccag cacctctgat    1440
gctgatcacc cggattatgc tgatattggg ctgtatccgt ccgacaagct ctcttgacgg    1500
caggcctctt gcagctgcag gaattgtagt aacaggagat aaggcagtca atgtatacac    1560
ttcgtctcag acagggtcaa tcatagtcaa gttgctcccg aatatgccca gggataagga    1620
ggcgtgtgca aaagccccat tagaggcata aacagaaca ctgactactt tgctcactcc     1680
tcttggcgac tccatccgca agatccaagg gtctgtgtcc acatctggag gaggcaagca    1740
aggccgcctg ataggtgctg ttattggcag tgtagctctt ggggttgcaa cagcggcaca    1800
gataacagca gctgcggccc taatacaagc caaccagaat gccgccaaca tcctccggct    1860
taaggagagc attgctgcaa ccaatgaagc tgtgcatgaa gtcaccgacg gattatcaca    1920
actatcagtg gcagttggga agatgcagca gtttgtcaat gaccagttta ataatacggc    1980
gcgagaattg gactgtataa aaatcacaca acaggttggt gtagaactca acctatacct    2040
aactgaattg actacagtat tcgggccaca gatcacctcc cctgcattaa ctcagctgac    2100
catccaggca ctttataatt tagctggtgg caatatggat tacttattaa ctaagttagg    2160
tatagggaac aatcaactca gctcgttaat tggtagcggc ctgatcactg ttaccctat    2220
actgtatgac tcacagactc aactcttggg catacaagtg aatttaccct cagtcgggaa    2280
cttaaataat atgcgtgcca cctatttgga gaccttatct gtaagtacaa ccaaaggata    2340
tgcctcagca cttgtcccga agtagtgac acaagtcggt tccgtgatag aagagcttga     2400
cacctcatac tgtatagagt ccgatctgga tttatattgt actagaatag tgacattccc    2460
catgtcccca ggtatttatt cctgtttgag cggcaacaca tcagcttgca tgtattcaaa    2520
gactgaaggc gcactcacta cgccgtatat ggcccttaaa ggctcagtta ttgccaattg    2580
taaaataaca acatgtagat gtacagaccc tcctggtatc atatcgcaaa attatggaga    2640
agctgtatcc ctgatagata gacattcgtg caatgtctta tcattagacg ggataactct    2700
aaggctcagt ggggaatttg atgcaactta tcaaaagaac atctcaatac tagattctca    2760
agtcatcgtg acaggcaatc ttgatatatc aactgaactt ggaaacgtca acaattcaat    2820
```

```
cagcaatgcc ttggataggt tggcagaaag caacagcaag ctagaaaaag tcaatgtcag    2880
actaaccagc acatctgctc tcattaccta tattgttcta actgtcattt ctctagtttt    2940
cggtgcactt agtctggtgt tagcgtgtta cctgatgtac aaacagaagg cacaacaaaa    3000
gaccttgcta tggcttggga ataatacccct cgatcagatg agagccacta caagagcatg    3060
agcggccgcc cccccccccc ctaacgttac tggccgaagc cgcttggaat aaggccggtg    3120
tgcgtttgtc tatatgttat tttccaccat attgccgtct tttggcaatg tgagggcccg    3180
gaaacctggc cctgtcttct tgacgagcat tcctaggggt cttccccctc tcgccaaagg    3240
aatgcaaggt ctgttgaatg tcgtgaagga agcagttcct ctggaagctt cttgaagaca    3300
aacaacgtct gtagcgaccc tttgcaggca gcggaaccccc ccacctggcg acaggtgcct    3360
ctgcggccaa aagccacgtg tataagatac acctgcaaag gcggcacaac cccagtgcca    3420
cgttgtgagt tggatagttg tggaaagagt caaatggctc tcctcaagcg tattcaacaa    3480
ggggctgaag gatgcccaga aggtacccca ttgtatggga tctgatctgg ggcctcggtg    3540
cacatgcttt acatgtgttt agtcgaggtt aaaaaacgtc taggcccccc gaaccacggg    3600
gacgtggttt tccttttgaaa aacacgatga taataccatg caccgtcctc atctcagacg    3660
gcactcgcgt tactacgcga aaggagaggt gcttaacaaa cacatggatt gcggtggaaa    3720
acggtgctgc tcaggcgcag ctgtattcac tcttttctgg acttgtgtca ggattatgcg    3780
ggagcatatc tgctttgtac gcaacgctat ggaccgccat ttattttga ggaatgcttt    3840 ttggactatc gtactgcttt cttccttcgc tagccagagc accgccgccg tcacgtacga    3900
ctacatttta ggccgtcgcg cgctcgacgc gctaaccata ccggcggttg gcccgtataa    3960
cagatacctc actagggtat caagaggctg cgacgttgtc gagctcaacc cgatttctaa    4020
cgtggacgac atgatatcgg cggccaaaga aaaagagaag gggggcccctt tcgaggcctc    4080 cgtcgtctgg ttctacgtga ttaagggcga cgacggcgag gacaagtact gtccaatcta    4140
tagaaaagag tacagggaat gtggcgacgt acaactgcta tctgaatgcg ccgttcaatc    4200
tgcacagatg tgggcagtgg actatgttcc tagcacccctt gtatcgcgaa atggcgcggg    4260
actgactata ttctcccccca ctgctgcgct ctctggccaa tacttgctga ccctgaaaat    4320
cgggagattt gcgcaaacag ctctcgtaac tctagaagtt aacgatcgct gtttaaagat    4380
cgggtcgcag cttaactttt taccgtcgaa atgctggaca acagaacagt atcagactgg    4440
atttcaaggc gaacaccttt atccgatcgc agacaccaat acacgacacg cggacgacgt    4500
atatcgggga tacgaagata ttctgcagcg ctggaataat ttgctgagga aaaagaatcc    4560
tagcgcgcca gaccctcgtc cagatagcgt cccgcaagaa attcccgctg taaccaagaa    4620
agcggaaggg cgcaccccgg acgcagaaag cagcgaaaag aaggcccctc cagaagactc    4680
ggaggacgac atgcaggcag aggcttctgg agaaaatcct gccgcccctcc ccgaagacga    4740 cgaagtcccc gaggacaccg agcacgatga tccaaactcg gatcctgact attacaatga    4800
catgcccgcc gtgatcccgg tggaggagac tactaaaagt tctaatgccg tctccatgcc    4860
catattcgcg gcgttcgtag cctgcgcggt cgcgctcgtg gggctactgg tttggagcat    4920
cgtaaaatgc gcgcgtagct aagcggccgc ggggatccag acatgataag atacattgat    4980
gagtttggac aaaccacaac tagaatgcag tgaaaaaaat gctttatttg tgaaatttgt    5040
gatgctattg ctttatttgt aaccattata agctgcaata aacaagttaa caacaacaat    5100
tgcattcatt ttatgtttca ggttcagggg gaggtgtggg aggttttttt                5149
```

<210> SEQ ID NO 27
<211> LENGTH: 1857
<212> TYPE: DNA
<213> ORGANISM: artificial sequence
<220> FEATURE:
<223> OTHER INFORMATION: plasmid pHVTUS2SvgDwtsyn for vHVT406
<220> FEATURE:
<221> NAME/KEY: SV40 promoter
<222> LOCATION: (1)..(362)
<220> FEATURE:
<221> NAME/KEY: ILTV gD
<222> LOCATION: (379)..(1683)
<220> FEATURE:
<221> NAME/KEY: Syn Poly A
<222> LOCATION: (1695)..(1857)

<400> SEQUENCE: 27
gagctcggta cagcttggct gtggaatgtg tgtcagttag ggtgtggaaa gtccccaggc 60
tccccagcag gcagaagtat gcaaagcatg catctcaatt agtcagcaac caggtgtgga 120
aagtccccag gctccccagc aggcagaagt atgcaaagca tgcatctcaa ttagtcagca 180
accatagtcc cgcccctaac tccgcccatc ccgcccctaa ctccgcccag ttccgcccat 240
tctccgcccc atggctgact aattttttttt atttatgcag aggccgaggc cgcctcggcc 300
tctgagctat tccagaagta gtgaggaggc ttttttggag gcctaggctt ttgcaaaaag 360
ctgcggccgg ccgccaccat gcaccgtcct catctcagac ggcactcgcg ttactacgcg 420
aaaggagagg tgcttaacaa acacatggat tgcggtggaa aacggtgctg ctcaggcgca 480
gctgtattca ctcttttctg gacttgtgtc aggattatgc gggagcatat ctgctttgta 540
cgcaacgcta tggaccgcca tttatttttg aggaatgctt tttggactat cgtactgctt 600
tcttccttcg ctagccagag caccgccgcc gtcacgtacg actacatttt aggccgtcgc 660
gcgctcgacg cgctaaccat accggcggtt ggcccgtata acagatacct cactagggta 720
tcaagaggct gcgacgttgt cgagctcaac ccgatttcta acgtggacga catgatatcg 780
gcggccaaag aaaaagagaa ggggggccct ttcgaggcct ccgtcgtctg gttctacgtg 840
attaagggcg acgacggcga ggacaagtac tgtccaatct atagaaaaga gtacagggaa 900
tgtggcgacg tacaactgct atctgaatgc gccgttcaat ctgcacagat gtgggcagtg 960
gactatgttc ctagcaccct tgtatcgcga aatggcgcgg gactgactat attctccccc 1020
actgctgcgc tctctggcca atacttgctg accctgaaaa tcgggagatt tgcgcaaaca 1080
gctctcgtaa ctctagaagt taacgatcgc tgtttaaaga tcgggtcgca gcttaacttt 1140
ttaccgtcga aatgctggac aacagaacag tatcagactg gatttcaagg cgaacacctt 1200
tatccgatcg cagacaccaa tacacgacac gcggacgacg tatatcgggg atacgaagat 1260
attctgcagc gctggaataa tttgctgagg aaaaagaatc ctagcgcgcc agaccctcgt 1320
ccagatagcg tcccgcaaga aattcccgct gtaaccaaga aagcggaagg gcgcaccccg 1380
gacgcagaaa gcagcgaaaa gaaggcccct ccagaagact cggaggacga catgcaggca 1440
gaggcttctg gagaaaatcc tgccgccctc cccgaagacg acgaagtccc cgaggacacc 1500
gagcacgatg atccaaactc ggatcctgac tattacaatg acatgcccgc cgtgatcccg 1560
gtggaggaga ctactaaaag ttctaatgcc gtctccatgc ccatattcgc ggcgttcgta 1620
gcctgcgcgg tcgcgctcgt ggggctactg gtttggagca tcgtaaaatg cgcgcgtagc 1680

-continued

| | | | | |
|---|---|---|---|---|
| taatcgagcc | tagaggcaat | aaaatatctt | tattttcatt | acatctgtgt gttggttttt | 1740 |
| tgtgtgaatc | gatagtacta | acatacgctc | tccatcaaaa | caaaacgaaa caaaacaaac | 1800 |
| tagcaaaata | ggctgtcccc | agtgcaagtg | caggtgccag | aacatttctc tctcgag | 1857 |